United States Patent [19]

Golman et al.

[11] Patent Number: 5,700,448
[45] Date of Patent: Dec. 23, 1997

[54] USE OF PERSISTENT FREE-RADICALS IN MAGNETIC RESONANCE IMAGING

[75] Inventors: Klaes Golman, Rungsted Kyst, Denmark; Sven Andersson, Lomma, Sweden; Frode Rise, Oslo, Norway; Lars-Goran Wistrand, Lund; Hakan Wikstrom, Groningen, both of Sweden

[73] Assignee: Nycomed Imaging AS, Oslo, Norway

[21] Appl. No.: 415,662

[22] Filed: Apr. 3, 1995

Related U.S. Application Data

[62] Division of Ser. No. 190,045, filed as PCT/EP92/01793, Aug. 6, 1992, Pat. No. 5,435,991.

[30] Foreign Application Priority Data

Aug. 9, 1991 [GB] United Kingdom ............... 91-17211.4
Aug. 12, 1991 [GB] United Kingdom ............... 91-17418.5

[51] Int. Cl.$^6$ ........................................ A61B 5/055
[52] U.S. Cl. .................... 424/9.33; 424/9.3; 436/173; 514/443; 514/463; 514/730; 549/31; 549/433
[58] Field of Search .................... 424/9.33, 9.3; 436/173; 128/653.4, 654; 514/443, 463, 730; 549/31, 433

[56] References Cited

U.S. PATENT DOCUMENTS

| 4,499,095 | 2/1985 | Rosseels et al. | 514/299 |
|---|---|---|---|
| 4,656,026 | 4/1987 | Coffman et al. | 424/9.33 |
| 4,863,717 | 9/1989 | Keana | 424/9 |
| 4,882,327 | 11/1989 | King | 514/214 |
| 4,957,925 | 9/1990 | Gubin et al. | 514/299 |
| 4,985,063 | 1/1991 | Fischer et al. | 71/88 |
| 5,028,614 | 7/1991 | Liu et al. | 514/306 |
| 5,066,807 | 11/1991 | Anzeveno et al. | 546/183 |
| 5,223,510 | 6/1993 | Gubin et al. | 514/299 |
| 5,264,204 | 11/1993 | Cacheris et al. | 424/9.33 |
| 5,362,477 | 11/1994 | Moore et al. | 424/9.33 |

FOREIGN PATENT DOCUMENTS

WO-A-91 12044  8/1991  WIPO.

OTHER PUBLICATIONS

Skowrońska–Ptasińska et al., J. Organometallic Chemistry 141(2):149–156 (1977).
Lurie et al., Journal of Magnetic Resonance, 76, 366–370, 1988.
Grucker, Magnetic Resonance in Medicine, 14, 140–147, 1990.
Nagamura et al., Chemical Abstracts, 96, 10, Abstract No. 70290a, 1981.
Fessenden et al., Chemical Abstracts, 94, 22, Abstract No. 183019w, 1981.
Clough et al., Chemical Abstracts, 83,10, Abstract No. 88194p, 1975.
Wadsworth et al., J. Org. Chem., 51, 24, 4639–4644, 1986.
Mueller–Warmuth et al., Chemical Abstracts, 74, 8, Abstract No. 35176s, 1970.
Kalyanaraman et al., The Journal of Biological Chemistry, 264, 19, 11014–11019, 1989.

Primary Examiner—Gary E. Hollinden
Attorney, Agent, or Firm—Bacon & Thomas

[57] ABSTRACT

The present invention relates to the use of persistent free radicals, in particular persistent free radicals having a carbon-based π-bonded electronic system available for delocalization of the unpaired electrons as image enhancing agents in magnetic resonance imaging (MRI), in particular electron spin resonance enhanced magnetic resonance imaging (ESREMRI). The invention also relates to contrast media containing such radicals and to the use of such radicals and their non-radical precursors in the manufacture of MRI and ESREMRI contrast media.

8 Claims, No Drawings

USE OF PERSISTENT FREE-RADICALS IN MAGNETIC RESONANCE IMAGING

This application is a Division of application Ser. No. 08/190,045, filed Mar. 18, 1994, now U.S. Pat. No. 5,435, 991 which is a 371 of PCT/EP92/01783 filed Aug. 6, 1992.

The present invention relates to the use of persistent free radicals, in particular persistent free radicals having a carbon-based π-bonded electronic system available for delocalization of the unpaired electrons (hereinafter "persistent π-system radicals"), as image enhancing agents in magnetic resonance imaging (MRI) as well as to contrast media containing such radicals and to the use of such radicals and their non-radical precursors in the manufacture of MRI contrast media.

MRI is a diagnostic technique that has become particularly attractive to physicians as it is non-invasive and does not involve exposing the patient under study to potentially harmful radiation, such as for example the X-radiation of conventional radiography.

This technique, however suffers from several serious drawbacks, including in particular the expense of manufacture and operation of the MRI apparatus, the relatively long scanning time require to produce an image of acceptable spatial resolution, and the problem of achieving contrast in the magnetic resonance (MR) images between tissue types having the same or closely similar imaging parameters, for example in order to cause a tissue abnormality to show up clearly in the images.

The expense of manufacture and operation of an MRI apparatus is closely associated with the strength of the magnetic field that the primary magnet in the apparatus is required to generate in order to produce images of acceptable spatial resolution in an acceptable time.

MR images are generated by manipulation of the MR signals detected from the sample, for example a human or animal body, placed in a magnetic field and exposed to pulses of radiation of a frequency (typically radiofrequency (RF)) selected to excite MR transitions in selected non-zero spin nuclei (the "imaging nuclei", which are generally water protons in body fluids) in the sample.

The amplitude of the induced MR signals is dependent upon various factors such as the strength of the magnetic field experienced by the sample, the temperature of the sample, the density of the imaging nuclei within the sample, the isotopic nature and chemical environment of the imaging nuclei and the local inhomogeneities in magnetic field experienced by the imaging nuclei.

Thus many techniques have been proposed for enhancing MR image quality, for example by increasing MR signal amplitude or by increasing the difference in MR signal amplitude between different tissue types.

The imaging parameters (nuclear density, $T_1$ and $T_2$) for tissues of interest may be altered and many proposals have been made for doing this by the administration of magnetically responsive materials into patients under study (see for example EP-A-71564 (Schering), EP-A-133674 (Schering) and WO-A-85/04330 (Jacobsen)). Where such materials, generally referred to as MRI contrast agents, are paramagnetic they produce significant reduction in the $T_1$ of the water protons in the body zones into which they are administered or at which they congregate, and where the materials are ferromagnetic or superparamagnetic (for example as suggested by Jacobsen) they produce a significant reduction in the $T_2$ of the water protons. In either case the result is enhanced (positive or negative) contrast in the MR images of such zones.

The contrast enhancement achievable by such agents in conventional MRI is relatively limited and it is generally not such as to allow a reduction in the image acquisition period or in the field strength of the primary magnet.

Utilisation of the spin transition coupling phenomenon known as dynamic nuclear polarisation or as the Overhauser effect to amplify the population difference between the ground and excited spin states of the imaging nuclei by the excitation of a coupled ESR transition in a paramagnetic species present in the sample being imaged has been described by Hafslund Nycomed Innovation AB in WO-A-88/10419.

This new technique for generating a MR image of the sample, which is hereinafter termed electron spin resonance enhanced magnetic resonance imaging (ESREMRI) or Overhauser MRI (OMRI), involves exposing the sample to a first radiation of a frequency selected to excite nuclear spin transitions in selected nuclei in the sample (radiation which is generally of radiofrequency or thereabouts and thus for convenience will be referred to hereinafter as RF radiation) and also exposing the sample to a second radiation of a frequency selected to excite electron spin transitions coupled to nuclear spin transitions for at least some of the selected nuclei (radiation which is generally of microwave frequency or thereabouts and thus for convenience is referred to hereinafter as MW or UHF radiation), the MR images being generated from the resulting amplified MR signals (free induction decay signals) emitted by the sample.

The paramagnetic substance which possesses the ESR transition which couples with the NMR transition of the imaging nuclei may be naturally present within the imaging sample or more usually may be administered as an OMRI contrast agent.

In WO-A-88/10419 various OMRI contrast agents were proposed, for the most part these being nitroxide stable free radicals, although the use of the chloranil semiquinone radical and of Fremy's salt was also proposed.

In WO-A-90/00904 Hafslund Nycomed Innovation AB proposed the use of deuterated stable free radicals, in particular deuterated nitroxide stable free radicals, as OMRI contrast agents.

Organic free radicals however frequently have properties which render them unsuitable for use as OMRI contrast agents. Thus free radicals commonly are unstable in physiological conditions, or have very short half-lives leading to toxicity problems. A further drawback is the low relaxivity exhibited by many free radicals, which results in poor coupling of the electron and nuclear spin transitions and thus a poor enhancement of the magnetic resonance signal. A need therefore exists for improved free radical OMRI contrast agents and in WO-A-91/12024 Hafslund Nycomed Innovation AB proposed the use of carbon free radicals, and in particular various triarylmethyl radicals. The disclosure of WO-A-91/12024 is incorporated herein by reference.

For such free radicals to be effective, they should be relatively long lived and to distinguish from free radicals which have a momentary existence, those usable as OMRI contrast agents will be referred to herein as being "persistent" free radicals, that is having a half life of at least one minute at ambient temperature.

We have now found that other π-system radicals are useful as OMRI contrast agents and viewed from one aspect the present invention provides the use of a persistent π-system radical for the manufacture of a contrast medium for use in MRI, and especially for use in OMRI, wherein the electron delocalizing π-system of said radical comprises at least one homo or heterocyclic ring, said radical being other than the chloranil semiquinone anion radical, preferably other than perhalo radicals and especially preferably other than a triarylmethyl radical and particularly preferably said radical having an inherent linewidth for the peaks in its esr spectrum of less than 500 mG, especially less than 100 mG, and most especially no more than 50 mG.

The cyclic π-system radicals used according to the present invention thus involve as a basic structural component a structure which, in one mesomeric form, can be represented as

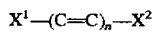

where X¹ represents O, S, N—,

or, less favourably

X² represents an atom or group capable of participating in the π-bond system of the (C=C)$_n$ moiety, e.g. O—, S—,

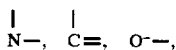

etc;

C=C is an unsaturatedly bonded carbon atom pair;

n is a positive integer, i.e. having a value of at least 1, preferably at least 2 and especially preferably up to 20, especially up to 10, e.g. 1, 2, 3, 4, 5 or 6; and where the atom chain X¹—(C=C)$_n$—X² contains or at least in part is a component of an unsaturated carbo- or heterocyclic ring, said ring preferably containing 5 to 8 members and optionally carrying one or more, preferably 1, 2 or 3, fused carbo- or heterocyclic rings also participating in the π-system.

The π-system radicals used according to the present invention may contain more than one unpaired electron; although if this is the case the unpaired electrons should most preferably be involved in separate delocalizing π-systems, i.e. biradicals rather than triplet state radicals are preferred since the latter are generally less stable.

Since it is generally preferred for OMRI contrast agents that their esr spectra should contain as few lines as possible, it is especially preferred that the number of non-zero spin nuclei in the proximity of high free electron density sites within the radical should be as low as possible. Accordingly proton (¹H) substitution of the atoms of the π-system atom chain should be minimized and while halogen atoms such as chlorines may (by virtue of their vacant d orbitals) participate in the π-system and so enhance radical stability their presence as substituents on or as X² components of the π-system atom chain is generally to be avoided.

From the foregoing, it will be appreciated that a single radical may include more than one π-system atom chain X¹—(C=C)$_n$X² and indeed it is generally preferred that this should be the case. It is however generally to be preferred that for a system where X¹ is nitrogen the corresponding X² should be other than nitrogen or that no more than one corresponding X² be nitrogen. Otherwise however, and especially where X¹ is oxygen or carbon, it may be desirable that X¹ and X² should be the same element and more particularly that the two atoms should be capable of equivalent electronic configurations in alternative mesomeric forms of the radical, as is for example the case with galvinoxyl radicals which offer two resonance structures with alternative equivalent sites for the —O moieties.

Examples of suitable central π-system skeletons for cyclic π-system radicals usable according to the invention thus include the following:

where Ar represents an aryl group, e.g. a 5–8 membered carbo or heterocyclic group itself optionally carrying fused rings serving to extend the π-system. Where more than one Ar group is present they may be identical or different or even joined. Thus more explicit examples of cyclic π-system radical skeletons include

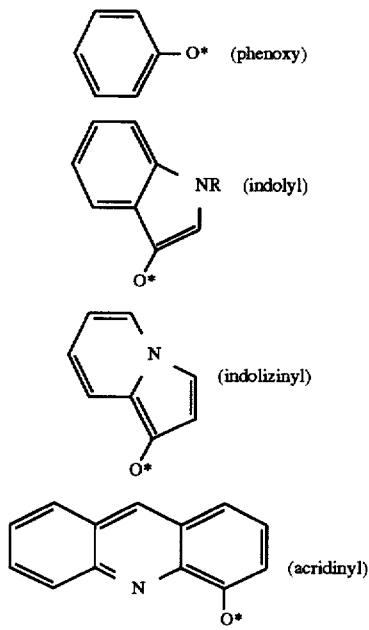

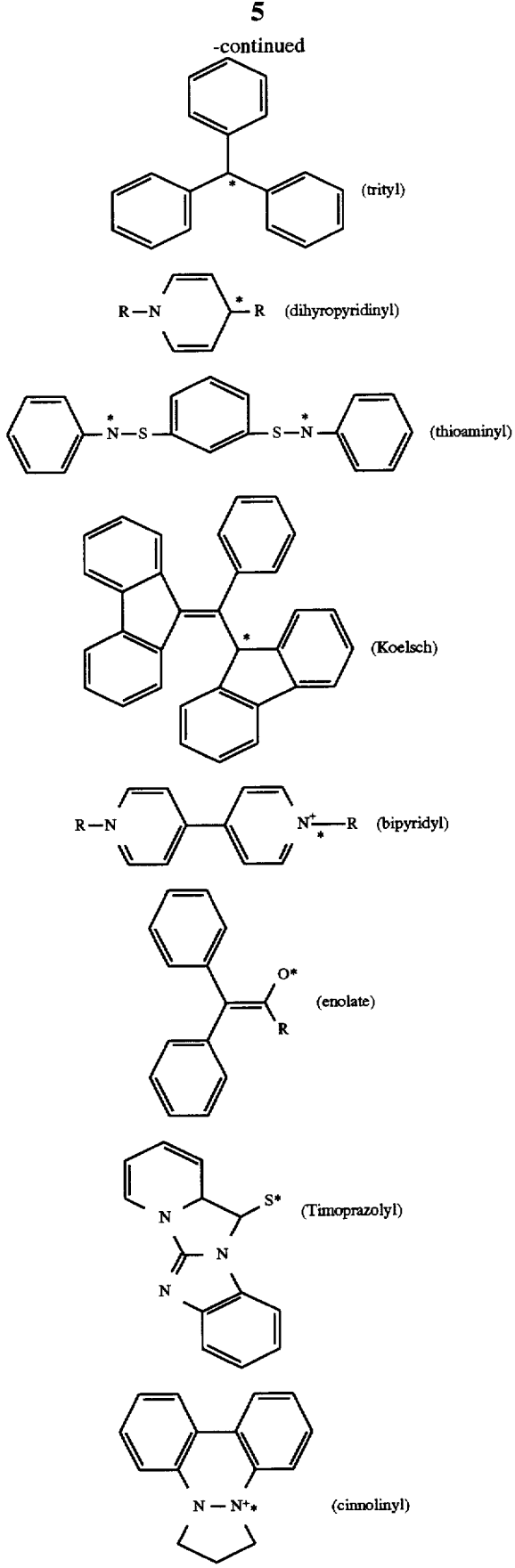
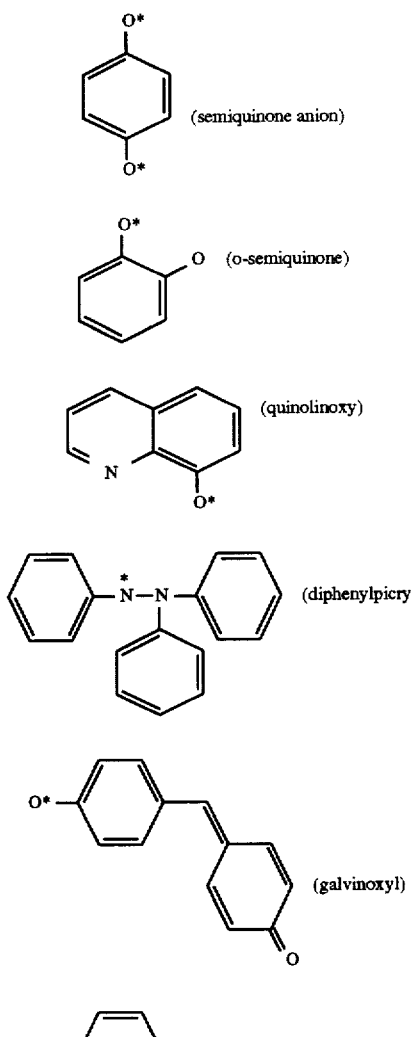

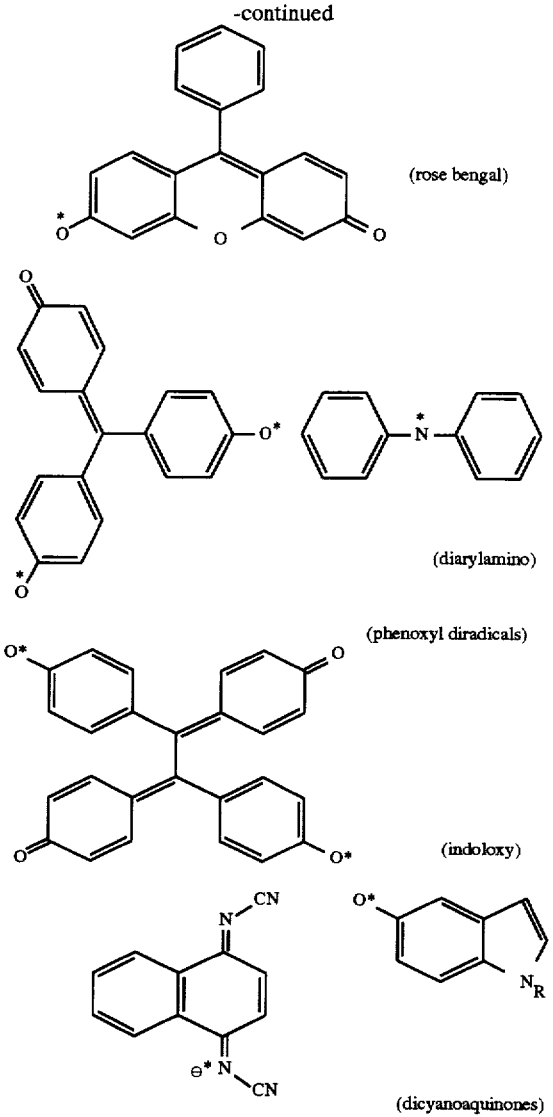

(rose bengal)

(diarylamino)

(phenoxyl diradicals)

(indoloxy)

(dicyanoaquinones)

(where "R" implies that a substituent, e.g. hydrogen, alkyl etc. is required).

In the skeletal structures indicated above, —O and —S moieties are generally interchangeable and fused aryl rings may be added on if desired, subject of course to the general preference that the π-system should preferably contain no more than 4, especially no more than 3, fused rings.

While radicals according to the invention may have charged $X^2$ groups, such radicals will generally be less preferred.

In order that the π-system radicals should perform most effectively as MRI contrast agents it will generally be preferred that the atoms of the $X^1(C\!=\!\!C)_nX^2$ chain and indeed of any conjugated ring systems be substituted. In this regard substitution is intended to fulfil a dual or treble function—to stabilize the radical and to reduce esr linewidths and/or reduce the number of lines in the esr spectrum. Of course for many structures or substitution sites one or more of these functions can be achieved by the same manner of substitution.

Thus as mentioned above, substitution should generally be designed to minimize the occurrence of non-zero spin nuclei (especially hydrogen ($^1$H)) at or even closely adjacent sites of high free electron density. Above and beyond this however substitution should generally be such as to block off or sterically hinder approach to atoms having high free electron density, so reducing radical reactivity and increasing stability, and also to provide electron withdrawing or electron donating substituents at sites where such effects serve to enhance stability. Generally speaking, electron donor or withdrawing substituents should preferably be selected to minimize esr line broadening or line splitting effects and sterically hindering or blocking groups should be selected to achieve their steric effect of hindering intermolecular approach with minimal deformation of the delocalizing π-system as such deformation reduces the radical stabilizing efficacy of the system.

Although discussed further below, steric hindrance of neighbouring ring sites is preferably effected by substitution with t-butyl-thio, t-butoxy or t-butyl groups or by substitution of ortho and meta positions by bridging groups of formula $X^7\!-\!CR^7{}_2X^7$, where each $X^7$, which may be the same or different is O, S, C=O or $SO_2$ (both $X^7$ preferably being O or CO) and $R^7$ is a hydrogen atom or a $C_{1-6}$alkyl group optionally substituted by hydroxyl, $C_{1-6}$alkoxy or carboxyl groups or amides, esters or salts thereof, e.g. a —O—C(CH$_3$)$_2$—O— group.

Among electron withdrawing groups for substitution of the radical skeleton, nitrile, sulphonate, sulphone, sulphonamide and salts thereof (e.g. $R^2SO_2$, $R^2OCOSO_2$ and $R^2{}_2NCOSO_2$) and, more preferably, carboxyl groups (and esters, amides and salts thereof) are especially preferred. Within any one aryl ring however, generally only one or at most two such electron withdrawing groups will be desired.

For electron donor groups, especially those at a para (or δ) position to a radical centre $X^1$ group, groups of formula $R^2O$ and $R^2S$ are especially preferred where $R^2$ is hydrogen or $C_{1-6}$alkyl optionally substituted by hydroxyl, or $C_{1-6}$alkoxy, amine, $C_{1-6}$alkyl or dialkyl amine, carboxyl (and amides and esters thereof) etc.

Although many persistent cyclic π-system radicals are known, those having —$X^7$—$CR^7{}_2$—$X^7$— steric hindrance groups substituted on neighbouring carbon atoms of the ring systems and those having $SO_2R^3$ (where $R^3$ is $R^2$, $CO_2R^2$ or $CONR_2{}^2$) solubilizing and/or stabilizing groups are novel and particularly suited for use according to the invention and thus form a further aspect of the invention.

Viewed from a still further aspect, the invention also provides a method of magnetic resonance investigation of a sample, said method comprising introducing into said sample a persistent cyclic π-system radical as discussed above, exposing said sample to a first radiation of a frequency selected to excite electron spin transitions in said free radical, exposing said sample to a second radiation of a frequency selected to excite nuclear spin transitions in selected nuclei in said sample, detecting free induction decay signals from said sample, and, optionally, generating an image or dynamic flow data from said detected signals.

Viewed from another aspect, the invention also provides a magnetic resonance imaging contrast medium comprising a physiologically tolerable persistent cyclic π-system free radical together with at least one pharmacologically acceptable carrier or excipient.

For in vivo imaging, the free radical should of course preferably be a physiologically tolerable radical, or one presented in a physiologically tolerable, e.g. encapsulated, form.

Preferred free radicals for use according to the invention exhibit high stability to oxygen, to pH, for example in the range pH 5–9, and in aqueous solution, particularly stability up to a concentration of 300 mM. Further desirable characteristics include reduced tendency to dimerization, long half-life, preferably greater than 1 minute, particularly preferably greater than 1 hour and especially preferably 1 year, long relaxation times, both $T_{1e}$ and $T_{2e}$ preferably being greater than 1 μsec, high relaxivity, for example greater than 0.3 $mM^{-1}sec^{-1}$ and a small number of esr transition lines.

As indicated above, the possibility exists to optimize different characteristics, e.g. solubility, stability and line broadening, of the overall radical by appropriate combinations of different substituents on the radical skeleton. Combinations, where one or more substituent is selected to optimize stability and line broadening, and one or more substituent is selected to optimize solubility are considered particularly interesting.

In order to optimize the above-mentioned desirable properties, a number of criteria need to be borne in mind in selecting or constructing radicals for use according to the invention.

Thus, the aromatic rings of the radicals advantageously are substituted and the nuclear identities of nuclei in all substituents and their positions within the molecule should be selected so as to minimise their effect (line splitting or broadening) on the esr transitions. In general, in a $X^1(C^1=C^2)_nX^2$ structure, it is especially desirable that the $C^2$ carbons should be substituted, particularly any $C^2$ carbon in a position δ to an $X^1$ moiety. Substitution of $C^2$ carbons is desirable in order to minimise dimerisation and oxygen attack on the molecule. $C^2$ carbons in the β position relative to any $X^1$ moiety are preferably bulky substituents to minimise attack by oxygen and substitution of δ $C^2$ carbons by electron withdrawing and/or water solubilizing groups is also particularly preferred. Such substituents preferably have no magnetic moment, or have a very low effective spin density. Alternatively, in order to minimise their effect on the esr transition, the substituents should be bonded in such a manner that they are capable of free rotation.

In the radicals used according to the invention, the carbons of the π-system, e.g. carbons in unsaturated chains or rings, preferably carry substituents other than protons ($^1H$) and indeed it is preferred that only one such carbon at most is unsubstituted. Suitable substituents include groups $R^1$ which may be the same or different, and independently represent alkyl groups or groups of formula —M, —$X^3M$, —$X^3Ar^2$ where M represents a water solubilizing group, each group $X^3$, which may be the same or different, represents an oxygen or sulphur atom or a NH, $CH_2$, CO or $SO_2$ group; $Ar^2$ represents a 5 to 10 membered aromatic ring optionally substituted by a solubilizing group M; or $R^1$ groups on different or adjacent $R^1$ groups (preferably groups at the α and β positions to an $X^1$ moiety) together with the two intervening carbon atoms may represent groups of formula

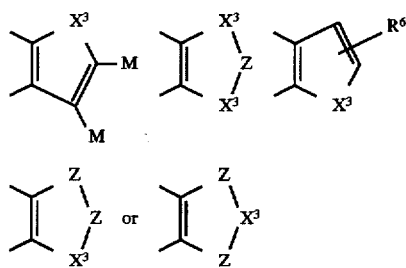

where $R^6$ represents a hydrogen atom, a hydroxyl group, an optionally alkoxylated, optionally hydroxylated acyloxy or alkyl group or a solubilising group M; Z represents an oxygen or sulphur atom or a group $NR^5$, $CR^7_2$, or $SiR^7_2$; $R^5$ represents a hydrogen atom or an optionally hydroxylated, optionally aminated, optionally alkoxylated, optionally carboxylated alkyl, oxo-alkyl, alkenyl or alkaryl group; each $R^7$, which may be the same or different, represents a hydrogen atom, an alkyl, hydroxyalkyl, alkoxycarbonyl or carbamoyl group or two groups $R^7$ together with the atom to which they are bound represent a carbonyl group or a 5 to 8 membered cycloalkylidene, mono- or di-oxacycloalkylidene, mono- or di-azacycloalkylidene or mono- or di-thiacycloalkylidene group optionally with the ring attachment carbon replaced by a silicon atom (preferably however in any spiro structure the ring linking atom will be bonded to no more than three heteroatoms) and $R^7$ where it is other than hydrogen, is optionally substituted by a group $R^6$.

Certain of the radicals substituted in this fashion are new and they, their salts and their non-radical precursors (e.g. compounds having a structural unit $X^4X^1(C=C)_nX^2$ where $X^4$ is a leaving group, e.g. hydrogen, hydroxyl, halogen, carboxyl, $CO_2OCO.C(Ar)_3$ or $NNC(Ar)_3$) form further aspects of the present invention.

In the radicals used according to the invention the solubilizing groups M may be any of the solubilizing groups conventionally used in diagnostic and pharmaceutical products. Particularly preferred solubilizing groups M include optionally hydroxylated, optionally alkoxylated alkyl or oxo-alkyl groups and groups of formulae $R^5$, $COOR^5$, $OCOR^5$, CHO, CN, $CH_2S(O)R^5$, $CONR^5_2$, $NR^5COR^5$, $NR^5_2$, $SO_2NR^5_2$, $OR^5$, $PO_3^{2-}$, $SOR^5$, $SO_2R^5$, $SO_3M^1$, $COOM^1$ (where $M^1$ is one equivalent of a physiologically tolerable cation, for example an alkali or alkaline earth metal cation, an ammonium ion or an organic amine cation, for example a meglumine ion), —$(O(CH_2)_p)_mOR^5$ (where p is an integer having a value of from 1 to 3 and m is an integer having a value of from 1 to 5), —$CX^3(CHR^5)_pX^3$ or $CH_2R^8$ (where is a hydrophilic $R^5$ group) or $SR^{10}$ or $SO_2R^{10}$ where $R^{10}$ is a group $R^5$ or an alkyl group optionally substituted by one or more, especially two or three groups $COOR^5$, $OCOR^5$, CHO, CN, $CONR^5_2$, $NR^5COR^5$, $NR^5_2$, $SO_2NR^5_2$, $OR^5$, $PO_3^{2-}$, $SOR^5$, $SO_2R^5$, $SO_3M^1$, $COOM^1$, or —$(O(CH_2)_n)_mOR^5$.

Especially preferred as solubilizing groups M are groups or formula $C(H)_{3-p}(CH_2OH)_p$, $R^9$, $COR^9$, $SR^9$, $SOR^9$, $SO_2R^9$, $CON(R^9)_2$, $NR^9_2$, $NHR^9$ and $CONHR^9$ [where $R^9$ may represent a $C_{1-5}$alkyl group optionally substituted by hydroxyl, alkoxy or amino groups or carboxyl groups or esters or amides thereof, e.g. groups

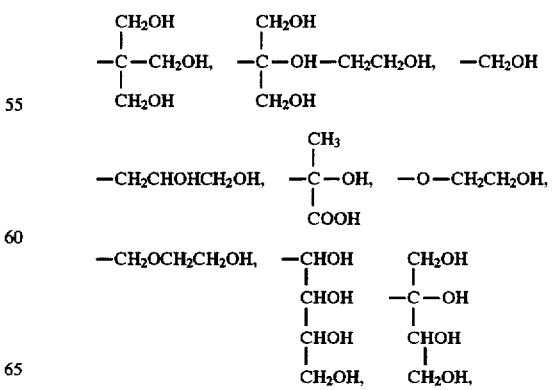

-continued

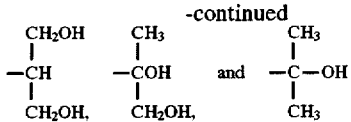

(although any R⁹ group attached to a sulphur, nitrogen or oxygen atom is preferably not hydroxylated at the α carbon)], and groups of formula SR$^{12}$ where R$^{12}$ is a group CH$_2$COOR$^{13}$, CH(COOR$^{13}$)$_2$, CH$_2$CONHR$^9$, CH$_2$CONR$^9_2$, CR$^5$(COOR$^{13}$)$_2$, CH(CN)CO$_2$R$^{13}$, (CH$_2$)$_p$SO$_3{}^{31}$M$^1$, (CH$_2$)$_p$COR$^9$, CH(COR$^9$)CH$_2$COR$^9$ and CH(R$^5$)COR$^9$ where p, M$^1$ and R$^5$ are as earlier defined and R$^{13}$ is a hydrogen atom, an alkyl group or a group M$^1$ or R$^9$.

Further especially preferred solubilising groups M or X$^3$M include groups of formula X$^5$C((CH$_2$)$_p$COOR$^{13}$)$_2$R$^{14}$, X$^5$C((CH$_2$)$_p$COOR$^{13}$)$_3$ and X$^5$C((CH$_2$)$_p$COOR$^{13}$)R$^{14}_2$, where R$^{13}$ is as defined above, p is an integer from 1 to 3, X$^5$ is an oxygen or sulphur atom, and R$^{14}$ is a hydroxyalkyl group such as a group R$^9$ as earlier defined.

Other examples of preferred R$^1$ groups include for example the following structures

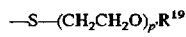

where p' is 0, 1 or 2 and R$^{19}$ is hydrogen or C$_{1-4}$alkyl

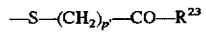

where R$^{23}$ is C$_{1-4}$alkyl (e.g. methyl, ethyl or t-butyl), NR$_2{}^{21}$ or OR$^{21}$ and R$^{21}$ is C$_{1-4}$alkyl

where R$^{22}$ is hydrogen, hydroxyl, R$^{23}$, or COOR$^{21}$

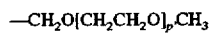

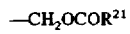

and

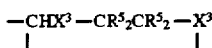

where X$^3$ is oxygen or sulphur.

Where M represents a group containing a moiety NR$^5_2$, this may also represent an optionally substituted nitrogen-attached 5 to 7 membered heterocyclic ring optionally containing at least one further ring heteroatom, e.g. N or O, for example a group of formula

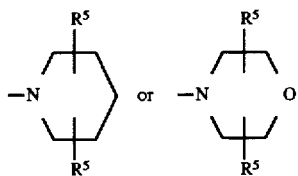

In the substituents on the radicals used according to the invention, any alkyl or alkenyl moiety conveniently will contain up to 6, especially up to 4, carbon atoms and any aryl moiety will preferably contain 5 to 7 ring atoms in the or any aromatic ring and especially preferably will comprise an aromatic ring with 0, 1 or 2 further aromatic rings fused directly or indirectly thereto.

Preferred structures for the radicals include those in which at least one pair of adjacent ring carbons of the (C═C)$_n$ moiety or of any aryl substituent carries a fused ring of formula

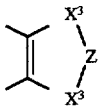

where X$^3$ and Z are as defined before, especially rings of formulae

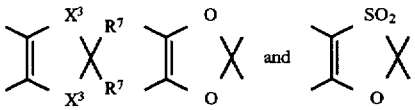

where X$^3$ is oxygen, sulphur, carbonyl or SO$_2$ and R$^7$ is hydrogen or optionally hydroxylated methyl.

As has been discussed above, the substituents on the skeleton of the π-system serve primarily to achieve one or more of the functions of i) steric hindrance (blocking), ii) electron withdrawing (from the π-system), iii) electron donating (into the π-system) and iv) enhancing the water solubility of the overall radical. The preferred electron donating blocking groups are t-butoxy t-butylthio, NR$^{70}_2$ (where R$^{70}$ is as described below) and the —X$^7$—CR$^7_2$—X$^7$— (where X$^7$ is O or S) bridging groups. The preferred electron withdrawing blocking groups include —X$^7$—CR$^7_2$—X$^7$— (where at least one X$^7$ is SO or SO$_2$) bridging groups CHO, CONR$^{70}_2$, COOR$^{70}$, OCOR$^{70}$, SO$_2$NR$^{70}_2$, SO$_2$CR$^{70}_3$, NR$^{70}$COR$^{70}$, NR$^{70}$COOR$^{70}$, OCONR$^{70}_2$, NR$^{70}$SO$_2$R$^{70}$, NR$^{70}$CONR$^{70}_2$, NR$^{70}$SO$_2$NR$^{70}_2$, COCOR$^{70}_3$, COCOR$^{70}$, SO$_2$R$^{70}$, COCOOR$^{70}$, CN, COSR$^{70}$, SOCR$^{70}_3$ and CR$^{70}$═NOR$^{70}$ where R$^{70}$ is hydrogen or alkyl or cycloalkyl (preferably C$_{1-4}$alkyl or C$_{5-6}$cycloalkyl) optionally substituted by one or more groups selected from OH, NH$_2$, CONR$^{71}_2$ and COOR$^{71}$ (preferably 1, 2 or 3 hydroxy groups) and R$^{71}$ is hydrogen or optionally hydroxylated C$_{1-3}$alkyl. Preferably R$^{70}$ is C$_{1-4}$hydroxyalkyl (e.g. CH$_2$OH, CH$_2$CH$_2$OH, CH$_2$CH$_2$CHOHCH$_2$OH, CH$_2$CHOHCHOHCH$_2$OH, CH$_2$CHOHCH$_2$OH, and C(CH$_2$OH)$_3$) or 2,3-dihydroxycyclopentyl or 2,3-dihydroxycyclohexyl.

Thus taking for illustrative purposes the Ar$_3$Cand Ar—O systems, preferred radical substitution for Ar$_3$Cis as described in PCT/EP91/00285 and examples of preferred substitution for Ar—O structures, such as for example the phenoxy, indolizinyl, indolyl, semiquinone and galvinoxyl structures, include those disclosed below:

Phenoxy:

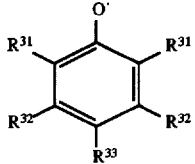

where each R$^{32}$ which may be the same or different represents a hydrogen atom, a group R$^{31}$ or a solubilizing group, e.g. a group M; R$^{33}$ represents a group M$^{20}$ or, less preferably, R$^{31}$; each R$^{31}$, which may be the same or different, represents a steric hindrance group, e.g. t-butyl or more preferably a —O—t-butyl or —S—t-butyl group, or two groups R$^{31}$ on adjacent carbons together represent a steric hindrance bridging group e.g. a group —X⁷—CR⁷₂—X⁷—, or X⁷—NR⁵—X⁷— it being particularly convenient that both sets of R³¹ and R³² groups represent such bridging groups; M²⁰ represents an electron donor group, e.g. a group OR⁹, SR⁹ (where R⁹ is preferably methyl), —CR³⁶=CR³⁴R³⁵ (where R³⁴ and R³⁵ are hydrogen, cyano, alkyl, aryl, or carboxyl or an amide or ester thereof and R³⁶ is hydrogen or alkyl), or —CR³⁶=N—R³⁷ (where R³⁷ is alkyl), preferably a group capable of lying in the plane of the phenyl ring.

Examples of suitable steric hindrance R³¹ groups include Ar—O—, Ar—S—, Ar—SO₂—, Ar—CO—, alkyl—CO—, and other carbon or nitrogen attached homo or heterocyclic rings (preferably 5–7 membered, especially 5-membered and particularly preferably dithiacyclopentanes and derivatives thereof), e.g.

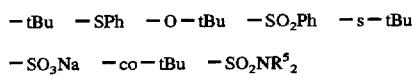

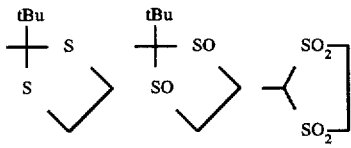

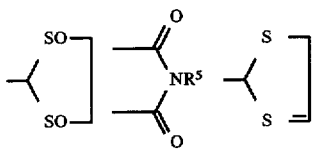

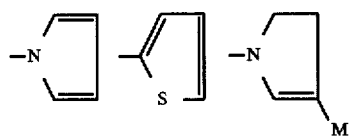

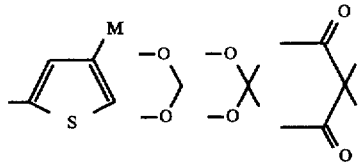

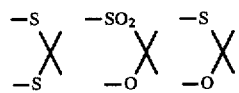

Thus exemplary phenoxy structures include the following

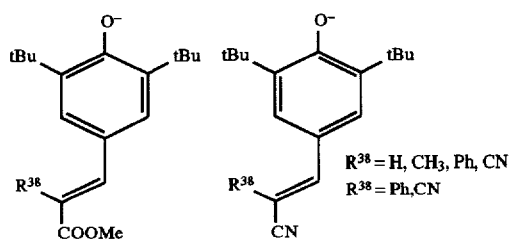

-continued

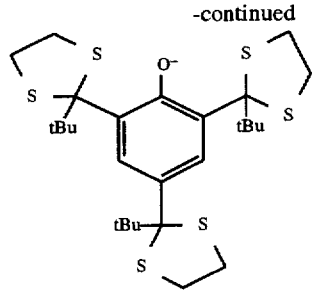

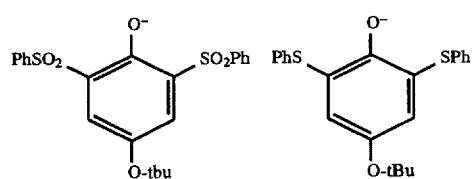

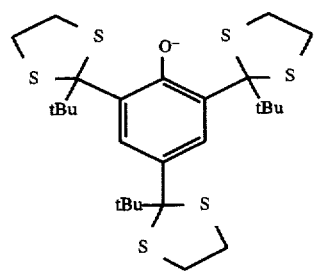

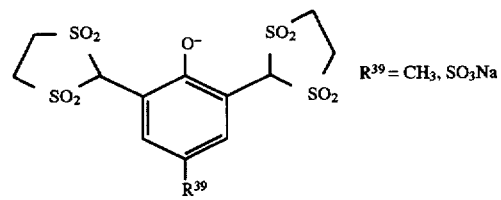

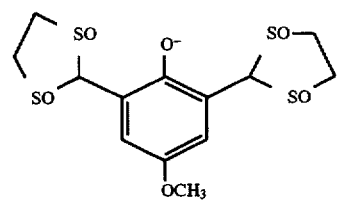

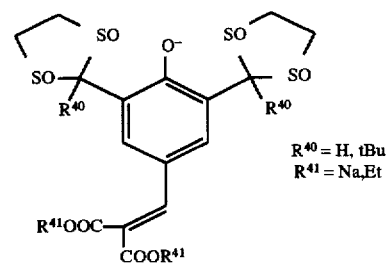

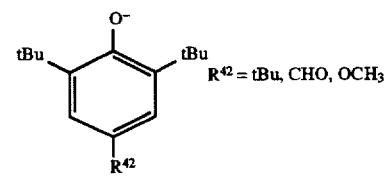

-continued

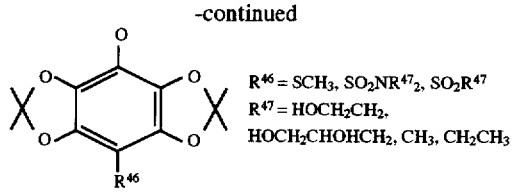

$R^{46}$ = SCH$_3$, SO$_2$NR$^{47}_2$, SO$_2$R$^{47}$
$R^{47}$ = HOCH$_2$CH$_2$,
HOCH$_2$CHOHCH$_2$, CH$_3$, CH$_2$CH$_3$

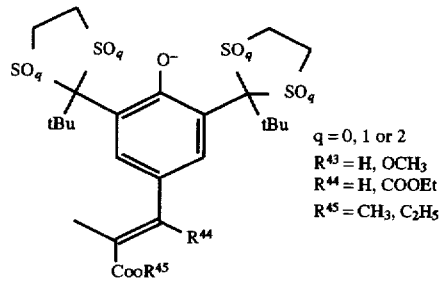

q = 0, 1 or 2
$R^{43}$ = H, OCH$_3$
$R^{44}$ = H, COOEt
$R^{45}$ = CH$_3$, C$_2$H$_5$

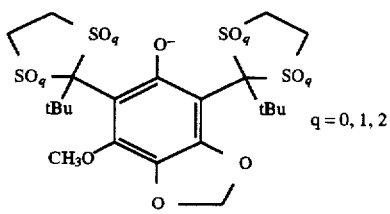

q = 0, 1, 2

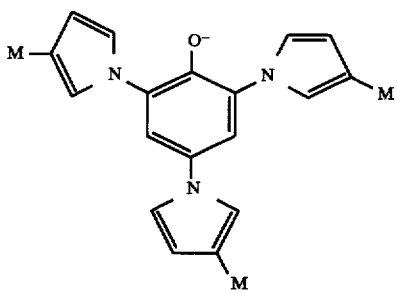

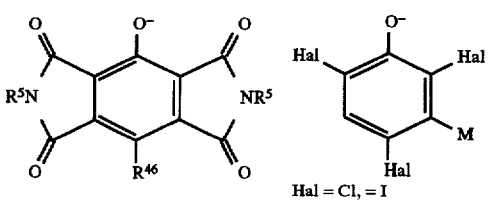

Hal = Cl, = I

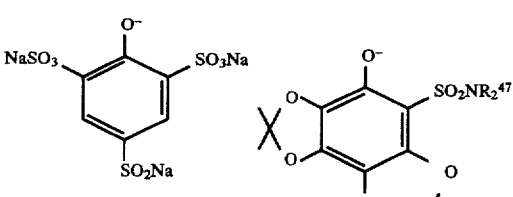

Indolizinyl:

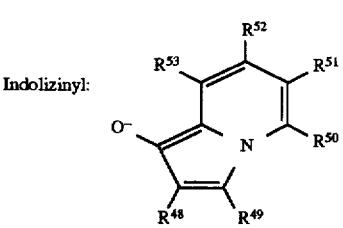

where $R^{52}$ is an electron withdrawing group (e.g. a cyano or carboxyl group or an amide or ester thereof, e.g. a group COOR$^{54}$ or CONR$_2^{54}$ where $R^{54}$ is hydrogen or optionally hydroxylated, alkoxylated or aminated alkyl) or, less preferably, a steric hindrance or solubilizing group, e.g. $R^{31}$ or M;

each of $R^{48}$, $R^{49}$, $R^{50}$, $R^{51}$ and $R^{53}$ is a hydrogen or a steric hindrance or solubilizing group (e.g. $R^{31}$ or M), $R^{50}$ preferably being hydrogen and the remaining preferably being other than hydrogen, especially $R^{48}$ and $R^{49}$ which particularly preferably represent steric hindrance groups such as —S—tBu, —O—tBu etc.

In a preferred embodiment each of the groups $R^{50}$, $R^{51}$ and $R^{53}$, which may be the same or different, independently represents a hydrogen atom, a hydroxy group or an optionally hydroxylated optionally alkoxylated alkyl, alkoxy, alkylthio or acyloxy group or a water solubilising group M; $R^{52}$ represents an electron withdrawing group, a sulphone or sulphonamide group (e.g. SO$_2$R$^{54}$, SO$_2$NR$_2^{54}$) or a group as defined for $R^{50}$ with the exception of hydrogen;

each of the groups $R^{48}$ and $R^{49}$ independently represents a hydrogen atom, a water solubilising group M or an alkyl, alkoxy, alkylthio, acyloxy or aryl group optionally substituted by alkyl, hydroxy, mercapto, alkoxy or optionally alkoxylated, optionally hydroxylated acyloxy groups, or by a water solubilising group M;

or adjacent groups $R^{48}$ and $R^{49}$, $R^{50}$ and $R^{51}$, $R^{51}$ and $R^{52}$ and/or $R^{52}$ and $R^{53}$, together with the two intervening carbon atoms may represent groups of formula

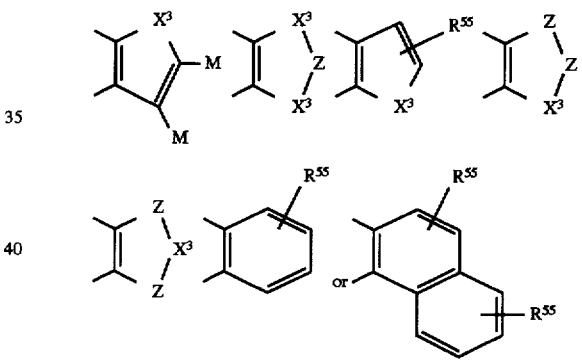

where $R^7$ represents a hydrogen atom, a hydroxy, or optionally hydroxylated, optionally alkoxylated acyloxy group or a water solubilising group M.

Preferred indolizinyl radicals include those wherein $R^{52}$ is an electron withdrawing group, especially an ester or amide or a carboxy group or a salt thereof. Preferably also $R^{48}$ and $R^{49}$ are identical, and particularly preferably $R^{48}$ and $R^{49}$ are both solubilizing groups M or optionally substituted alkoxy or alkylthio groups.

More preferably $R^{52}$ and one of $R^{50}$, $R^{51}$ and $R^{53}$ are alkoxy groups or a group —COOR$^{54}$, —OCOR$^{54}$, —CONHR$^{54}$ or —CONR$^{54}_2$, e.g. —CON(CH$_2$CH$_2$OH)$_2$.

Examples of particularly preferred identities for $R^{48}$ to $R^{53}$ are as follows:

for $R^{53}$: hydrogen, methoxy and carboxy and salts, esters and amides thereof for $R^{52}$: cyano, carboxy and salts, esters and amides thereof for $R^{51}$: hydrogen, methoxy and carboxy and salts, esters and amides thereof for $R^{50}$: hydrogen, methoxy, tri(hydroxymethyl)methylthio and carboxy and salts, esters and amides thereof for $R^{50}$ and $R^{51}$ together: dimethyl methylenedioxy and di(hydroxymethyl)methylenedioxy for $R^{48}$ and $R^{49}$: phenyl, t-butoxy, t-butylthio, carboxymethylthio, 3,4-dihydroxybutanoyloxy, 2,3-dihydroxypropoxycarbonyl, 2-sulphoethylthio, tri(hydroxymethyl)methyl, bis 2-hydroxyethyl carbamoyl and bis (2,3-dihydroxypropyl)carbamoyl for $R^{48}$ and $R^{49}$ together: dimethylmethylenedioxy and di(hydroxymethyl)methylenedioxy.

Particularly preferred indolizinyl radicals for use in accordance with the invention include

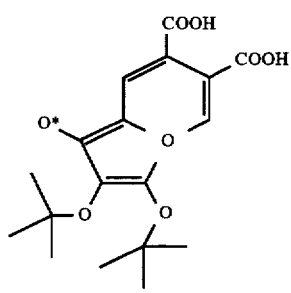

2,3-di-t-butoxy-6,7-dicarboxy-1-indolizinyl radical

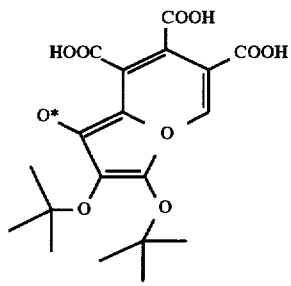

2,3-di-t-butoxy-6,7,8-tricarboxy-1-indolizinyl radical.

More preferred indolizinyl radicals include:

2,3-di-carboxymethylthio-6,7-dicarboxy-1-indolizinyl radical

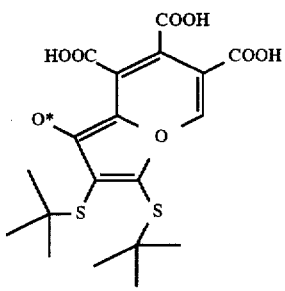

2,3-dibutylthio-6,7,8-tricarboxy-1-indolizinyl radical

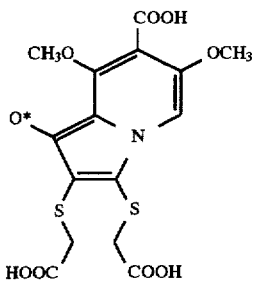

2,3-di-carboxymethylthio-7-carboxy-6,8dimethoxy-1-indolizinyl radical

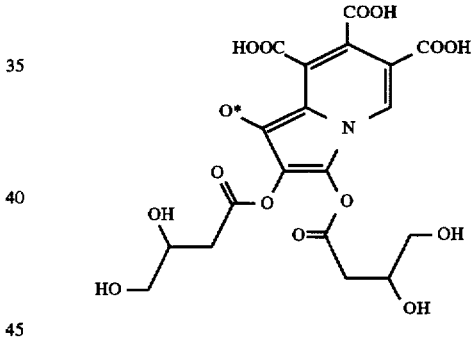

2,3-di[3,4-dihydroxybutanoyloxy]-6,7,8-tricarboxy-1-indolizinyl radical

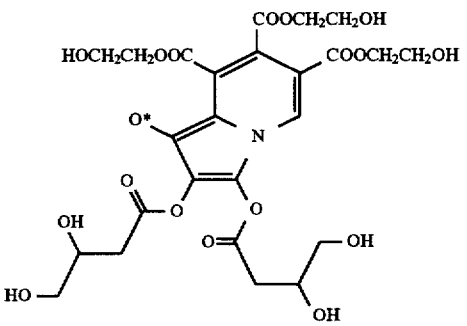

2,3-di[3,4-dihydroxybutanoyloxy]-6,7,8-tri[2-hydroxyethoxycarbonyl]-1-indolizinyl radical

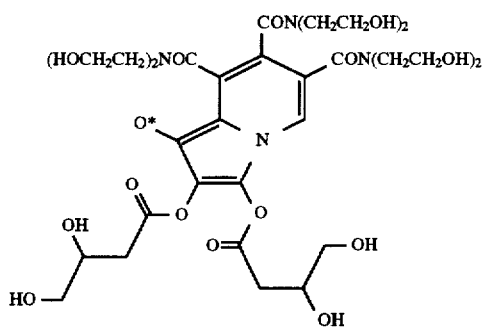

2,3-di-[3,4-dihydroxybutanoyloxy]-6,7,8-tri[di-(2-hydroxyethyl)amino carbonyl]-1-indolizinyl radical

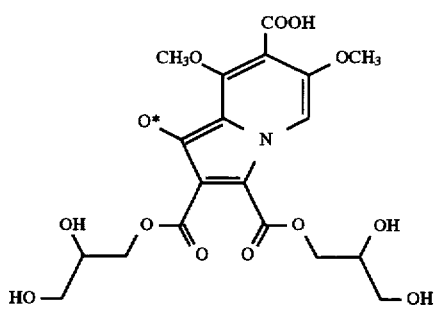

2,3-di[2,3-dihydroxypropoxycarbonyl]-7-carboxy-6,8-dimethoxy-1-indolizinyl radical

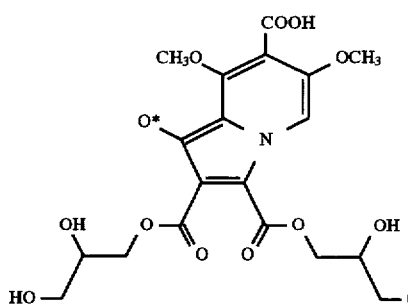

2,3-di[3-hydroxypropanoyloxy]-6,7,8-tricarboxy-1-indolizinyl radical.

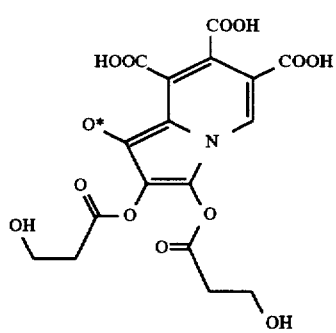

2,3-di[2-hydroxyethoxycarbonyl]7-carboxy-6,8-dimethoxy-1-indolizinyl radical 2,3-di[2-sulphoethylthio]-6,7,8-tricarboxy-1-indolizinyl radical

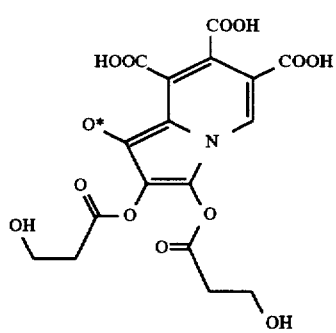

2,3-di[tri-hydroxymethyl)methyl-7-carboxy-6,8-dimethoxy-1-indolizinyl radical

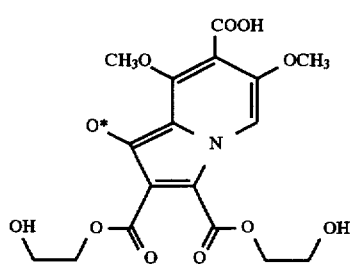

2,3-di[di-(2-hydroxyethyl)-aminocarbonyl]-6,7,8-tricarboxy-1-indolizinyl radical

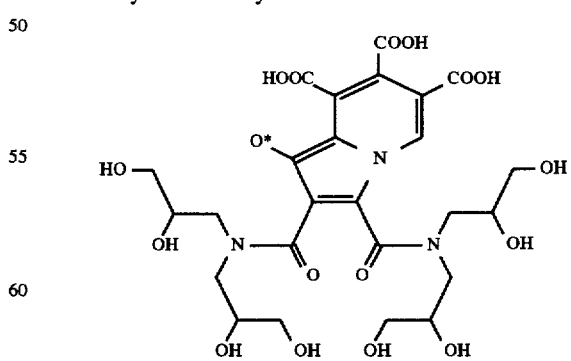

2,3-di-[di(2,3-dihydroxypropyl)amino carbonyl]-6,7,8-tricarboxy-1-indolizinyl radical as well as radicals of the general formulae

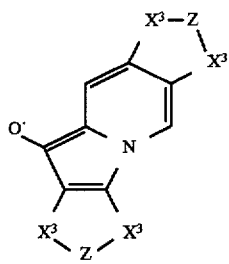

and

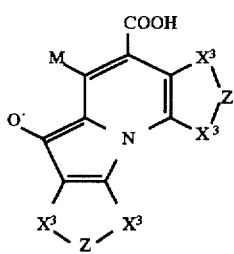

Indolizinyl radicals wherein $R^{53}$ and $R^{52}$ are carboxy groups and $R^{50}$ and $R^{51}$ together are dimethylmethylenedioxy or di(hydroxymehtyl)methylenedioxy groups or where $R^{53}$ and $R^{51}$ are methoxy groups, $R^{52}$ is a carboxy group and $R^{50}$ is a trihydroxymehtyl methylthio group are also preferred.

Examples of indolizinyl radicals include

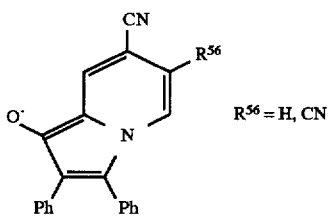

$R^{56}$ = H, CN

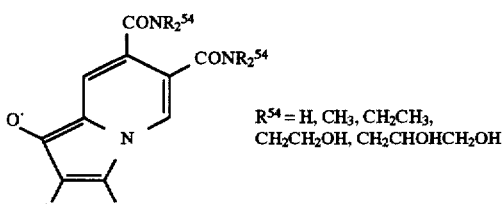

$R^{54}$ = H, CH$_3$, CH$_2$CH$_3$, CH$_2$CH$_2$OH, CH$_2$CHOHCH$_2$OH

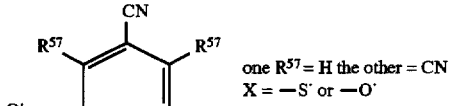

one $R^{57}$ = H the other = CN
X = —S· or —O·

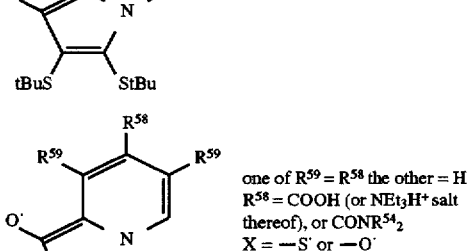

one of $R^{59}$ = $R^{58}$ the other = H
$R^{58}$ = COOH (or NEt$_3$H$^+$ salt thereof), or CONR$^{54}$$_2$
X = —S· or —O·

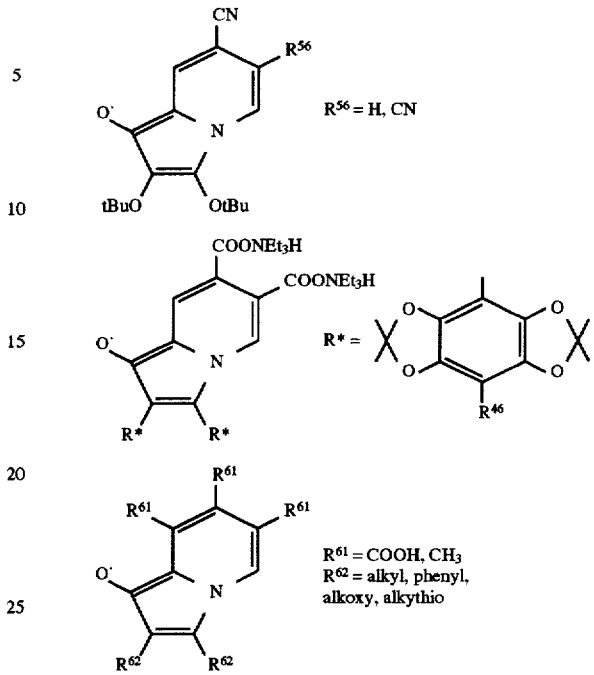

$R^{56}$ = H, CN $R^{61}$ = COOH, CH$_3$
$R^{62}$ = alkyl, phenyl, alkoxy, alkythio Most of the persistent indolizinyl radicals discussed above are themselves novel and they, their salts, and their non-radical precursors form further aspects of the invention. In particular the water-soluble compounds are all novel.

In particular the novel indolizinyl radicals include compounds wherein $R^{48}$ to $R^{53}$ are as hereinbefore defined with the proviso that where either one of $R^{53}$, $R^{52}$ or $R^{51}$ is cyano, or $R^{52}$ is —CHO, —CO$_2$CH$_3$, —CONH$_2$, or —COOH$_3$, and the remaining substituents $R^{50}$, $R^{51}$, $R^{52}$, $R^{53}$ are hydrogen, at least one of $R^{48}$ and $R^{49}$ is other than a substituted or unsubstituted phenyl group, and that where $R^{52}$ is cyano, and $R^{50}$, $R^{51}$, and $R^{53}$ are hydrogen, at least one of $R^{48}$ and $R^{49}$ is other than n—C$_3$H$_7$.

Indolyl:

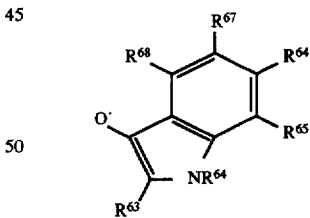

where $R^{65}$ to $R^{68}$ are hydrogen or more preferably steric hindrance, solubilizer or electron-withdrawing groups, e.g. $R^{31}$ or M: $R^{63}$ is a steric hindrance, solubilizer or a π-system extending group, e.g. $R^{31}$, M, carboxyl or an indolyl group (as with the dibenzoyl indigo structure); and $R^{64}$ is an acyl, e.g. PhCO, group or an alkyl group optionally substituted by solubilizing moieties, e.g. hydroxyl, amine, alkoxy, carboxy and sulphourea groups, for example by —CON (CH$_2$CH$_2$OH)$_2$ or —SO$_2$N(CH$_2$CHOHCH$_2$OH)$_2$ groups.

Thus $R^{65}$ to $R^{68}$ conveniently may represent bridging moieties of the type discussed above, e.g. —O—C(CH$_3$)$_2$—O— groups or t-butoxy or t-butylthio groups or one or two of $R^{66}$, $R^{67}$ and $R^{68}$ may conveniently represent SO$_3^-$ groups.

Examples of appropriate indolyl radicals include:

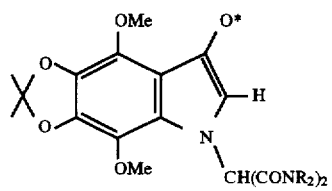

and

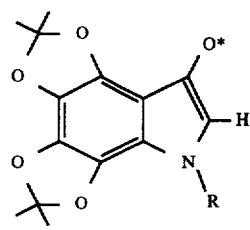

where R=CH$_2$CHOHCH$_2$OH or CH(CHOHCH$_2$OH)$_2$

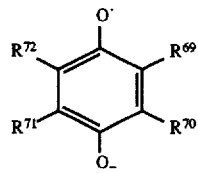

where R$^{69}$ to R$^{72}$ which may be the same or different represent steric hindrance and/or solubilizing groups or more preferably R$^{69}$ and R$^{70}$ and/or R$^{71}$ and R$^{72}$, together with the intervening carbons form fused aryl rings, preferably 5–7 membered rings, which optionally but preferably themselves carry steric hindrance and/or solubilizing (e.g. R$^{31}$ and M) groups. Particularly preferably, the mesomeric forms of the semiquinone anion radicals, i.e. O—B—O$^-$ and $^-$O—B—O (where B is used to represent the body of the molecule) are identical.

Examples of semiquinone anion radicals thus include

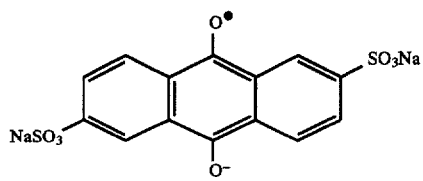

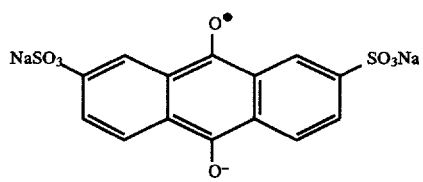

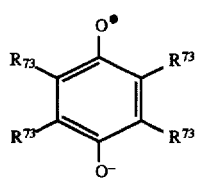

-continued
R$^{73}$ = OPh, StBu, SEt, SCH$_2$CH$_2$OH

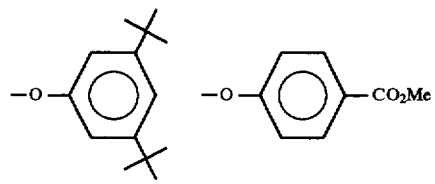

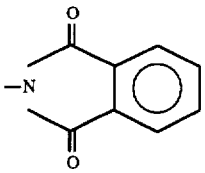

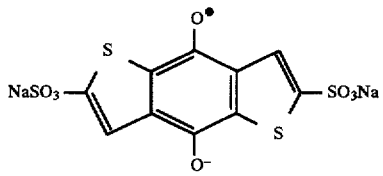

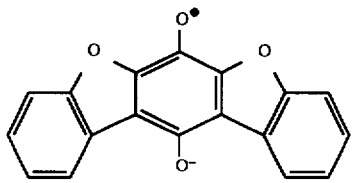

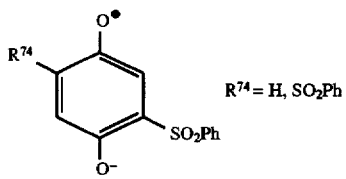

R$^{74}$ = H, SO$_2$Ph

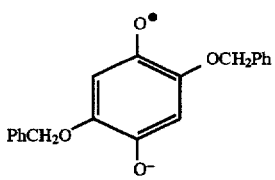

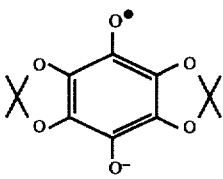

Galvinoxyl:

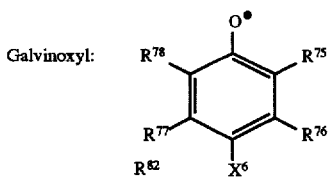

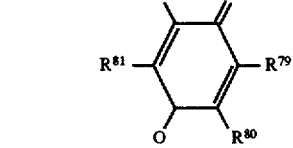

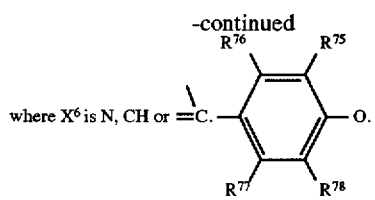

where $X^6$ is N, CH or =C.

each of $R^{75}$, $R^{78}$, $R^{80}$ and $R^{81}$ is a steric hindrance group (especially t-Butyl), optionally carrying a solubilizing moiety and each of $R^{76}$, $R^{77}$, $R^{79}$ and $R^{82}$ is hydrogen or a steric hindrance or solubilizing group or adjacent pairs of $R^{75}$ to $R^{82}$ may together represent bridging steric hindrance groups or fused aryl rings (optionally themselves carrying steric hindrance and/or solubilizing groups).

As examples of enolate radicals may be mentioned:

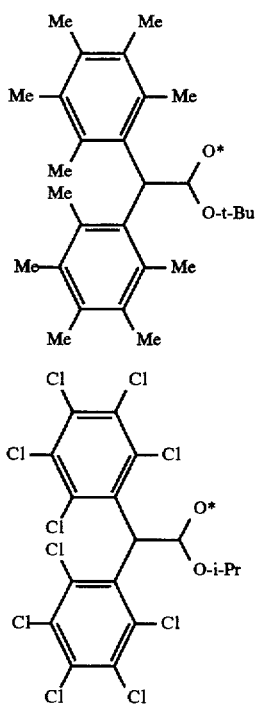

Such radicals are described in the literature, for example by O'Neill and Hagarty in J. Chem. Soc., Chem. Commun. 1987, 744 and J. Org. Chem. 52, 2115, 1987.

Generally speaking, substitution to enhance radical stability should be at or adjacent sites in the $X^1(C=C)_nX^2$ π-system which have high spin density. Substitution at high spin density sites should generally be with unreactive groups and frequently electron withdrawing or electron donor substituents will be preferred. Substitution at neighbouring sites should generally be by bulky steric hindrance groups which serve to prevent the radical from reacting with other molecules or radicals. The steric hindrance groups can also serve to enhance water solubility of the radical; alternatively separate solubilizing substituents may be included.

The particularly preferred substituent groups for the radicals for use according to the invention include the following —tBu, —O—tBu, —S—tBu, —OC(CH$_3$)$_2$—O—, I, —CO—CR$^7{}_2$—CO—, —CO—NR$^5$—CO—, —SO$_3$Na, —COOR$^2$, —S—R$^2$, —SO$_2$R$^2$, SO$_2$NR$^2{}_2$.

Persistent cyclic π-system radicals are widely known from the literature and ones suitable for use according to the invention may be prepared by the methods described in the literature. Substitution along the lines discussed above may be achieved using methods known from the literature or by using methods analogous to those discussed in PCT/EP91/00285. Examples of relevant literature references include Forrester et al "Organic chemistry of stable free radicals" Academic Press, London 1968, Tetrahedron 18:61 (19..), Berichte (1957) page 1634, Angew Chem. Int. (1984) page 447, Helvetica (1988) page 1665, JACS (1957) page 4439, Rosenblatt JACS 62:1092 (1940), Taube et al. Berichte 86:1036 (1953), Weygand et al. Berichte 90:1879 (1957), Dann et al. Berichte 93:2829 (1960), Sziki Berichte 62:1373 (1929), Moore J Org Chem 33:4019 (1968), Fieser et al. JACS 70:3165 (1948), Reynolds et al. Org. Synthesis 34:1 (1954); Fujita Tet. Lett (1975) page 1695, Akita J Pharm Soc. Japan 82:91 (1962), Graebbe J. für Praktische Chemie 62:32 (1900), Helferich et al. Annalen 551:235 (1942), Indian J. Chem. 12:893 (1974), Ramirez et al. JACS 81:4338 (1959), Ramirez et al. JOC 23:778 (1958), Stock et al. JACS 86:1761 (1964), Ramirez et al. JOC 33:20 (1968), Methoden der Organischen Chemie —Houben Weyl page 464–5, No. VII/3a (1977), Can J Chem 40:1235 (1962), Chem Lett (1984) page 341, JCS Perkins II (1989) page 1349, JACS (1960) page 6208, J Chem Phys (1965) page 308, JOC (1988) page 5770, McNab et al. JCS Perkins II (1988) page 759, Russell et al. JACS (1970) page 2762, Weiser et al. Tet. Lett. 30:6161, J Phys Chem 71:68 (1967), Dimroth et al. Liebigs Annalen 624:51 (1959), Miura et al. JOC 58:5770 (1988), Ata et al. Chem Lett (1989) 341–344, Solar JOC 28:2911 (1963), JOC 51:4639 (1986), JOC 54:3652 (1989), Theophil Eicher and Josef L Weber "Structure and Reactivity of Cyclopropenones and Triafulvenes" in Topics in Current Chemistry vol 57, Springer Verlag pages 1–109, Comprehensive Heterocyclic Chemistry Vol 4 part 3 Pergamon 1984 London, ISBN 0-08-030704-3, Chapter 3/08 Pyrroles with Fused Six-membered Heterocyclic Rings:(i) a-Fused, Pages 443–495; W. Flitsch Methods for the construction of the Indolizine Nucleus; Takane Uchida, Synthesis pages 209–236; Moria L. Bode and Perry T. Kaye: A New Synthesis of Indolizines via Thermal Cyclisation of 2-Pyridyl derivatives. JCS PERKIN TRANS I (1990) 2612–2613; K. Matsumoto and T. Uchida Synthesis (1978) 207–208; Esko Pohjala. Acta Chem Scand. B 28 (1974) p582–583, B 29 (1975) 1079–1084, B 30 (1976) 198–202, B 31 (1977) 321–324; Heterocycles (1974) 585–588; Heterocycles (1975) 615–618: J Heterocyclic Chem (1977) 273–279; J Heterocyclic Chem (1978) 955–960; D. H. Wadsworth et al J. Org Chem (1989) 3660–3664; Tet Lett. (1981) 3569–3572; J. Org Chem (1986) 4639–4644; J Org Chem (1989) 3652–3660; L. Cardellini et al. JCS PERKIN TRANS II (1990) 2177–2121; Tominaga et al. Heterocycles II (1990) page 477; JACS (1990) p 8100; Tet. Lett. (1990) pp. 5689, 7109 and 6949; JCS Perkin I (1990) p. 2612; J Het. Chem (1990) p 263: JCS Perkin I (1989) p. 1547; Bordwell JACS 113:3495 (1991); Chem Ber 93:2649 (1960); Chem Ber 87:922 (1954); Acta Chem Scand. 23:751 (1969); Chem Ber 42:2539 (1909); Becker et al. New J Chem 12:875 (1988).

Persistent free radicals which have relatively few transitions, e.g. less than 15, preferably less than 10, in their esr spectra and radicals having narrow linewidth esr transitions, e.g. up to 500 mG, preferably less than 150 mG, especially less than 60 mG and particularly less than 25 mG, are especially preferred for use as OMRI contrast agents. (The linewidths referred to are conveniently the intrinsic linewidths (full width at half maximum in the absorption spectrum) at ambient conditions).

Whilst low numbers of esr transition lines are generally preferred to obtain more effective coupling of the esr and NMR transitions, we have found that surprisingly good coupling, and therefore enhancement of the MR signal, may also be achieved with radicals showing a large number of ESR transitions.

Where the radicals have a multiplicity of esr transitions, the hyperfine splitting constant is preferably very small. In this connection radicals having as few as possible non-zero spin nuclei, positioned as far away as possible from the paramagnetic centre are thus especially preferred.

The novel radicals of the invention include radicals which surprisingly are stable at physiological pH, have long half lives (at least one minute, and preferably at least one hour), long relaxation times, and exhibit surprisingly good relaxivity. Water-soluble radicals are a particularly important aspect of the invention.

The radicals may be coupled to further molecules for example to lipophilic moieties such as long chain fatty acids or to macromolecules, such as polymers, proteins, polysaccharides (e.g. dextrans), polypeptides and polyethyleneimines. The macromolecule may be a tissue-specific biomolecule such as an antibody or a backbone polymer such as polylysine capable of carrying a number of independent radical groups which may itself be attached to a further macromolecule. Coupling to lipophilic groups is particularly useful since it may enhance the relaxivity of the radicals in certain systems such as blood. Such lipophilic and macromolecular derivatives of the radicals and salts thereof form a further aspect of the present invention.

The linkage of a radical to the further molecule may be effected by any of the conventional methods such as the carbodiimide method, the mixed anhydride procedure of Krejcarek et al. (see Biochemical and Biophysical Research Communications 77:581 (1977)), the cyclic anhydride method of Hnatowich et al. (see Science 220:613 (1983) and elsewhere), the backbone conjugation techniques of Meares et al. (see Anal. Biochem. 142:68 (1984) and elsewhere) and Schering (see EP-A-331616 for example) and by the use of linker molecules as described for example by Nycomed in WO-A-89/06979.

In view of their surprisingly beneficial properties, the novel radicals of the invention may also be used as esr spin labels in esr imaging or in magnetometry.

The radicals may be prepared from their non-radical precursor compounds by conventional radical generation methods for example comproportionation, oxidation, reduction or any of the other methods known from the literature or described in PCT/EP91/00285.

Thus in a-further aspect the invention provides a process for the preparation of the novel radicals of the invention which comprises subjecting a radical precursor therefor to a radical generation step and optionally subsequently modifying the substitution on the aryl moieties, e.g. by oxidation or reduction. By such modification for example, sulphide substituents (e.g. —$SCH_3$ or —$SCH_2COOEt$) may be oxidized to the corresponding sulphones so avoiding problems of acidic hydrogens prior to radical formulation. Similarly lipophilic substituents (such as —$SCH_2COOEt$) may be reduced to corresponding hydrophilic substituents (e.g. —$SCH_2CH_2OH$).

Thus for example carbon free radicals may conveniently be prepared from corresponding triaryl methyl halides by reduction with a metal catalyst, such as copper, zinc or silver, or by electrolytic reaction on an electrode or by photochemical reaction in the presence of a chlorine radical scavenger, e.g. an olefin. Alternatively, carbon free radicals may be prepared from the corresponding triaryl methanes by reaction with a base, e.g. in the presence of sodium hydride followed by a reaction with an oxidant, e.g. iodine in the presence of oxygen or a quinone such as chloranil, following for example the method described in U.S. Pat. No. 3,347, 941. Another method to prepare triarylmethyl radicals is to react triarylmethanes with other, less stable radicals such as tert-butoxyl radicals. The latter radicals are generated in situ via thermolysis or photolysis of an appropriate precursor, such as a peroxide or an azo compound. A further example of a method by which radical preparation may be effected is reaction of the corresponding triaryl methanols in the presence of an acid to form a carbonium ion followed by reduction to the free radical in the presence of a suitable reducing agent, such as metal ions e.g. $Cr^{2+}$, $Fe^{2+}$, or by electrochemical reduction. The carbon free radicals may also be generated by a comproportionation reaction between cations and anions of a corresponding radical precursor. In such a reaction an electron is exchanged between the anion and the cation, and two radicals are generated. Triarylmethyl radicals may thus be prepared by mixing together a triarylmethyl radical precursor cation with a corresponding anion. Triarylmethyl radicals may also be prepared by thermolysis or photolysis of a corresponding dimeric triarylmethyl structure, for example an azobistriarylmethyl or a bis (triarylmethylcarboxylic acid) peroxide. An alternative method of preparation of triarylmethyl radicals is the electrochemical decarboxylation of a triarylmethylcarboxylate.

While radicals with long half lives in aqueous solution, for example at least one hour, preferably ten days, more preferably fifty days and especially preferably at least one year are clearly particularly desirable for use in in vivo imaging, shorter lived inert free radicals may still be utilised in imaging (e.g. of inanimate samples) and these may particularly conveniently be prepared immediately preadministration.

The non-radical precursors may themselves be prepared by methods conventional in the art or analogous to those described in PCT/EP91/00285.

Taking as another illustrative example the indolizinyl radicals, these indolizinyl radicals may be generated from the corresponding indolizinols by oxidation under air or oxygen, or by using a chemical oxidant such as benzoquinone, iodine or chloranil. Oxidation under air or oxygen is preferred.

Oxidation may conveniently be effected during cyclization to form the indolizinyl skeleton, during work-up or even before or during administration.

The non-radical indolizinyl precursors may themselves be prepared by methods conventional in the art. Thus to form an indolizinol, a suitable cyclopropenone is conveniently reacted with an appropriately substituted pyridine, following for example the procedures described by Wadsworth et al in Tetrahedron lett. 22:3569 (1981) and J. Org. Chem 51:4639 (1986).

Further processes for the preparation of oxoindolizine and oxoindilizinium compounds, i.e. derivatives in the keto as opposed to enol form, which may be used as non-radical precursors are described in EP-A-68880 and U.S. Pat. No. 4,446,223.

Thus indolizinyl free radicals according to the invention may be prepared by following reaction schemes such as those suggested below:

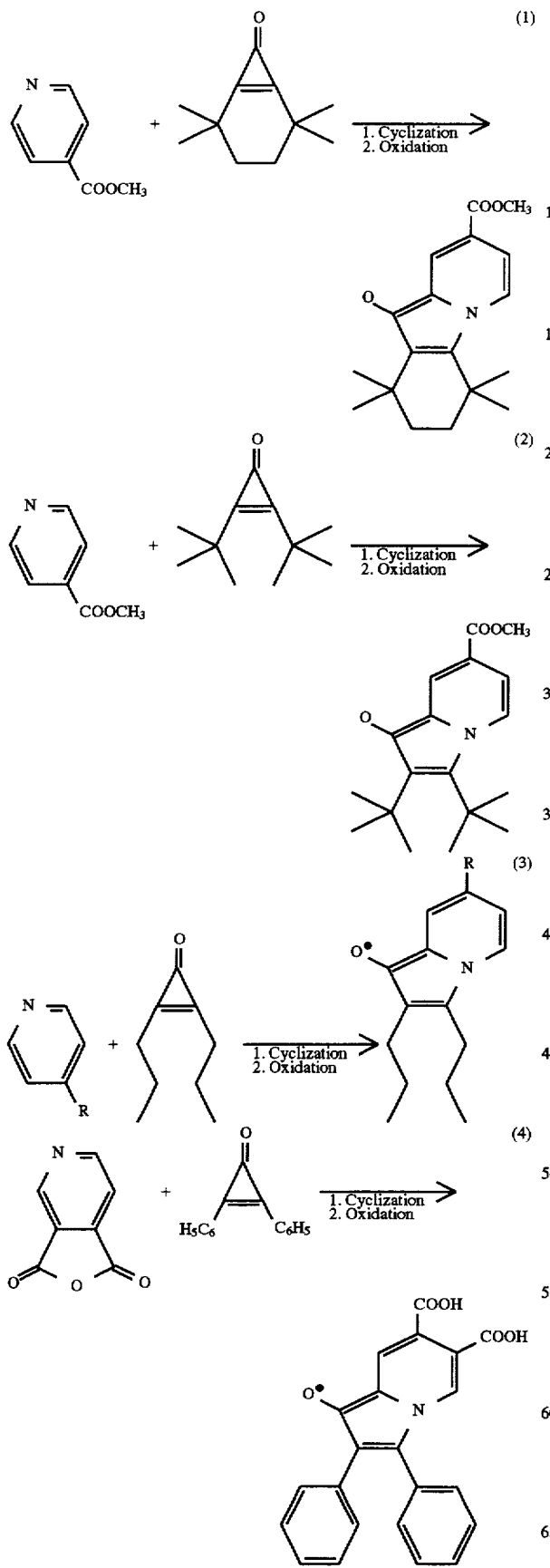

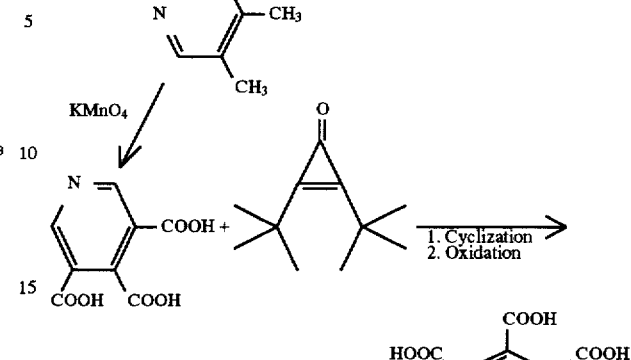

For the preparation of the non-radical precursors for indolizinyl radicals for use according to the invention, the literature contains many further useful guidelines. Thus one suitable approach for the production of nitro substituted precursors is described by Tominaya et al in J Heterocyclic Chem (1989) p. 477

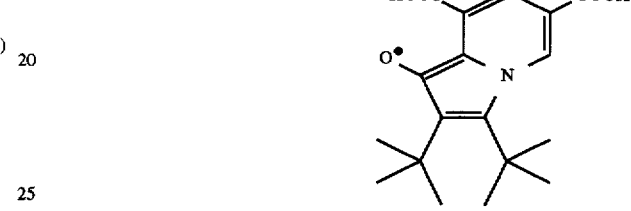

The nitro group can then be transformed into an oxygen radical, e.g. folowing the sequence:

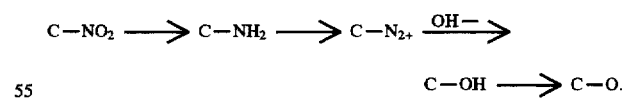

Hydrogenated indolizinyls, for instance indolizinyl alkaloids like castanospermine or similar substances also represent useful reagents in the synthesis of the indolizinyl radicals. These hydrogenated substances can be dehydrogenated and/or dehydrated to the indolizinols/indolizinyls. (See J.A.C.S. 1990, 8100; Tet Lett 1990, 5689; Tet Lett 1990, 7109; Tet Lett 1990, 6949).

More specific routes to indolizinyl radicals include the following:

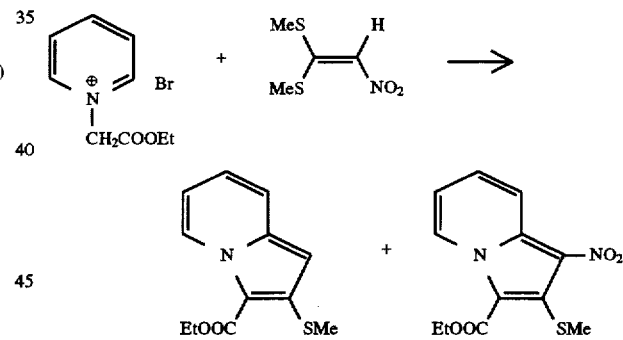

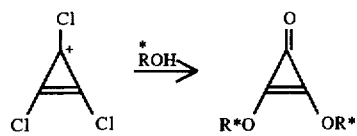

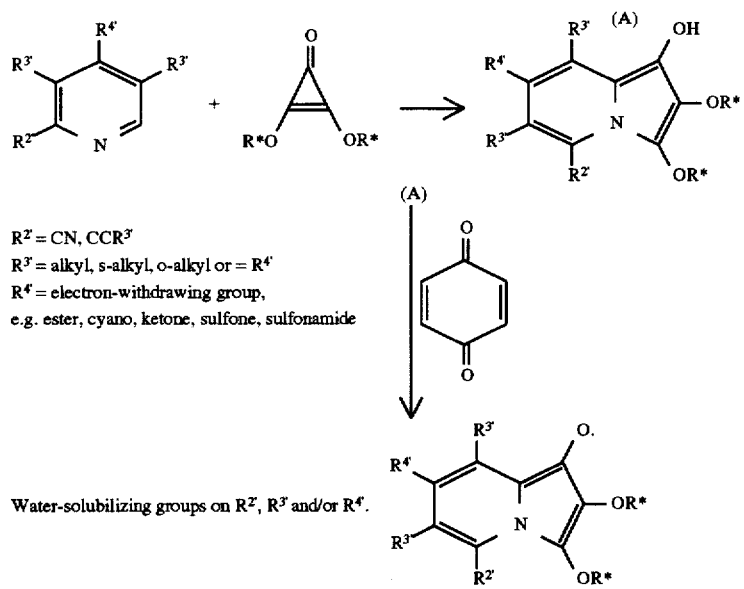

$R^{2'} = CN, CCR^{3'}$
$R^{3'} = $ alkyl, s-alkyl, o-alkyl or $= R^{4'}$
$R^{4'} = $ electron-withdrawing group,
e.g. ester, cyano, ketone, sulfone, sulfonamide Water-solubilizing groups on $R^{2'}$, $R^{3'}$ and/or $R^{4'}$.

For example

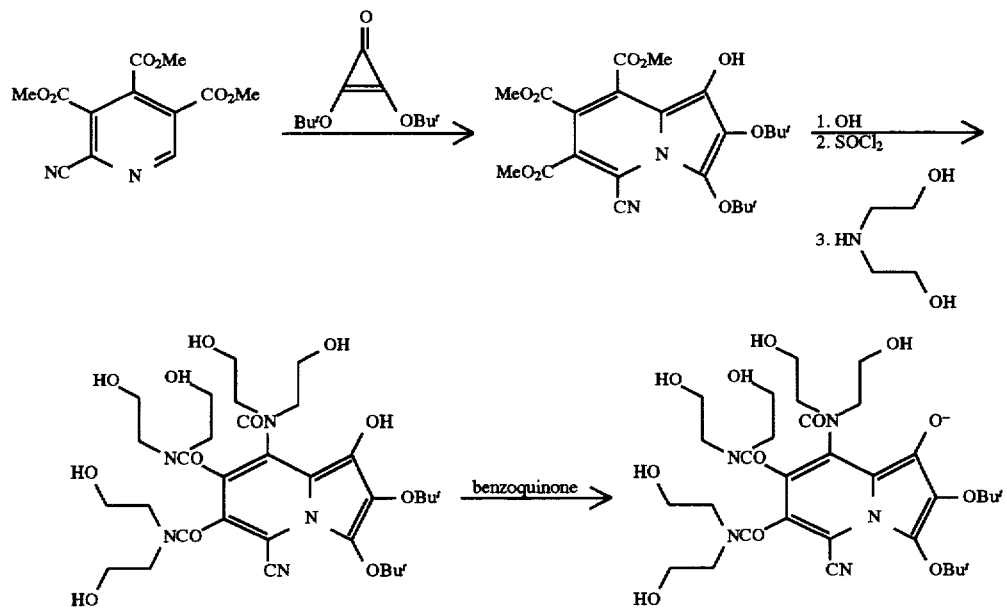

The preparation of semiquinone anion radicals is widely described in the literature. However, by way of illustration, aryloxy and semiquinone radicals can be prepared from quinones/hydroquinones according to the following general schemes:

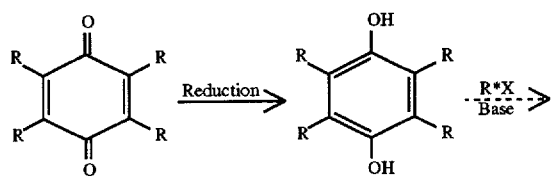

R*X = suitable alkylating agent, e.g. t-BuCl

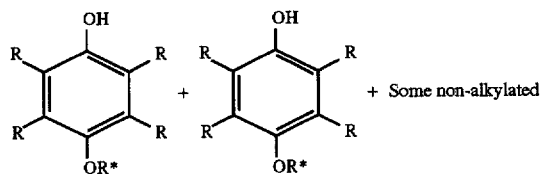

+ Some non-alkylated

If several products are formed, they can be separated by chromatography or crystallization, or by a combination of these techniques.

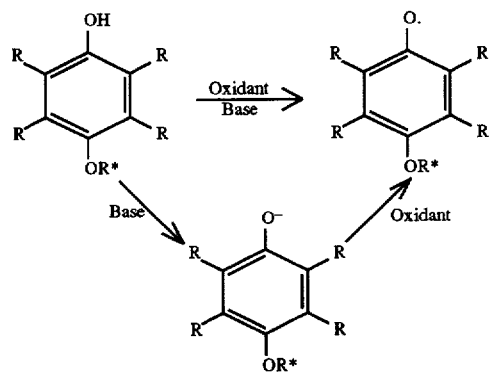

This group of alkoxyphenoxyl radicals is thus clearly related to the semiquinone anion radicals, the only difference being the R* instead of the minus charge, i.e.

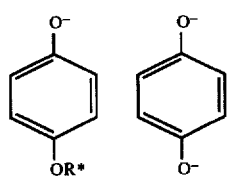

Where a monoalkylated product is desired, in order to generate phenoxyl rather than semiquinone anion radicals, a quinone starting material should be reduced to the hydroquinone form before the alkylation is effected. Suitable reduction techniques are described for example by E. F. Rosenblatt JACS 62, 1940 p 1092; H. J. Taube et al. Berichte 86, 1953, p 1036; F. W. Weygand et al. Berichte 90, 1957, p 1879; O. Daun et al. Berichte 93, 1960, p 2829; T. Sziki, Berichte 62, 1929, p 1373; H. W. Moore, J. Org. Chem. 33, 1968, p 4019; L. Feiser et al. JACS 70, 1948, p 3165; G. A. Reynolds et al., Organic Synthesis 34, 1954, p 1; T. Akita, J. Pharm. Soc. Jpn. 82, 1962, p 91; S. Fujita et al., Tet Lett, 1975, p 1965; and C. Graebbe, Journal für Praktische Chemie [2], 62, 1900, p 32.

Moreover using sodium borohydride, a whole range of quinones may be reduced to semiquinone anion radicals and, with more than one equivalent of H⁻, further reduction to hydroquinones is observed. An example is given below.

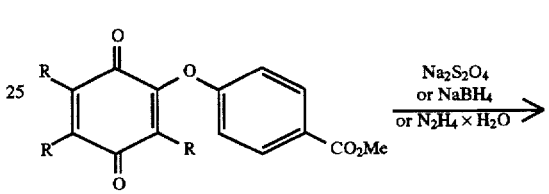

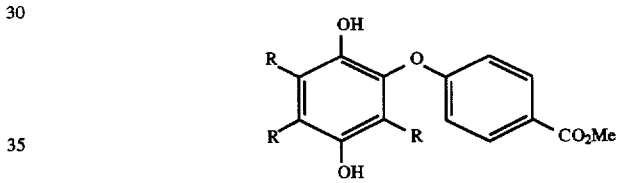

Other examples of quinone reductions useful for the preparation of radical precursors include

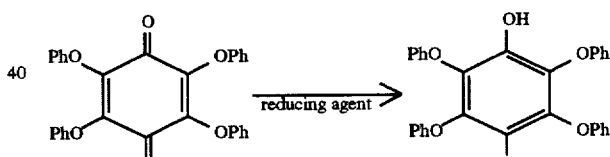

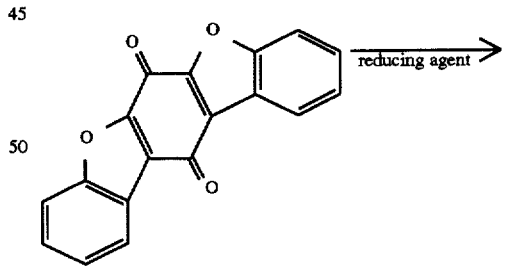

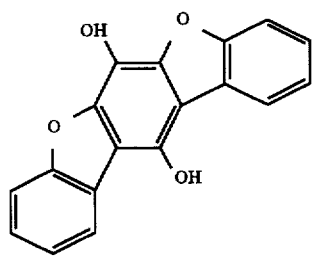

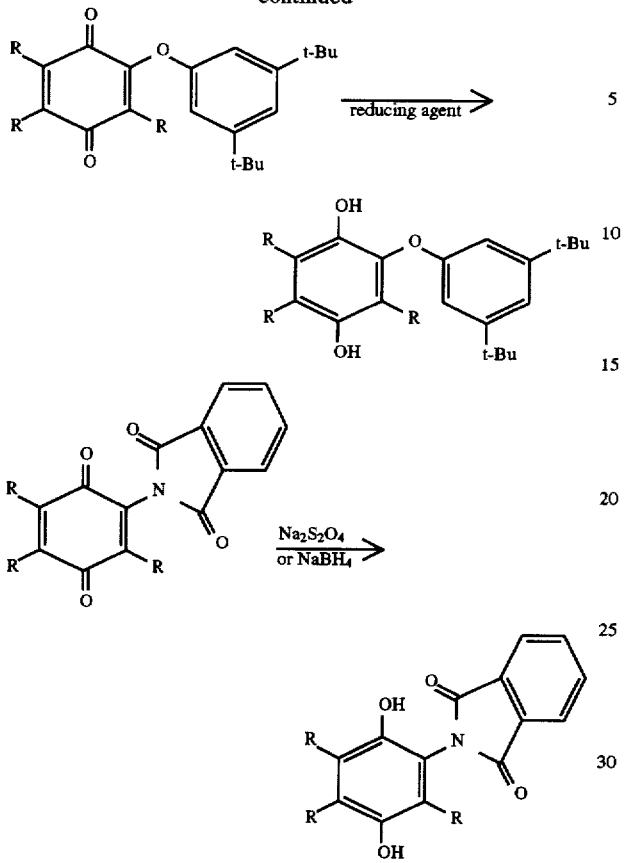

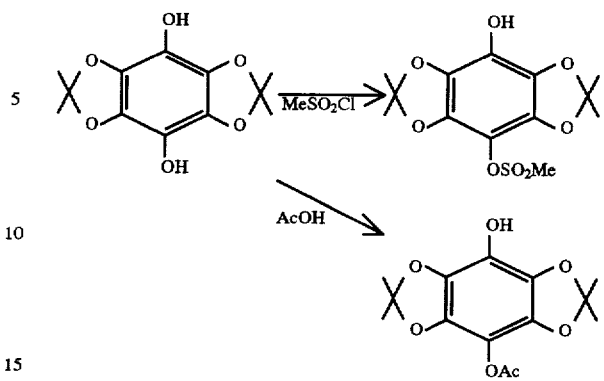

(In these formulae the R groups will generally be identical to the specifically identified substituents at the 2-positions).

General methods for alkylation of phenols/hydroquinones can be found in Compendium of Organic Synthetic Methods Vol. I–V by Harrison and Harrison and later by Hegedus and Wade, Wiley Interscience.

Compounds of formula

may be made either from diacylated hydroquinone by mild hydrolysis of one acyl group or by selective monoacylations.

In general, phenoxy radical precursors of formulae

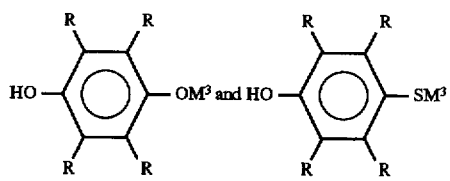

(where $M^3$ represents a group which makes the molecule water soluble) are desirable and may be made in this fashion, for example according to a scheme such as:

Other phenol/quinone substitutions are described for example in:

F Ramirez et al JACS 81, 1959, p 4338;
F Ramirez et al JOC 23, 1958, p 778;
G Stork et al JACS 86, 1964, p 1761; and
F Ramirez et al JOC 33, 1968, p 20.

In synthesising substituted radicals, the substituents may be introduced onto individual component substructures before they are put together to form the radical precursor compounds, or they may be introduced directly onto the precursor compound or the actual radical itself. It is also possible to effect the substitution and radical construction steps simultaneously in a "one-pot" reaction.

For use in OMRI, the radicals are conveniently formulated into contrast media together with conventional pharmaceutical carriers or excipients. Contrast media manufactured or used according to this invention may contain, besides the radicals (or the non-radical precursor where radical formation is to be effected immediately before administration), formulation aids such as are conventional for therapeutic and diagnostic compositions in human or veterinary medicine. Thus the media may for example include solubilizing agents, emulsifiers, viscosity enhancers, buffers, etc. The media may be in forms suitable for parenteral (e.g. intravenous) or enteral (e.g. oral) application, for example for application directly into body cavities having external voidance ducts (such as the gastrointestinal tract, the bladder and the uterus), or for injection or infusion into the systemic vasculature. However, solutions, suspensions and dispersions in physiologically tolerable media will generally be preferred.

Free radicals which are relatively unstable or insoluble in the sample environment may be encapsulated, e.g. in gastric juice resistant capsules containing a medium in which they are stable. Alternatively, the radicals may be presented as an encapsulated freeze dried powder in a soluble capsule. Such formulations might conveniently be dissolved shortly before in vivo use.

For use in in vivo diagnostic imaging, the medium, which preferably will be substantially isotonic, may conveniently be administered at a concentration sufficient to yield a 1 micromolar to 10 mM concentration of the free radical in the imaging zone; however the precise concentration and dosage will of course depend upon a range of factors such as toxicity, the organ targetting ability of the contrast agent, and the administration route. The optimum concentration for the free radical represents a balance between various factors. In general, optimum concentrations would in most cases lie in the range 0.1 to 100 mM, especially 0.2 to 10 mM, more especially 0.5 to 5 mM. Compositions for intravenous administration would preferably contain the free radical in concentrations of 10 to 1000 mM especially 50 to 500 mM. For ionic materials, the concentration will particularly preferably be in the range 50 to 200 mM, especially 130 to 170 mM and for non-ionic materials 200 to 400 mM, especially 290 to 330 mM. For imaging of the urinary tract or the renal or biliary system however, compositions may perhaps be used having concentrations of for example 10 to 100 mM for ionic or 20 to 200 mM for non-ionic materials. Moreover for bolus injection the concentration may conveniently be 0.1 to 100 mM, preferably 5 to 25 mM, especially preferably 6 to 15 mM.

The present invention will now be further illustrated by the following non-limiting Examples (percentages, parts and ratios are by weight and temperatures are in degrees Celsius unless otherwise stated).

EXAMPLE 1

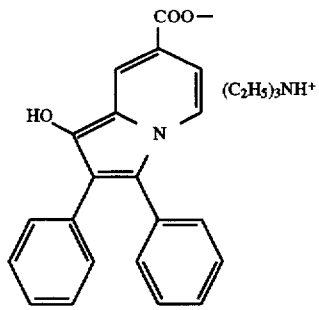

2,3-Diphenyl-1-hydroxyindolizine-7-carboxylate triethylammonium salt

Diphenylcyclopropenone (Aldrich 17,737-7) (0.5000 g 2.424*10$^{-3}$ mole) and isonicotinic acid (Aldrich I-1,750-8) (0.2985 g 2.424*10$^{-3}$ mole) were added in solid form to a carefully dried reaction flask. The flask was equipped with a septum and the flask was evacuated three times with addition of nitrogen after each evacuation. Chlorobenzene (Aldrich 27,064-4) (5 ml) was added with a gastight syringe. The stirred mixture was cooled to 0° C. Triethylamine (Aldrich 23,962-3) (0.3379 ml, 2.42*10$^{-3}$ mole) was added dropwise with a gastight syringe. The resulting mixture was stirred at ambient temperature for 2 days. The colour of the mixture changed to yellow and then to green. The solvent was removed on a rotavap, and the resulting semisolid was redissolved in hot ethanol and water. After cooling to ambient temperature, the product was filtered and washed with diethylether and dried in vacuum. All these operations were performed under an atmosphere of N$_2$.

Yield: 0.653 g (1.517*10$^{-3}$ mole)=62.6% of theory $^1$H NMR (250 MHz) (DMSO$_{d6}$D$_2$O with sodium hydrosulphite (Aldrich 15,795-3) present)) (water resonance at 4.60 ppm as reference) δ: 1.10 (t, 9H), 2.98 (q, 6H), 6.70 (d, 1H, H6, J$_{H6-H5}$, 7.56 Hz), 7.1–7.2 (m) and 7.25–7.35 (m) (total 10H, 2 Ph), 7.70 (d, 1H, H$_5$, J$_{H5-H6}$, 7.56 Hz), 8.04 (bs, 1H, H8).

MS (DEI) (DCI probe and electron impact ionization) M/Z: 329 (10%), 178 (8%), 86 (100%)

EXAMPLE 2

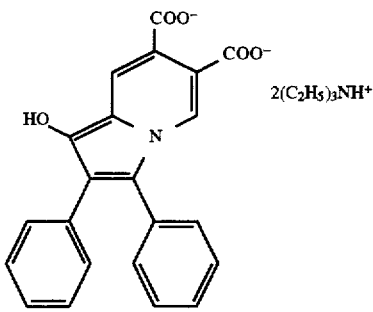

2,3-Diphenyl-1-hydroxyindolizine-6,7-dicarboxylate di-triethylammonium salt

Diphenylcyclopropenone (0.5000 g, 2.424*10$^{-3}$ mole) and pyridine-3,4-dicarboxylic acid (0.4051 g, 2.424*10$^{-3}$ mole) were added to a carefully dried reaction flask. The flask was equipped with a septum and evacuated three times with addition of nitrogen after each evacuation. Methanol (10 ml) (degassed with N$_2$) was added and the stirred slurry cooled to 0° C. Triethylamine (0.666 ml, 6.20*10$^{-3}$ mole) was then added with a syringe. The reaction mixture was stirred for 3 days at ambient temperature. (Thin layer chromatography showed complete conversion after one day). The yellowish product was filtered (under nitrogen to prevent radical formation) and washed with diethyl ether and dried at high vacuum. $^1$H NMR in D$_2$O/DMSO$_{d6}$ showed only ethyl resonances, upon addition of sodium hydrosulphite the resonances from the heterocycle appeared.

Yield: 0.762 g (1.3235*10$^{-3}$ mole)=54.6% of theory $^1$H NMR (250 MHz) (D$_2$O/DMSO$_{d6}$, sodium hydrosulphite present) (water resonance at 4.60 ppm as reference) d: 3.12 (t, 18H), 4.99 (q, 12H) 9.16–9.30 (m) and 9.34–9.46 (m) (total 10H, 2 Ph), 10.42 (s, 1H, H5) and 10.59 (s, 1H, H8).

MS (DEI) M/Z 373 (5%), 355 (47%), 329 (100%)

EXAMPLE 3

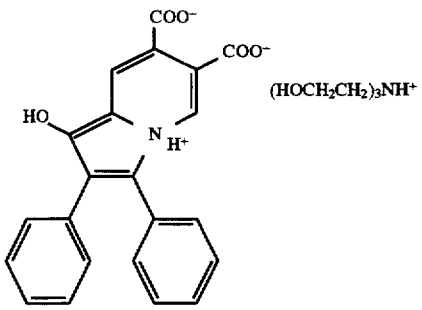

2,3-Diphenyl-1-hydroxyindolizine-6,7-dicarboxylate triethanolammonium salt

Diphenylcyclopropenone (0.5000 g, 2.424*10$^{-3}$ mole) and pyridine-3,4-dicarboxylic acid (0.4051 g, 2.424*10$^{-3}$ mole) were added to a carefully dried reaction flask. The flask was equipped with a septum and evacuated three times with addition of nitrogen after each evacuation. Methanol (10 ml) (degassed with N$_2$) was added with a gastight syringe and the stirred suspension cooled to 0° C. Triethanolamine (0.3217 ml, 2.424*10⁻³ mole) was added dropwise with a gastight syringe. The mixture was stirred for 48 hours at ambient temperature, cooled to about +10° C. and the product was isolated by filtration under N₂. The product was washed with a little cold methanol and ether on the filter and dried in vacuum.

Yield 0.548 g (1.0487*10⁻³ mole)=43% of theory

¹H NMR (250 MHz) (DMSO$_{d6}$/D₂O with sodium hydrosulphite present) (water resonance at 4.60 ppm as reference) d: 3.36 (t, CH₂, 6H), 3.82 (t, CH₂, 6H), 7.15–7.35 (m) and 7.40–7.50 (m) (total 10H, 2-Ph), 8.37 (s, 1H, H5) and 8.58 (s, 1H, H8).

MS (DEI) M/Z: 373 (11%), 355 (48%), 329 (100%) MS (Thermospray after RP 18 column, MeOH:H₂O 3:1 0.2M NH₄OAc) M/Z: 390 (M+18, 1%), 374 (M+1, 1%), 344 (17%), 330 (34%).

EXAMPLE 4

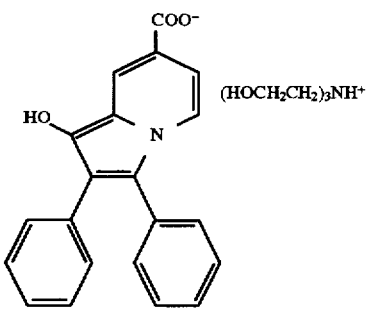

2,3-Diphenyl-1-hydroxyindolizine-7-carboxylate triethanolammonium salt

Diphenylcyclopropenone (0.6249 g, 3.03*10⁻³ mole) and isonicotinic acid (0.2985 g, 2.424*10⁻³ mole) were added to a carefully dried reaction flask. The flask was equipped with a septum and the flask was evacuated three times with addition of nitrogen after each evacuation. Methanol (19 ml) was added with a gastight syringe. The stirred suspension (slightly yellowish) was cooled to 0° C. Triethanolamine (Aldrich T5,830-0) (0.3217 ml, 2.424*10⁻³ mole) was added dropwise with a gastight syringe. The suspension went into solution immediately and an orange colour appeared. The reaction mixture was stirred at ambient temperature for 2.5 hours, while the title compound precipitated. The mixture was cooled to about 0° C. and the product isolated by filtration under N₂. The product was washed with minute amounts of methanol and some diethylether and dried.

Yield: 0.246 g (5.151*10⁻⁴ mole)=17% of theory

The product was identified by mass spectrometry; DCI probe and electron impact conditions identified the heterocyclic part and ¹H NMR identified the ammonium part. The product was further characterized by ESR and OMRI, measurements of the corresponding radical which was generated by treatment with oxygen.

MS (DEI) M/Z: 329 (97%), 178 (100%)

EXAMPLE 5

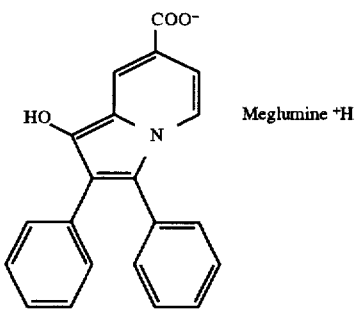

2,3-Diphenyl-1-hydroxyindolizine-7-carboxylate N-methylglucammonium salt

Diphenylcyclopropenone (0.500 g, 2.424*10⁻³ mole), isonicotinic acid (0.2985 g, 2.424*10⁻³ mole) and N-methylglucamine (0.473 g 2.424*10⁻³ mole) were added to a carefully dried reaction flask. The flask was equipped with a septum and was evacuated three times with addition of nitrogen after each evaporation. Tetrahydrofuran (10 ml, degassed with helium) was added with a gastight syringe. A yellow colour formation is observed immediately. The colour changed to black and all solids dissolved over a period of 18 hours. The product was precipitated by addition of petroleum ether (10 ml, 30°–60° C.—degassed with N₂). The yellow/green (indolizinol/indolizinyl) product was filtered under N₂ and washed with small amounts of tetrahydrofuran and petrol ether. More solids formed in the filtration flask and were also collected. The products were identified as the title compound based on mass spectrometry and ESR/OMRI measurements.

Yield: 0.105 g (2.002*10⁻⁴ mole)=8.3% of theory

MS (DEI) M/Z: 329 (100%), 178 (100%)

EXAMPLE 6

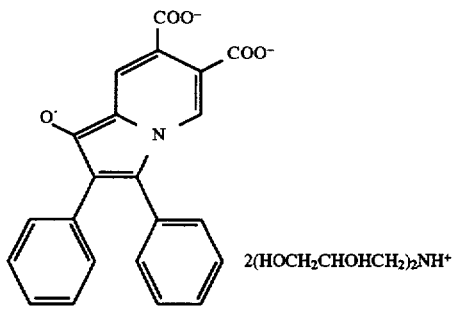

2,3-Diphenyl-1-hydroxyindolizin-6,7-dicarboxylate di-dipropan-2,3-diol ammonium radical salt. In situ formation of the radical 3,4-Pyridinedicarboxylic acid (2.424*10⁻³ mole, 0.4051 g), diphenylcyclopropenone (2.424*10⁻³ mole, 0.5000 g) and di(propane-2,3-diol) amine (4.848*10⁻³ mole, 0.8008 g) were stirred in methanol (10 ml), under an atmosphere of air for 24 hours at ambient temperature. Thin layer chromatography revealed complete consumption of the cyclopropenone and the solvent was removed on high vacuum, yielding the product as a foam. The radical was identified by mass spectrometry (DCI-EI and thermospray) and by the ESR spectrum and the OMRI effect in a water solution (buffer pH 7.4).

EXAMPLE 7

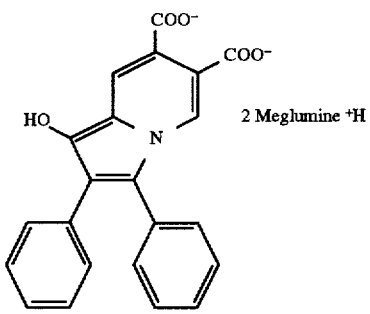

2,3-Diphenyl-1-hydroxyindolizin-6,7-dicarboxylate di-N-methylglucammonium salt 3,4-Pyridinedicarboxylic acid ($2.424*10^{-3}$ mole, 0.4051 g), diphenylcyclopropenone ($2.424*10^{-3}$ mole, 0.5000 g) and N-methylglucamine ($4.848*10^{-3}$ mole, 0.9404 g) were stirred in a mixture of tetrahydrofuran (10 ml, degassed with helium) and methanol (3 ml, degassed with helium) at ambient temperature for 24 hours. The solvent was removed and the product triturated with diethyl ether and methanol and dried.

Yield: 0.870 g ($1.139*10^{-3}$ mole)=47% of theory

MS (DCI) M/Z: 373 (5%), 329 (100%), 178 (71%)

EXAMPLE 8

Radical formation

The compounds of Examples 1 to 5 and 7 are converted to their radicals by oxidation in air or with benioquinone.

EXAMPLE 9

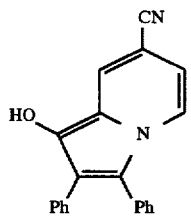

1-Hydroxy-2,3-diphenyl-7-cyanoindolizine

The title compound was synthesized according to the procedure of D H Wadsworth, J. Org. Chem., 1986, 51, 4639

Yield 0.184 g (0.59 mmol, 49%)

$^1$H NMR (300 MHz) (Acetone $D_6$) δ: 6.46 (dd, CH, 1H), 7.50–7.20 (m, 2-Ph, 10H), 7.90 (dd, CH, 1H), 8.01 (dd, CH, 1H)

MS (Thermospray via loop) M/Z: 310 (M+, 100%)

EXAMPLE 10

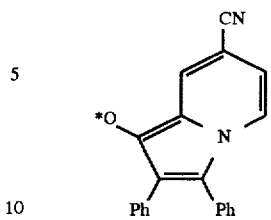

1-Oxy-2,3-dipehnyl-7-cyanoindolizinyl

The title compound was synthesized from the product of Example 9 according to the procedure of D. H. Wadsworth, J. Org. Chem., 1989, 54, 3652. The isolated green to black precipitate was analyzed by HPLC and the radical content was determined to be 20%.

OMRI signal enhancement at 5 Watts=60

EXAMPLE 11

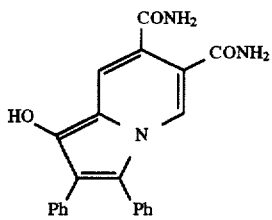

1-Hydroxy-2,3-diphenyl-6,7-diamidoindolizine

Diphenylcylcopropenone (0.250 g, 1.21 mmol) and 3,4-diamidopyridine (0.200 g, 1.21 mmol) were mixed in a dry, argon filled reaction flask. Chlorobenzene (2.5 mL) (oxygen free) was added, and the reaction was heated to 130° C. After 2 h the heating was stopped and the reaction was allowed to reach room temperature. Petroleum ether 40°–60° C. (2.5 mL) was added in order to obtain a complete precipitate of the product. The solvent was filtered off and the precipitate was washed with petroleum ether. Acetone (30 mL) was added to the crude product, and the mixture was stirred for 1 h. The dark acetone solution was filtered off leaving a yellow precipitate. The precipitate was analyzed by HPLC (Kromasil C8, $CH_3CN/H_2O$). Two peaks were found with a ratio of 2:1. HPLC-MS showed that the larger peak was the desired product.

Yield 0.155 g (0.418 mmol, 34%)

MS (Thermospray after HPLC C18) M/Z: 371 (M+, 12%), 356 (14%), 344 (17%), 326 (100%).

EXAMPLE 12

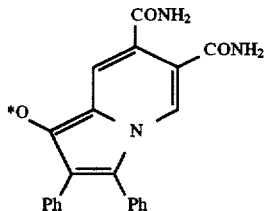

1-Oxy-2,3-diphenyl-6,7-diamidoindolizinyl

1-Hydroxy-2,3-diphenyl-6,7-diamidoindolizine (Example 11) was dissolved in THF and 4-benzoquinone was added. The reaction was stirred for 15 min at 50° C. The colour changed during the reaction from yellow to dark red. The product was analyzed and the formation of the radical was determined by an OMRI experiment.

OMRI signal enhancement at 5 Watts=70.

EXAMPLE 13

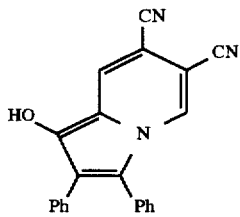

1-Hydroxy-2,3-diphenyl-6,7-dicyanoindolizine

Diphenylcyclopropenone (0.319 g, 1.55 mmol) and 3,4-dicyanopyridine (0.200 g, 1.55 mmol) were mixed in a dry, argon filled reaction flask. Chlorobenzene (2.5 mL) (oxygen free) was added, and the reaction was heated to 130° C. After 2 h the heating was stopped and the reaction was allowed to reach room temperature. Petroleum ether 40°–60° C. (2.5 mL) was added in order to obtain a complete precipitate of the product. The solvent was filtered off and the precipitate was washed with petroleum ether. The crude product was stirred with chloroform (30 mL) for 1 h. The dark chloroform solution was filtered off leaving the title product as a yellow precipitate.

Yield 0.100 g (0.298 mmol, 19%)

$^1$H NMR (300 MHz) (DMSO D$_6$) δ: 7.50–7.20 (m, 2-Ph, 10H), 8.29 (CH, 1H), 8.48 (CH, 1H)

MS (Thermospray via loop) M/Z: 359 (30%), 353 (45%), 337 (100%).

EXAMPLE 14

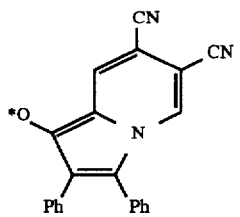

1-Oxy-2,3-diphenyl-6,7-dicyanoindolizinyl

1-Hydroxy-2,3-diphenyl-6,7-dicyanoindolizine (Example 13) (10 mg, 0.03 mmol) was dissolved in DMSO (5 mL) and 4-benzoquinone (13.0 mg, 0.12 mmol) was added. The reaction was stirred for 15 min at 70° C. The colour of the reaction became dark. The product was analyzed and the formation of the radical was determined by an OMRI experiment.

OMRI signal enhancement (5 Watts) 80.

EXAMPLE 15

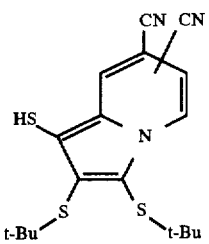

1-Mercapto-2,3-di-t-butylthio-7,8-dicyanoindolizine and 1-Mercapto-2,3-di-t-butylthio-6,7-dicyanoindolizine The title compounds are prepared according to the following reaction scheme

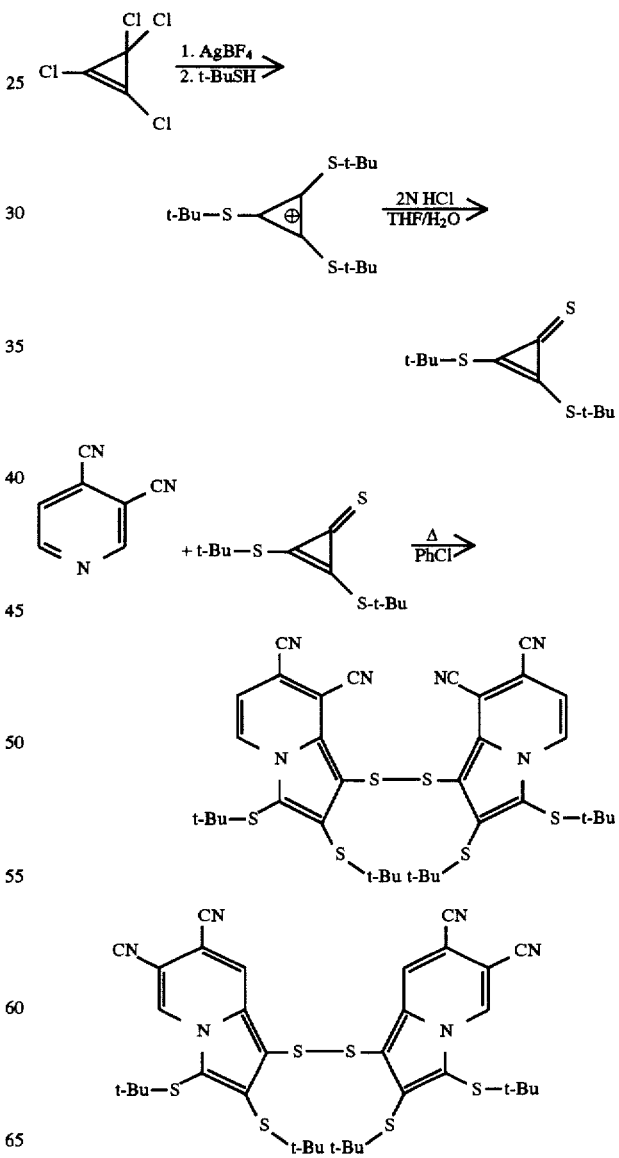

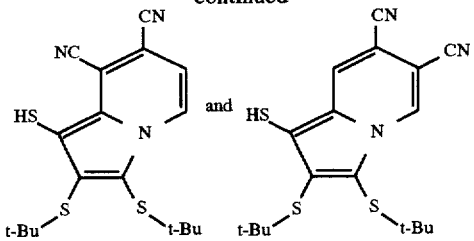

a) Bis(t-butylthio) cyclopropenethione

Silver tetrafluoroborate (21.8 g, 112 mmol) was dissolved in dry acetonitrile (50 mL) in a dry, argon filled reaction flask. The solution was cooled to −20° C. and tetrachlorocyclopropene (19.8 g, 11.0 mmol) dissolved in dry acetonitrile (25 mL) was added dropwise. When all was added the reaction was stirred for 0.5 h at −15° C. The temperature was lowered to −20° C. and t-BuOH (50.0 mL, 444.0 mmol) dissolved in dry acetonitrile was added. The reaction was allowed to reach room temperature and was stirred over night. The precipitated AgCl was filtered off and the filtrate was concentrated, almost to dryness. Chloroform and water were added, and after vigorous shaking, the water phase was discarded. The organic phase was dried over $Na_2SO_4$, filtered and evaporated. To the remaining crude product was added EtOAc (10 mL), and the mixture was stirred for 2 h. The dark oil transformed into yellow crystals (tris(t-butylthio)cyclopropenium tetrafluoroborate). The crystals were collected by filtration and were dissolved in a mixture of hydrochloric acid (50 mL, 2N) and THF (50 mL). The solution was refluxed for 4 h. After cooling to room temperature, chloroform (200 mL) was added. The organic phase was separated, washed once with water and dried over $Na_2SO_4$. The title compound was purified by flash-chromatography (DCM: Petroleum ether 40°–60° C. 1:1).

Yield 7.92 g (32.2 mmol, 29%)

$^1$H NMR (300 MHz) (CDCl$_3$) δ: 1.67 (s) $^{13}$C NMR (75 MHz) (CDCl$_3$) δ: 169.7, 154.9, 50.8, 32.2

MS (Electron impact ionization) M/Z: 247 (M+, 27%), 190 (35%), 134 (60%), 102 (14%), 59 (100%).

b) 1,1'-(2,2',3,3'-tetra-t-butylthio-7,7',8,8'-tetracyanodiindolizine)-disulfide and 1,1'-(2,2',3,3'-tetra-t-butylthio-6,6',7,7'-tetracyano-diindolizine)-disulfide Bis(t-butylthio)cyclopropenethione (0.382 g, 1.55 mmol) and 3,4-dicyanopyridine (0.200 g, 1.55 mmol) were mixed in a dry, argon filled reaction flask. Chlorobenzene (25 mL) (oxygen free) was added, and the reaction mixture was heated to 130° C. for 70 h. The reaction was stopped and the crude product was purified by flash-chromatography (DCM: petroleum ether 40°–60° C. 75:25). A mixture of the title homodimer compounds and the heterodimer disulfide was obtained (91 mg). On TLC all three appeared in the same spot (Rf. 0.21/ DCM: petroleum ether 40°–60° C. 75:25). The isomers were separated on HPLC (Kromasil KR100-10-C8, 250×10 mm, CH$_3$CN: H$_2$O 80:20).

Yield: 7,7',8,8' dimer 0.027 g (0.036 mmol, 4.6%) 6,6'7,7' dimer 0.009 g (0.012 mmol, 1.5%) hybrid dimer 0.028 g (0.036 mmol, 4.6%)

$^1$H NMR (300 MHz) (CDCl$_3$) δ: (7,7',8,8' dimer): 8.98 (d, ArH, 1H), 6.86 (d, ArH, 1H), 1.30 (s, t-Bu, 9H), 1.20 (s, t-Bu, 9H) (6,6'.7,7' dimer): 9.13 (d, ArH, 1H), 7.88 (s, ArH, 1H), 1.34 (s, t-Bu, 9H), 1.15 (s, t-Bu, 9H)

MS (Thermospray after HPLC C18) (7,7',8,8'): M/Z 767 (M+19) (100%), (6,6',7,7'): M/Z: 767 (M+19) (100%).

c) 1-Mercapto-2,3-di-t-butylthio-7,8-dicyanoindolizine 1,1'-(2,2',3,3'-tetra-t-butylthio-6,6',7,7'-tetracyanodiindolizine)-disulfide is treated with a reducing agent in an appropriate solvent until all disulfide is consumed. The reaction is stopped and the product is isolated by chromatography or recrystallization, or by a combination thereof. The radical is produced by conventional techniques.

d) 1-Mercapto-2,3-di-t-butylthio-6,7-dicyanoindolizine 1,1'-(2,2',3,3'-tetra-t-butylthio-7,7',8,8'-tetracyanodiindolizine)-disulfide is treated with a reducing agent in an appropriate solvent until all disulfide is consumed. The reaction is stopped and the product is isolated by chromatography or recrystallization, or by a combination thereof. The radical is produced by conventional techniques.

EXAMPLE 16

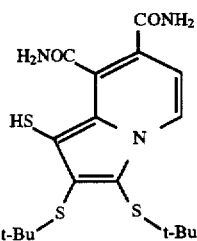

1-Mercapto-2,3-di-t-butylthio-7,8-diamidoindolizine

The title product and the resulting radical are synthesized analogously to Example 15.

EXAMPLE 17

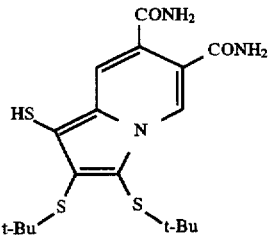

1-Mercapto-2,3-di-t-butylthio-6,7-diamidoindolizine

The title product and the resulting radical are synthesized analogously to Example 15.

EXAMPLE 18

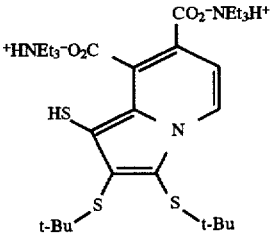

1-Mercapto-2,3-di-t-butylthio-7,8-di(triethylammonium carboxylate)indolizine

Bis(t-butylthio)cyclopropenethione and pyridine-3,4-dicarboxylic acid are mixed in a dried, argon filled reaction flask. A dry degassed solvent is added. To the mixture is added triethylamine. The reaction is stirred until no more

EXAMPLE 19

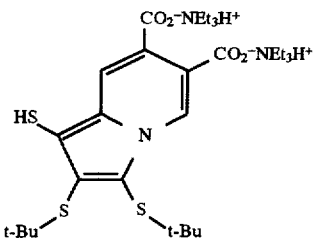

1-Mercapto-2,3-di-t-butylthio-6,7-di
(triethylammonium carboxylate)indolizine

Bis(t-butylthio)cyclopropenethione and pyridine 3,4-dicarboxylic acid are mixed in a dried, argon filled reaction flask. A dry degassed solvent is added. To the mixture is added triethylamine. The reaction is stirred until no more product is obtained. The product is isolated either by chromatography or by recrystallization, or by a combination thereof. The radical is generated by conventional techniques.

EXAMPLE 20

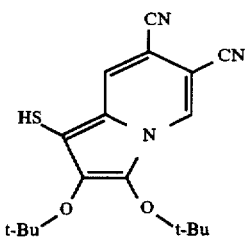

1-Hydroxy-2,3-di-t-butoxy-6,7-dicyanoindolizine.

The title compound is prepared by the following reaction scheme

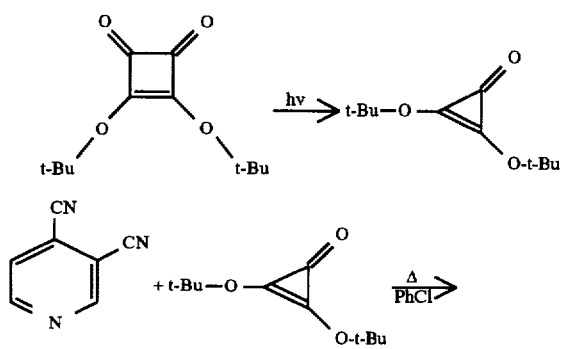

a) 1,2-Di-tert-butoxycyclobutenedione 3,4-Dihydroxy-3-cyclobutene-1,2-dione (5.0 g, 43.8 mmol) was dissolved in water (230 mL). While stirring the solution NaOH (87.7 mL, 1M, 87.7 mmol) was added dropwise. AgNO₃ (14.9 g, 87.7 mmol) dissolved in water (90 mL) was then slowly added to the solution. A yellow to green precipitate was formed. The suspension was stirred for 1 h. The precipitated silver salt was collected by filtration. It was washed with water, acetone and ether and was dried in vacum overnight. In a dry reaction flask the silver salt and dry ether (50 mL) were mixed. While stirring the suspension, t-butyl chloride (40.4 mL, 367 mmol) was added. After 48 h the reaction was stopped. The silver chloride formed was filtered off and washed with ether. The organic phases were washed with diluted NaHCO₃ and with water, dried over Na₂SO₄ and the solvent was evaporated.

Yield: 3.33g (14.7 mmol, 34%)

¹H NMR (300 MHz) (CDCl₃) δ: 1.61 (s, t-Bu). ¹³C NMR (75 MHz) (CDCl₃) δ: 188.6, 186.2, 87.0, 28.6

MS (Thermospray after HPLC C18): M/Z: 228 (M+2) (24%), 173 (100%), 157 (37%), 117 (44%).

b) 2,3-Di-tert-butoxycyclopropenone 1,2-Di-tert-butoxycyclobutenedione is dissolved in ether and photolyzed under nitrogen by a mercury high pressure lamp through quartz glass for 2–8 h depending on the quality of the mercury lamp. The title compound produced is purified by HPLC-RP, recrystallization or by distillation at low pressure, or by a combination of this techniques. (See E. V. Dehmlow, Chem. Ber. 121, 569, 1988).

1-Hydroxy-2,3-di-t-butoxy-6,7-dicyanoindolizine

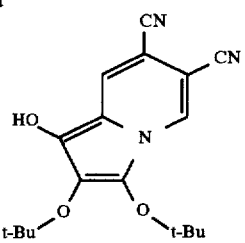

2,3-Di-tert-butoxycyclopropenone and 3,4-dicyanopyridine are mixed in a dry, argon filled flask. A solvent such as chlorobenzene (oxygen free) is used. After the completion of the reaction the product is purified by chromatography or recrystallization, or by a combination of these techniques. The radical is then generated by conventional techniques.

EXAMPLE 21

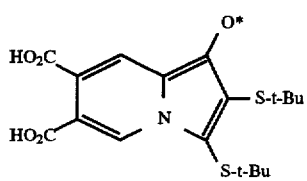

1-Oxy-2,3-di(t-butylthiol)-7,8-dicarboxylic acid-indolizinyl

The title compound was prepared by the following reaction scheme

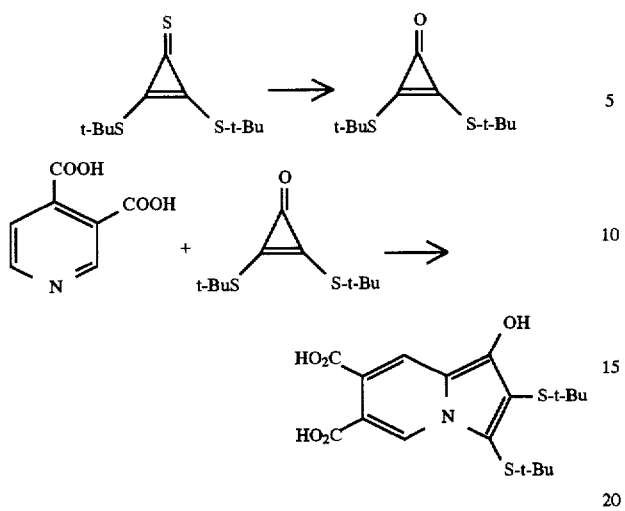

a) Bis(t-butylthio)cyclopropenone

In a dry, argon filled reaction flask was placed bis(t-butylthio)cyclopropenethione (0.200 g, 0.81 mmol). Thionychloride (1.0 mL, 5.12 mmol) was added dropwise with stirring at room temperature. A yellow precipitate was formed. After 1 h excess of thionylchloride was removed under reduced pressure, using a Rotary evaporator connected to an oil pump and an ethanol-carbon dioxide trap. By adding $CH_2Cl_2$ (5 mL) to the residual material a red solution was formed leaving a white precipitate. The solution was cooled to 0° C., washed with cold $NaHCO_3$ (5%) and dried over $Na_2SO_4$. The solvent was removed under reduced pressure. The product was filtered through a column of microcrystalline cellulose using petroleum ether as eluent and purified by recrystallisation from petroleum ether.

Yield: 122 mg (0.53 mmol, 66%)

$^1$H NMR (300 MHz) ($CDCl_3$) δ: 1.55 (s, t-bu) $^{13}$C NMR (75 MHz) ($CDCl_3$) δ: 152.2, 143.0, 48.8, 31.6

MS (EI): M/Z: 230 (M+) (25%), 202 (62%), 173 (65%), 146 (100%).

b) 1-Hydroxy-2,3-di(t-butylthio)-7,8-dicarboxylic acid-indolizine 3,4-Pyridinedicarboxylic acid (1.31 g, 7.83 mmol) and triethylamine (1.58 g, 15.7 mmol) were dissolved in chloroform (5.0 mL) (oxygen free) in a dry, argon filled reaction flask. Bis(t-butylthio)cyclopropenone (0.30 g, 1.30 mmol) was added. The reaction was stirred at 35° C. for 48 h. The reaction was terminated and the product was purified by preparative HPLC (Kromasil C18, 250×20 mm, $CH_3CN$: $H_2O$, $NH_4OAc$ pH=5). The product was unstable in the water-acetonitrile solution. It was therefore impossible to evaporate the solution. However, by allowing the fraction with pure product to stand in the freezer overnight the water and the acetonitrile were separated into two phases. The organic phase was separated and stored in the freezer. The product, which was dissolved in acetonitrile was stable in the freezer for months.

Yield 0.052 g (0.130 mmol, 10%)

$^1$H NMR (300 MHz) ($CDCl_3$) δ: 8.54 (d, ArH, 1H), 7.15 (d, ArH, 1H), 3.2 (q, $CH_2$), 1.4 (t, $CH_3$), 1.29 (s, t-bu, 9H), 1.25 (s, t-Bu, 9H).

MS (Plasma spray): M/Z: 398 (M+1) (4%), 352 (17%), 312 (100%), 256 (33%).

c) 1-Oxy-2,3-di(t-butylthio)-7,8-dicarboxylic acid-indolizinyl

1-Hydroxy-2,3-di(t-butylthio)-7,8-dicarboxylic acid-indolizine (0.014 g, 7.83 mmol) was dissolved in sodium phosphate buffer (2.5 mL, pH=8). The solution was purged for 15 sec. with air. The colour of the resulting solution was brown-green.

ESR (water, 1.23 mM, 200 G): doublet, $a_H$=1.95 G, linewidth 73 mG.

Overhauser enhancement (water, 1.23 mM): 144 at 16 W microwave power.

EXAMPLE 22

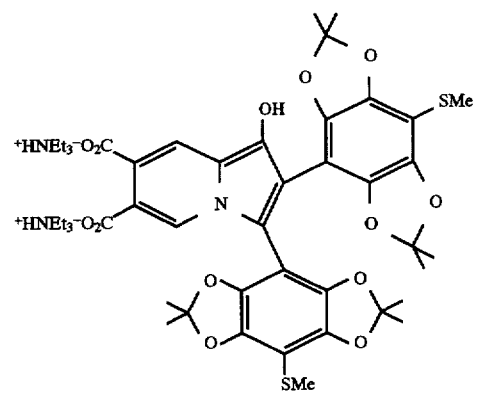

1-Hydroxy-2,3-di-(8-methylthio-2,2,6,6-tetramethylbenzo[1,2-d:4,5-d']bis(1,3)dioxole-4-yl)-6,7-di-(trialkylammonium carboxylate)indolizine The title compound is prepared according to the following reaction scheme

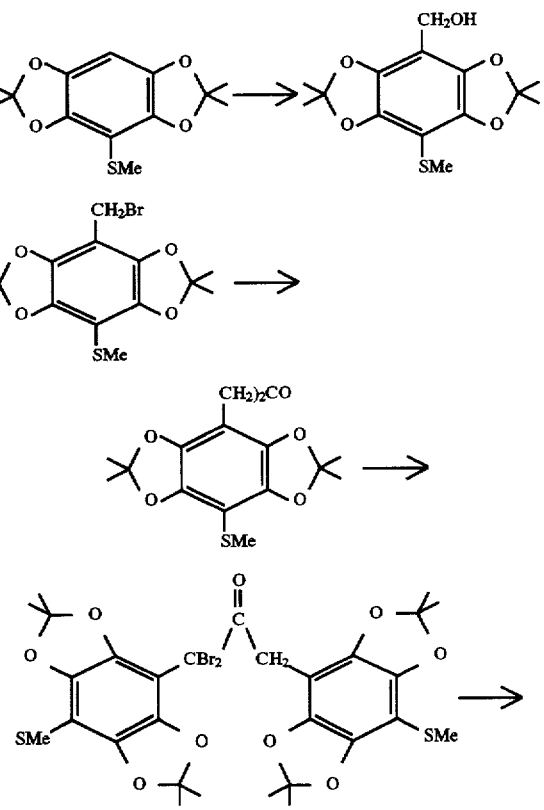

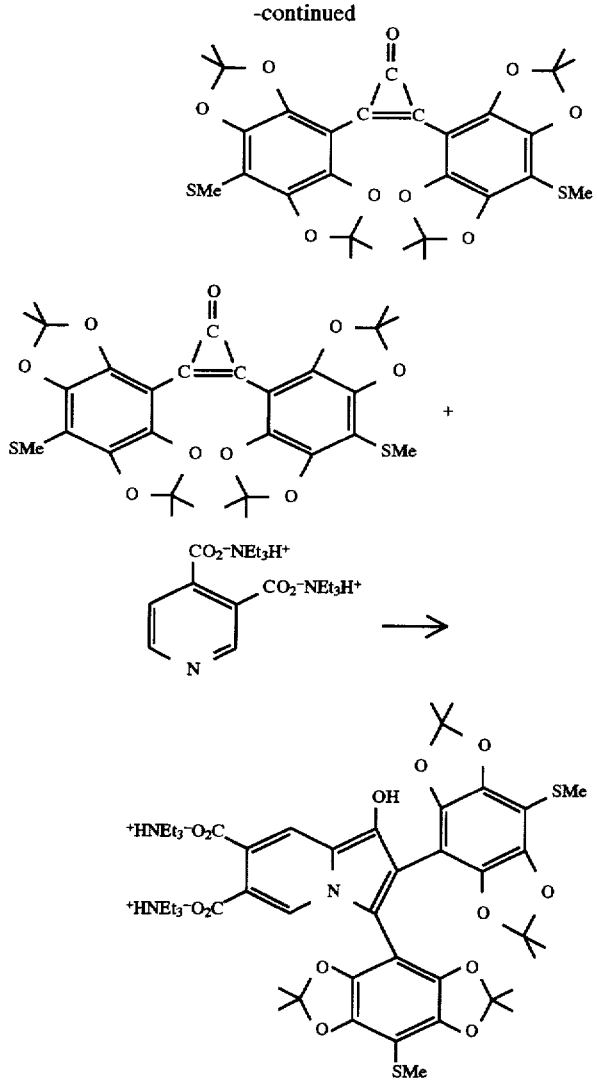

a) 4-Hydroxymethyl-8-methylthio-2,2,6,6-tetramethylbenzo[1,2-d:4,5-d']bis(1,3)dioxole 4-Hydroxymethyl-8-methylthio-2,2,6,6-tetramethylbenzo[1,2-d:4,5-d']bis(1,3)dioxole (see PCT/EP91/00285) is dissolved with stirring in dry THF in a dry, argon filled reaction flask. The solution is cooled to (−25°) −(−30°)C. Butyllithium in hexane is added dropwise with a syringe. The reaction is stirred for 0.5 h. In another reaction flask, a large excess of paraformaldehyde is depolymerized by heating. The formaldehyde formed is distilled, by means of an argon stream, into the reaction via a glass tube. When the reaction is complete, the product is hydrolyzed. The crude product is collected and is purified by recrystallization or chromatography, or by a combination of these techniques.

b) 4-Bromomethyl-8-methylthio-2,2,6,6-tetramethylbenzo[1,2-d:4,5-d']bis(1,3)dioxole 4-Hydroxymethyl-8-methylthio-2,2,6,6-tetramethylbenzo[1,2-d:4,5-d']bis(1,3)dioxole is dissolved in pyridine. The solution is chilled and triphenylphosphine followed by carbontetrabromide are added. the reaction is stirred for an appropriate time. Methanol is added and the product is isolated by a suitable method.

c) 1,3-Bis(8-methylthio-2,2,6,6-tetramethylbenzo[1,2-d:4,5-d']bis(1,3)dioxole-4-yl) acetone 4-Bromomethyl-8-methylthio-2,2,6,6-tetramethylbenzo[1,2-d:4,5-d']bis(1,3)dioxole is dissolved in dry ether in a dry, argon filled reaction vessel. The solution is cooled with a dry ice ethanol bath. With stirring, butyllithium in hexane is added. After the completion of the halogen metal exchange reaction ethyl (N,N-dimethyl) carbamate dissolved in dry ether is added. The reaction is hydrolyzed and the product is purified by chromatography or recrystallization, or by a combination of these techniques.

d) 1,1-Dibromo-1,3-bis(8-methylthio-2,2,6,6-tetramethylbenzo[1,2-d:4,5-d']bis(1,3)dioxole-4-yl) acetone 1,3-Bis(8-methylthio-2,2,6,6-tetramethylbenzo[1,2-d:4, 5-d']bis(1,3)dioxole-4-yl) acetone is dissolved in solvent. In the presence of base, bromine is added. After workup, the product is purified by chromatography or recrystallization, or by a combination of these techniques.

e) 2,3-Di(8-methylthio-2,6,6-tetramethylbenzo[1,2-d:4,5-d']bis(1,3)dioxole-4-yl)cyclopropenone Triethylamine is dissolved in $CH_2Cl_2$ with stirring. 1,1-Dibromo-1,3-bis(8-methylthio-2,2,6,6-tetramethylbenzo[1,2-d:4,5-d']bis(1,3)dioxole-4-yl) acetone in $CH_2Cl_2$ is slowly added. After completion, the reaction mixture is worked up. The product is isolated by chromatography or recrystallization, or by a combination of these techniques.

f) 1-hydroxy-2,3-di(8-methylthio-2,2,6,6-tetramethylbenzo[1,2-d:4,5-d']bis(1,3)dioxole-4-yl)-6,7-di (triethylammonium carboxylate) indolizine 2,3-Di(8-methylthio-2,2,6,6-tetramethylbenzo[2-d:4,5-d']bis(1,3)dioxole-4-yl)cyclopropenone and pyridine-3,4-dicarboxylic acid are mixed in a dry, argon filled reaction flask. A dry, degassed solvent and triethylamine are added. The reaction mixture is stirred until no more product is formed. The product is isolated either by chromatography or by recrystallization, or by a combination of these techniques. The radical is generated by conventional techniques.

EXAMPLE 23

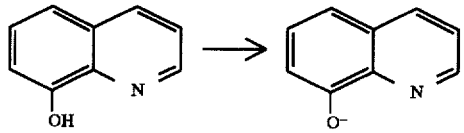

8-Oxyquinolinyl radical

8-Hydroxyquinoline (0.145 g, 1 mmol) was dissolved in a mixture of acetonitrile (20 ml) and DMSO (10 ml). Sodium hydroxide (1 ml of a 1M aqueous solution) was added. p-Benzoquinone (0.43 g, 4 mmol) was dissolved in acetonitrile (20 ml). Both solutions were purged with argon for 30 minutes and then mixed. An instant colour change from yellow to dark green was observed. The formation of the radical was verified by ESR measurements.

EXAMPLE 24

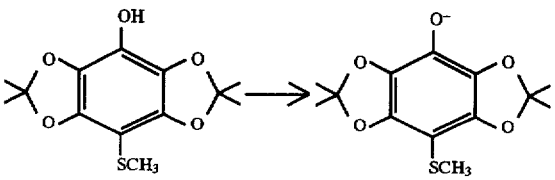

8-Thiomethyl-2,2,6,6-tetramethylbenzo[1,2-d:4,5-d'] bis(1,3)dioxole-4-oxy radical Sodium hydroxide (3.2 g, 80 mmol) and potassium ferricyanide (250 mg, 0.76 mmol) were dissolved in water (80 ml). 4-Hydroxy-8-thiomethyl-2,2,6,6-tetramethylbenzo[1,2-d:4,5-d']bis(1,3)dioxole (100 mg, 0.35 mmol) was then added and the solution was heated to 80° C. for 2 hours. A colour change from orange to pale green was observed, the formation of the radical was verified by ESR measurements.

ESR frequency 548.9 MHz. 5 lines with $a_H=106$ mg, LW=53 mg.

EXAMPLE 25

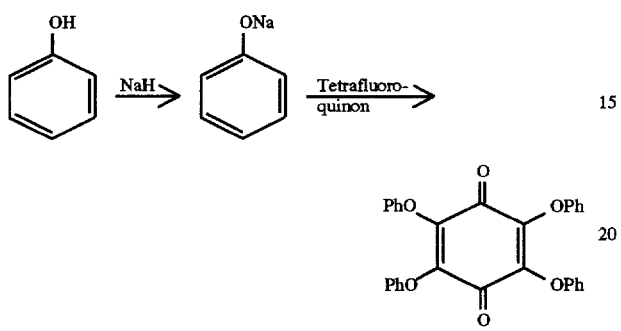

Phenol (502.1 mg, 5.335 mmol) was dissolved in DMF (4 mL, dry Aldrich sureseal). Sodium hydride (159.9 mg, 5.330 mmol, 80% in white oil) was washed twice with dry petroleum ether (decanting most of the petroleum ether after settling of the NaH), dired with argon gas and added to the phenolic solution. The resulting solution was stirred under argon while hydrogen evolved. When the gas evolution had ceased, tetrafluoroquinone (199.0 mg, 1.105 mmol) was added in portions, while cooling the mixture with an ice-water bath. The resulting solution was stirred 48 h, acidified with dilute HCl and evaporated. Water was added and the product was extracted with $CHCl_3$ (3×50 mL). The organic phase was washed with water (25 mL), dried ($Na_2SO_4$), filtered and evaporated yielding 0.7 g crude product.

The pure product was obtained by flash chromatography on silica gel eluting with $CHCl_3$. Yield 250 mg (47%). The product was identified by $^1$HNMR- and $^{13}$CNMR spectroscopy. $^1$HNMR ($CDCl_3$, 300 MHz) δ: 7.17 (m, 8H, Ar), 7.01 (m, 4H, Ar), 6.86 (m, 8H, Ar) $^{13}$CNMR ($CDCl_3$, 75 MHz) δ: 171.48, 156.37, 142.50, 129.46, 123.91, 116.80.

Small amounts of a different product was also obtained in the chromatographic separation. Using MS and NMR data, this product was identified as:

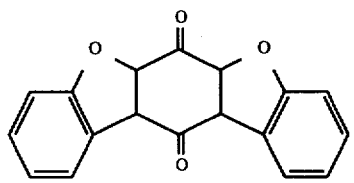

The semiquinone anion radicals are generated by convnetion techniques from the product of the Example.

EXAMPLES 26 and 27

The following products were synthesized in the same way as described in Example 25 (yield: 39%, and 45% respectively)

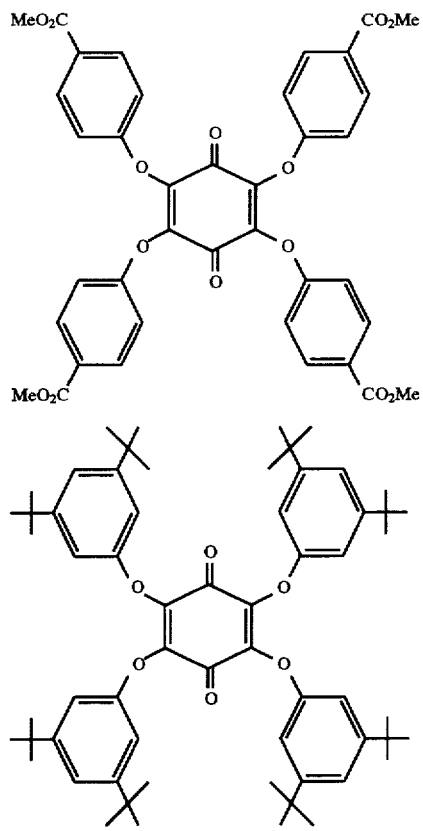

The corresponding radicals are generated using conventional techniques.

EXAMPLE 28

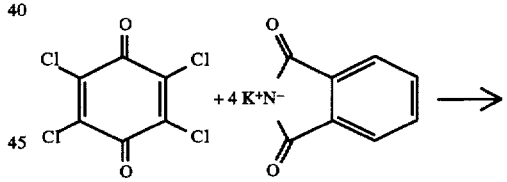

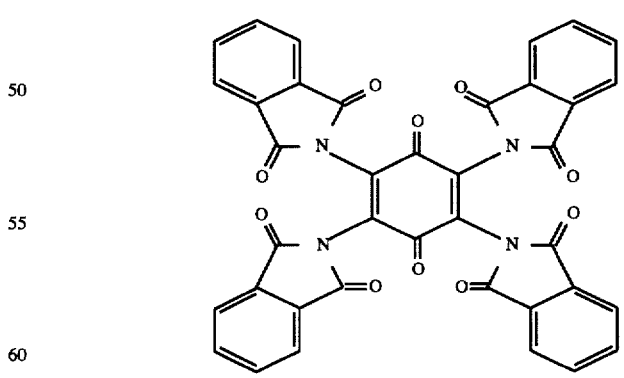

This semiquinone was made according to: Methoden der Organischen Chemie—Houben Weyl pp 464–465 number VII/3a 1977. The product was crystallized from hot EtOH. The radical is generated using conventional techniques.

EXAMPLE 29 a) 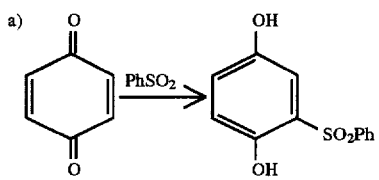

PhSO$_2$Na (1.6579 g., 0.0101 mol) was dissolved in water (100 mL), while keeping an atmosphere of N$_2$. HCl (12M, 0.84 mL, 0.0101 mol) was added in order to produce PhSO$_2$H. Benzoquinone (0.01 mol, 1.081 g) was added while flushing with N$_2$. A white to grey precipitate was formed immediately. The solution was stirred for 5 min, filtered (glass sinter no. 3) under N$_2$, washed with distilled water (−20 mL) and dried under vacuum (+20° C. over night. Yield 2.08 g. The product was identified by $^1$H- and $^{13}$CNMR spectroscopy.

$^1$H NMR (CDCl$_3$, 300 MHz) δ: 6.82 (d, 1H), 7.01 (dd, 1H), 7.24 (d, 1H), 7.58–7.73 (m, 3H, Ph), 8.00 (m, 2H, Ph) 7.4–7.7 (b, OH, 2H)

$^{13}$CNMR (CDCl$_3$, 75 MHz) δ: 150.72, 148.97, 141.91, 134.20, 129.83, 127.70, 125.43, 124.24, 119.88, 117.80, 114.47 b) 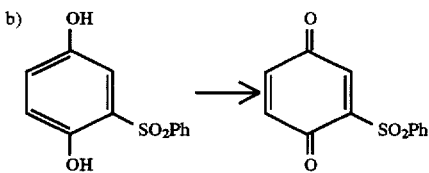

Phenylsulfonylhydroquinone (0.0250 g, 0.1 mmol) was dissolved in CH$_2$Cl$_2$ (4 mL). Silicagel (0.5 g) and NaIO$_4$ (0.65M in H$_2$O, 0.5 mL) were added. The clear solution turned yellow quickly and the solution was filtered through a short plug of silica after 15 min stirring. The product was eluted with CH$_2$Cl$_2$. Yield 0.0218 g.

The product was identified by $^1$H and $^{13}$CNMR spectroscopy.

$^1$H NMR (CDCl$_3$, 300 MHz) δ: 6.75 (d, 1H, J=10.2 HZ,), 6.86 (q, 1H, J$_a$=10.2 Hz, J$_b$=2.3 HZ) 7.62 (d, 1H, J=2.3 Hz), 7.55–7.62 (m, 2H, arom.H), 7.66–7.73 (m, 1H, arom.H), 8.07–8.12 (m, 2H, arom.H)

$^{13}$CNMR (CDCl$_3$, 75 MHz) δ: 185.79, 180.82, 138.13, 137.07, 136.90, 136.84, 134.77, 129.67, 129.31.

The radical is generated using conventional techniques.

EXAMPLE 30

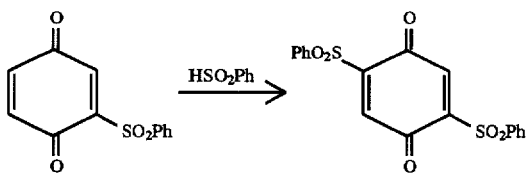

NaSO$_2$Ph (0.829 g, 5.05 mmol) was dissolved in H$_2$O (50 mL) under N$_2$. HCl (0.42 mL, conc.) was added, followed by the monophenylsulfonylquinone (1.2413 g, 5 mmol). The quinone did not dissolve, and consequently, THF (50 mL) was added with concomitant dissolution of the substrate. A red colour appeared, which changed into brown within 15 min. HCl (2 drops, conc.) were added and the solution became clearer. pH was measured to be −5. TLC analysis indicated a new lipophilic product. The THF was evaporated off and the water phase was extracted with EtOAc (3×100 mL). In the first extraction some difficulties to separate the phases were observed. Addition of some saturated NaCl solution forced the phases apart. The combined EtOAc phase was washed once with saturated NaCl, dried (Na$_2$SO$_4$), filtered and evaporated. The product was dissolved in EtOAc and filtered through a short silica column. Evaporation yielded a grey powder. Yield 30%.

The product was identified by $^1$H NMR spectroscopy.

The radical is generated using conventional techniques.

EXAMPLE 31

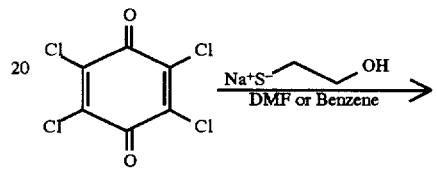

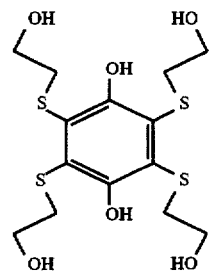

The hydroquinone is synthesized according to the procedure of Can. J. Chem. 1962, 40, page 1235. If desired the solvent may be changed to DMF and the reaction may be run at a higher temperature. The radical may be generated by conventional techniques.

EXAMPLE 32

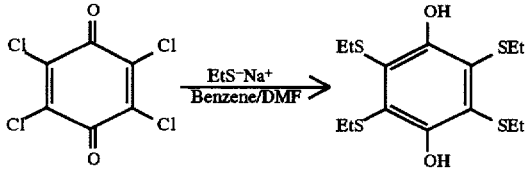

Sodium hydride (1.98 g, 0.066 mol, 80% in mineral oil), previously washed with dry petroleum ether (2×5 mL) and dried under a stream of N$_2$ was added to a solution of EtSH (4.1006 g, 0.66 mol) in DMR (55 mL) at 0° C. The resulting thick slurry was transferred to a dropping funnel and added gradually to a stirred (+10° C.) solution of chloranil (3.6882 g, 0.015 mol) in benzene (100 mL) over a period of 40 min. The reaction mixture was allowed to warm up to room temperature and stirred for 24 hours. Dilute HCl (ca 1M) was added to pH 6. The solution was evaporated at ≦40° C./4 mm Hg. The resulting black oil was partitioned between CHCl$_3$ adn water (with a little dilute HCl added to ensure a low pH). The water phase was extracted with CHCl$_3$ (4×100 mL). The combined CHCl$_3$ phases were washed with water (1×100 mL) and dried (Na$_2$SO$_4$). Evaporation gave a black oil, which crystallized in a water/ethanol mixture (dissolved in hot EtOH and hot water added until cloudiness appeared. The mixture was heated again and scratched to induce crystallization).

The product was isolated in a yield of 300 mg as yellow crystals. The identification and verification were done with the help of $^1$H NMR and IR spectroscopy and MS.

$^1$HNMR (CDCl$_3$, 300 MHz) δ: 7.37 (s, OH, 2H), 2.92 (q, CH$_2$, 8H), 1.21 (, CH$_3$, 12H)

$^{13}$CNMR (CDCl$_3$, 75 MHz) δ: 152.42, 125.07, 29.73, 14.71

The use of a larger amount of EtSH resulted in a higher yield.

The radical may be generated by conventional techniques.

EXAMPLE 33

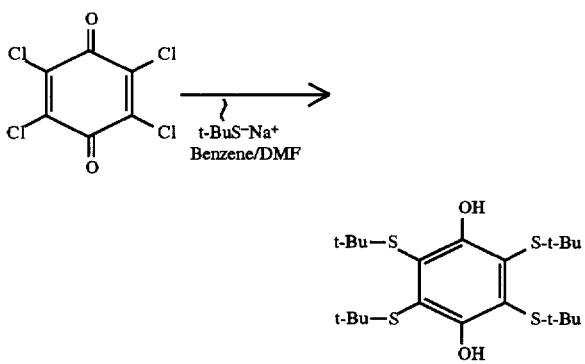

This reaction was perfomed analogously to Example 32. The product was identified by mass spectrometry.

$^1$HNMR (CDCl$_3$, 300 MHz) δ: 7.69 (s, OH, 2H), 1.31 (s, CH$_3$, 27H).

$^{13}$CNMR (CDCl$_3$, 75 MHz) δ: 155.61, 128.03, 50.42, 31.59

The radical may be generated by conventional techniques.

EXAMPLE 34

Tetraphenoxy benzoquinone is reduced with Na$_2$S$_2$O$_4$ to the tetraphenoxy hydroquinone, as described by L. Feiser et al., JACS 70, 1948, p 3165.

The product is purified by crystallization or chromatography, or by a combination of these techniques.

EXAMPLE 35

Tetraphenoxy benzoquinone is reduced with excess NaBH$_4$ in a mixture of EtOH and water. The product is purified by extractions and chromatography, or by a combination of these techniques.

The product is then monoalkylated or monoetherified to yield a phenoxy radical precursor as follows:

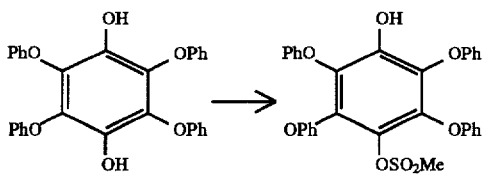

Tetraphenoxyhydroquinone is monomesylated in pyridine with one equivalent of MeSO$_2$Cl for 2–3 days at ambient temperature. The product is isolated in low to moderate yield by extractions and chromatography. (See Annalen 551:235 (1942)).

EXAMPLE 36

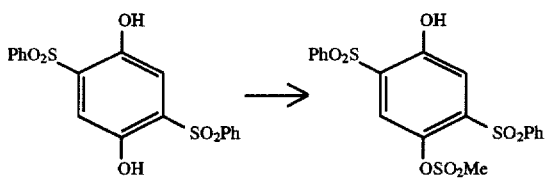

2,6-Diphenylsulfonyl hydroquinone is monomesylated in pyridine with one equivalent of MeSO$_2$Cl for 2–3 days at ambient to high temperature. The product is isolated and purified by extractions and chromatography.

EXAMPLE 37

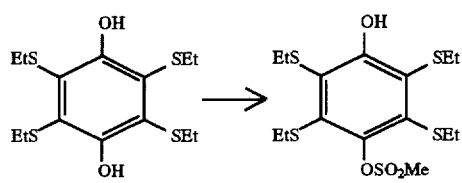

Tetraethylthiohydroquinone is monomesylated with MeSO$_2$Cl in pyridine at room temperature for 2–4 days. The product is isolated by extractions and chromatography.

Radicals may be generated from the compounds of Examples 34–37 by conventional techniques.

EXAMPLE 38

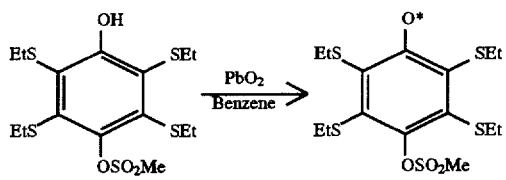

Tetraethylthiohydroquinone monomesylate is stirred with lead dioxide (excess) in the dark under an atomsphere of N$_2$. Small samples are taken, centrifuged or filtered through oxygen-free silica and analysed by ESR, or by OMRI signal enhancement measurements. The product is purified by centrifugation, filtration and recrystallization or chromatography.

EXAMPLE 39

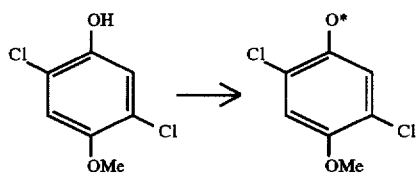

2,6-Dichlorohydroquinone monomethyl ether is stirred with an excess of K$_3$Fe(CN)$_6$ in benzene until samples taken show high conversion to the radical. The product is purified as described in Example 38.

EXAMPLE 40

Six phenoxy radical precursors are prepared according to the following reaction schemes (See also Müller, E. et al. Chem. Ber. 93, 2649 (1960) and Müller, E. and Ley, K. Chem. Ber. 87, 922 (1954)):

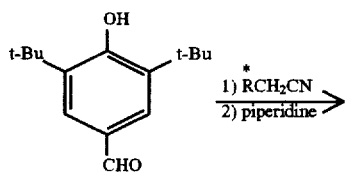

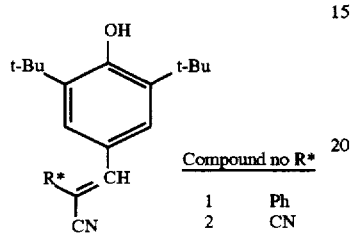

| Compound no | R* |
|---|---|
| 1 | Ph |
| 2 | CN |

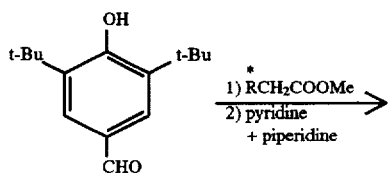

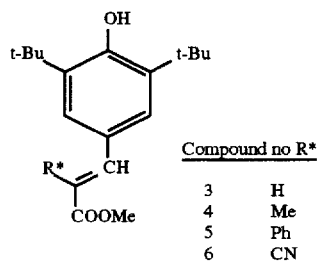

| Compound no | R* |
|---|---|
| 3 | H |
| 4 | Me |
| 5 | Ph |
| 6 | CN |

The corresponding phenoxy radicals are generated by conventional techniques.

EXAMPLE 41

A phenoxy radical precursor is prepared by a trimerization-condensation reaction as set forth below (see Martinson, P. et al., Acta Chem. Scand. 23:751–64 (1969)):

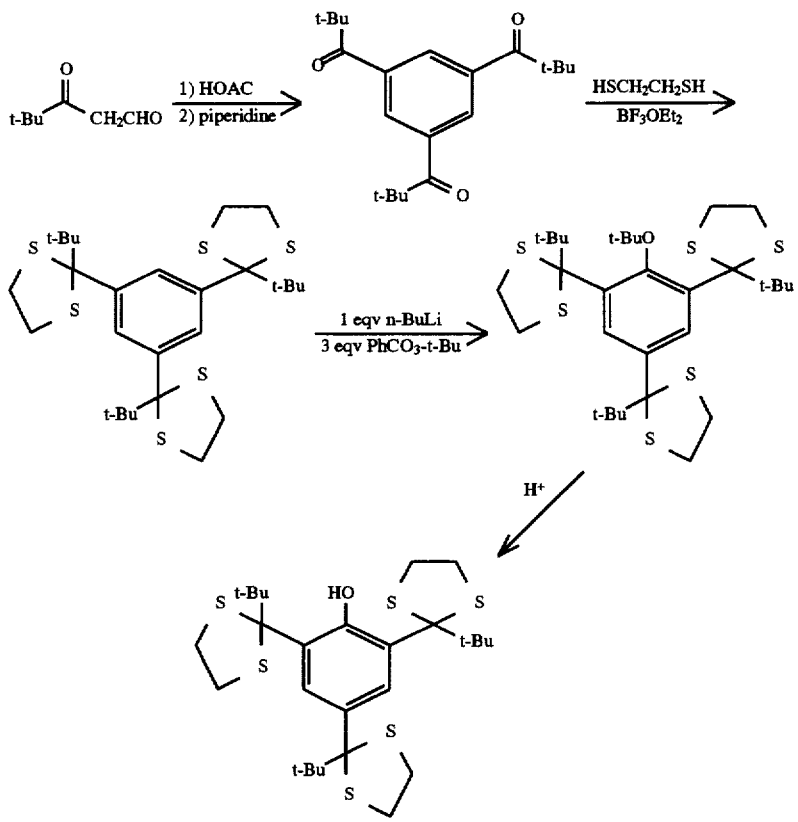

In the first stage of the reaction scheme, to a hot solution of 1,3,5-tripivaloyl benzene and ethanedithiol in acetic acid is added dropwise $BF_3.OEt_2$ (48% in $BF_3$) and the reaction mixture is left overnight for crystallization. After cooling, crystals separate. These crystals are filtered off and recrystallized for use in the later reaction steps.

The phenol end product can be transformed into a radical directly or after oxidation of the sulphurs in the steric hindrance groups according to the reaction scheme below:

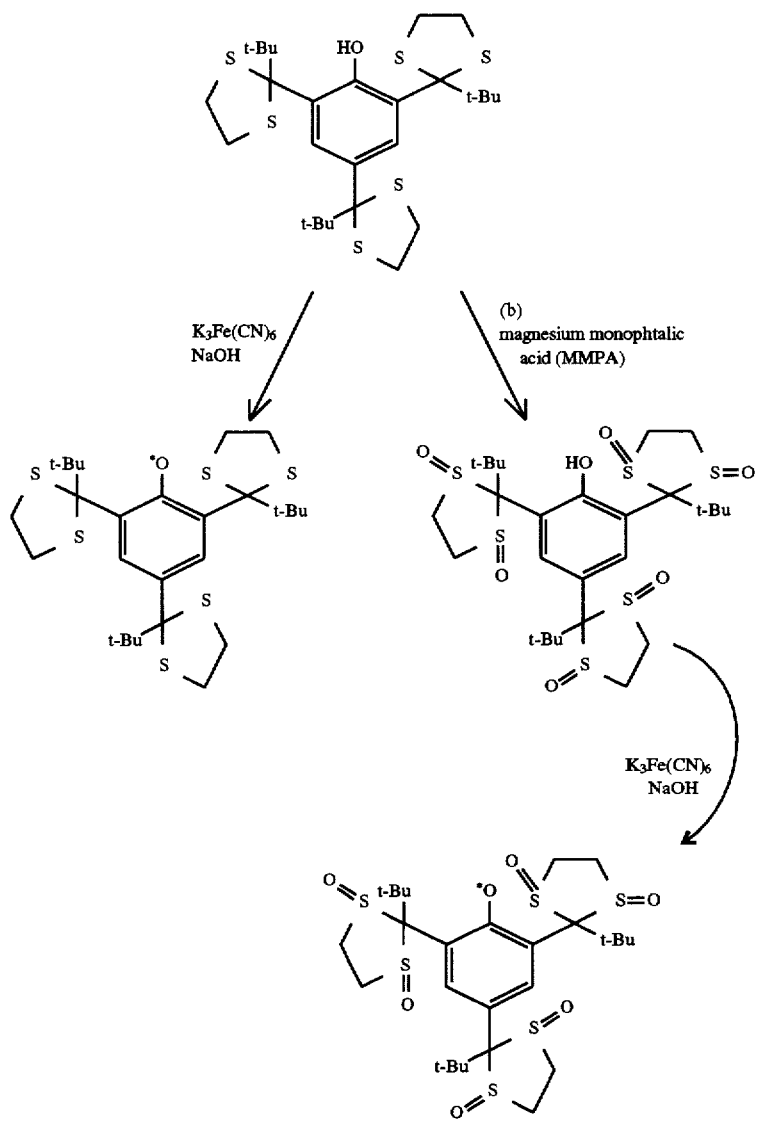

In step (b) 2-hydroxy-1,3,5-tripivaloyl benzene trisethylenethioketal is dissolved in $CH_2Cl_2$ at ambient temperature. Magnesium monoperphtalic acid (MMPA) and tetra-n-butylammonium hydrogensulphate ($Q+HSO_4-$ dissolved in water are added dropwise.

The reaction is complete after several hours. The phases are separated and the organic phase is washed with a saturated solution of $NaHCO_3$. The ether phase is dried ($Na_2SO_4$) and the solvent evaporated leaving the product, which can be purified via distillation, crystallization or chromatography, or combinations thereof.

EXAMPLE 42

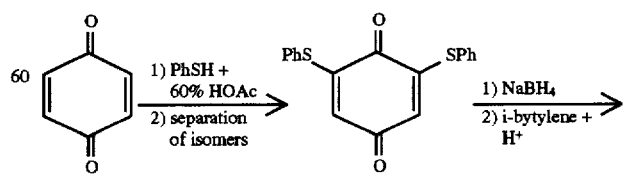

(see Becker et al. New J. Chem 12:875–880 (1988))

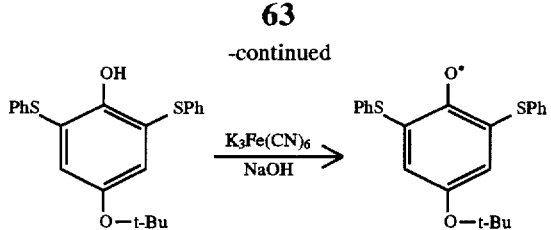

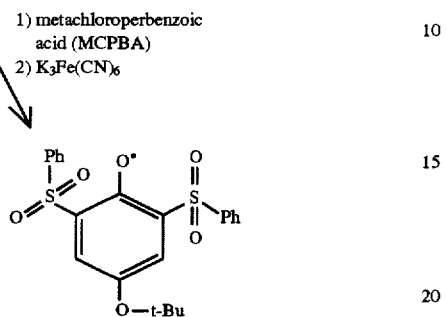

p-Benzoquinone is dissolved in acetic acid (60%). The thiophenol is slowly added at ambient temperature with efficient stirring. After stirring (3–4 days) a voluminous red precipitate is formed and filtered off. The product can be crystallized and the two isomeric products (the 2,6- and 2,4-isomers, respectively) can be separated by chromatography. The reduction of the quinone product is performed in absolute EtOH with $NaBH_4$. After stirring, 2M HCl is added until pH=2–3. The ethanol is evaporated, and the residue is partitioned between ether and water. The ether phase is dried ($Na_2SO_4$) and the solvent is evaporated, leaving a residue, which was used without further purification. The O-alkylation of the product (2,6-bisphenylthio hydroquinone) can be performed in dry dioxane with isobutylene, condensed into the solution, and a catalytic amount of concentrated sulfuric acid. The reaction flask is sealed and the reaction mixture is stirred at room temperature for 10 h. The reaction mixture is then neutralized with solid $NaHCO_3$ (until $CO_2$ evolution ceases). After drying ($Na_2SO_4$), the solvent is evaporated to give the t-butoxylated product.

2,6-Diphenylthio-4-t-butoxyphenole is dissolved in $CH_2Cl_2$ and mixed with metachloroperbenzoic acid (MCPBA) and Q+HSO[31]$_4$, dissolved in water. Efficient stirring is maintained at reflux for 20 h. Sodium sulphite is added to reduce the excess MCPBA. After concentration in high vacuum, the reaction mixture is worked up to give the product, which is purified via distillation, crystallization or chromatography, or combinations thereof.

EXAMPLE 43

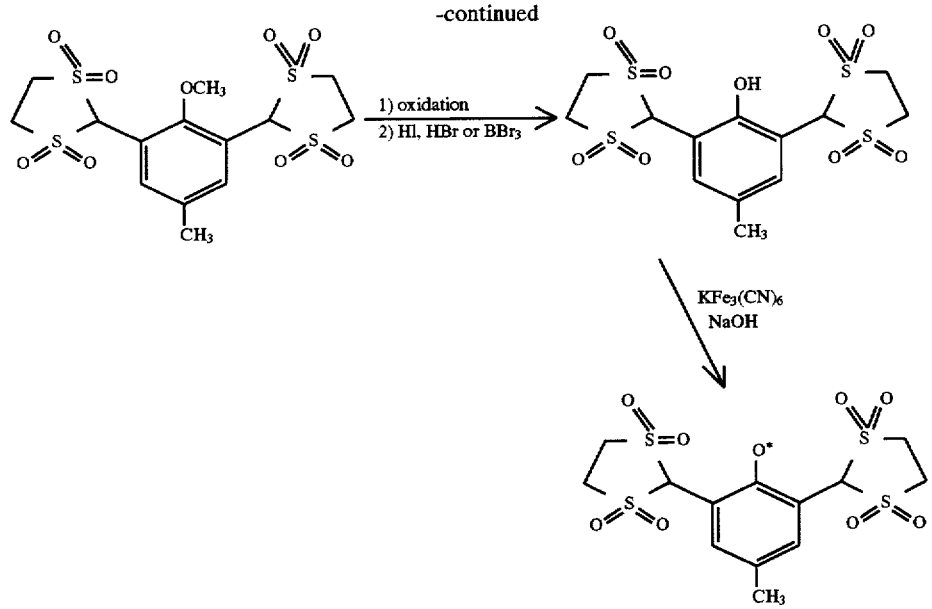

EXAMPLE 44

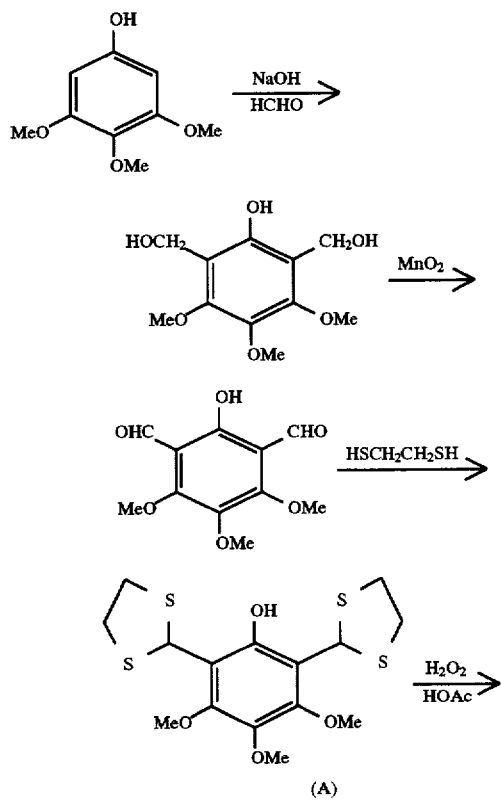

The reaction is performed according to the method of Ullman et al. Chem. Ber. 42:2539–2548 (1909). If another oxidant is selected the same reaction sequence can be used to give the corresponding 5-COOH derivative.

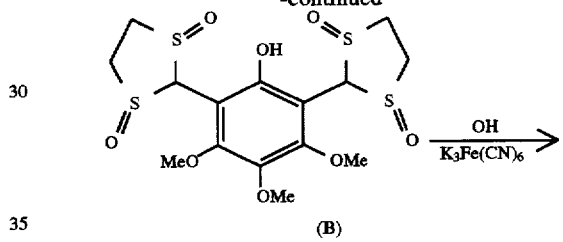

3,4,5-trimethoxyphenol is dissolved in a 2M solution of NaOH at room temperature. Formaldehyde solution (37%) is added and the mixture is stirred for two days at room temperature. The reaction mixture is then neutralized with diluted (50%) acetic acid (to pH=6–7) and the product is isolated and used without further purification in the next reaction step.

The product of the first reaction step is dissolved in dry acetone and active $MnO_2$ is added. The mixture is stirred for 24 h at room temperature. The mixture is filtered, and the filtrate treated with an acidic ion exchanger (e.g. Dowex 50×B) and filtered again. After evaporation of the solvent the di-aldehyde product can be isolated. This compound is dissolved in glacial aceitc acid with warming. After cooling, ethanedithiole and a few drops of $BF_3.OEt_2$ are added. Stirring is maintained for 20 h. The acetic acid is evaporated at reduced pressure (1–2 torr) and the residue is the desired product, compound (A).

The oxidation of the compound (A) takes place in glacial acetic acid with $H_2O_2$ (35%). Stirring is continued at room temperature for 48 h. The excess peroxide is destroyed by the careful addition of a saturated solution of sodium sul-

EXAMPLE 45

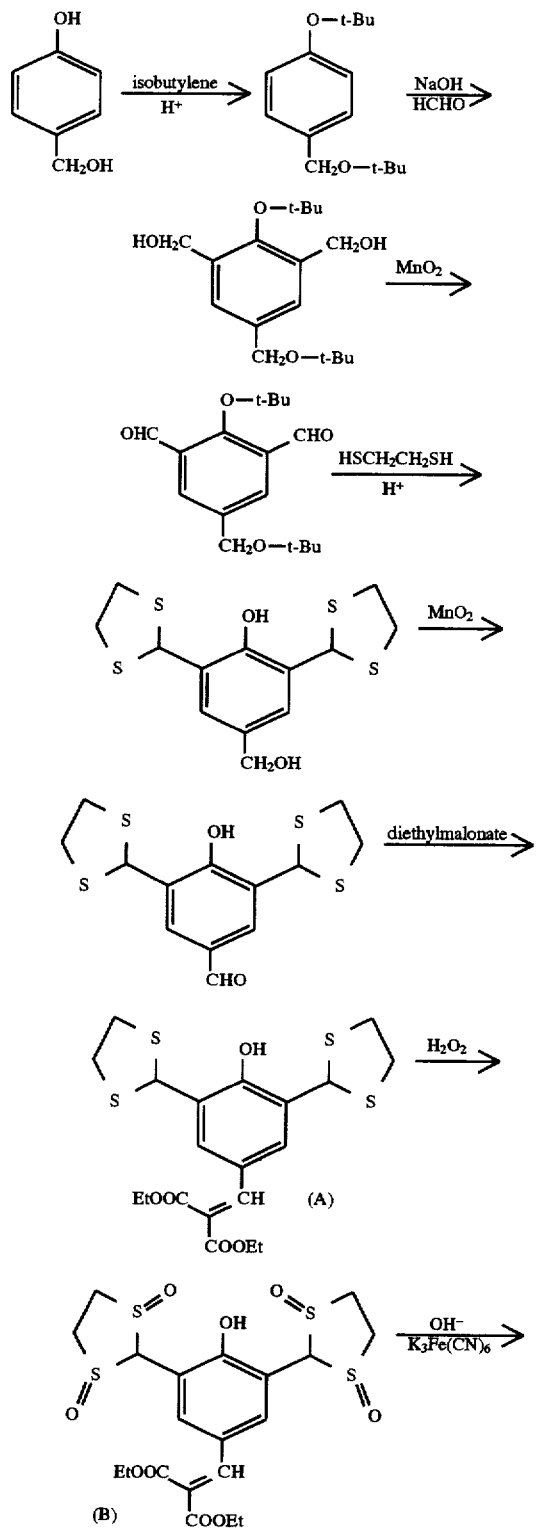

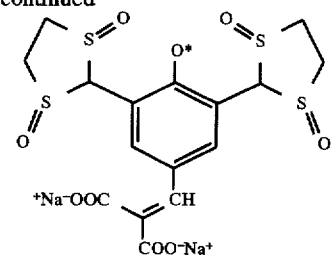

p-Hydroxymethyl phenol is etherified by dissolving it in dioxane, condensing isobutylene into the solution and adding a catalytic amount of mineral acid. This product can be converted to the di-hydroxymethyl derivative by addition to a solution of NaOH (50%) adn then adding, at room temperature, a solution of formaldehyde (37%). The oxidation of this product takes place with active $MnO_2$ (20 equivalents) in acetone. In the next reaction step, the starting product is dissolved in glacial acetic acid, and ethanedithiol (2.5 equivalents), and a few drops of $BF_3.OEt_2$ are added. After stirring overnight, the reaction mixture is worked up by evaporation of the solvent. The residue is then purified by crystallization, distillation or chromatography, or combinations thereof. There follows another oxidation with $MnO_2$, and the aldehyde is isolated and then condensed with an active methylene compound to give compund (A), according to the general procedures given by Müllet et al. (see Example 40).

The phenol function can, by use of diazomethane, be protected to give compound (B), which can be oxidized with hydrogen peroxide (20 equivalents) in acetic acid. The excess peroxide is reduced by the addition of sodium sulphite. The product can then be purified by crystallization, distillation or chromatography, or combinations thereof.

The methyl ether is cleaved to the phenol with hydrogen iodide in acetone. The mixture is evaporated to dryness at high vacuum, and the phenol can be converted to its radical by anion formation and oxidation. S-oxidation can take place without prior phenol protection.

EXAMPLE 46

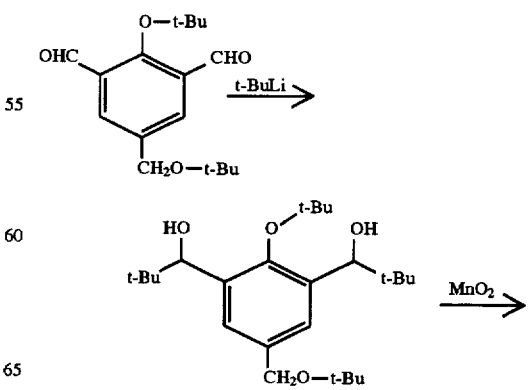

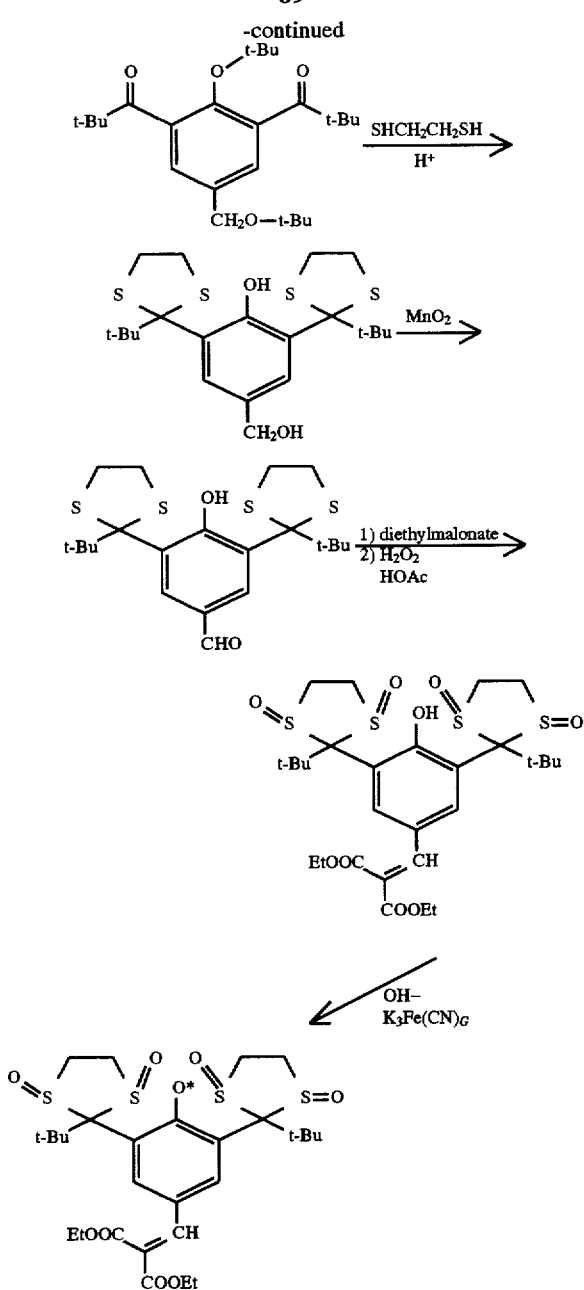

The starting compound is dissolved in dry Et₂O, and t-BuLi is added via a syringe. Stirring is continued for several hours at room temperature. After quenching with water, the phases are separated and the organic phase is worked up. The product is used directly in the next reaction step. In this it is dissolved in acetone and oxidized with active MnO₂. After stirring at room temperature for 24 h, the mixture is filtered and the solvent is evaporated under reduced pressure. The product is then purified by crystallization, distillation or chromatography, or combinations thereof. The standard procedure for thioketalisation, as given above, is followed. The thioketal product is then purified by crystallization, distillation or chromatography, or combinations thereof. The thioketal is dissolved in acetone and MnO₂ is added. After work up the aldehyde product is used directly in next step. The aldehyde compound is mixed with diethylmalonate and pyridine, according to the procedure given by Müllet et al. (see above). The product is then purified by crystallization, distillation or chromatography, or combinations thereof. It is then oxidized with hydrogen peroxide in acetic acid. After work up, including reduction of the excess peroxide, the product can then be purified by crystallization, distillation or chromatography, or combinations thereof.

EXAMPLE 47

Radical formation

The following schemes illustrate phenoxy radical formation techniques:

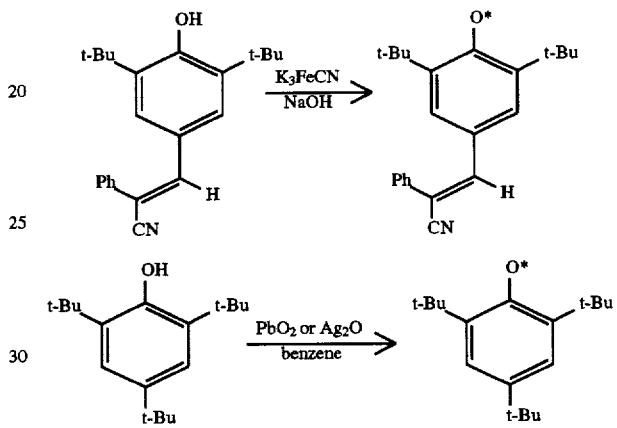

Potassiumferricyanide (0.29 g, 0.8 mmol) was dissolved in water, which had been made alkaline with potassiumhydroxide. Diethylether (80 mL) was added, and into the mixture was bubbled argon for 30 minutes. 3,5-di-tert-butyl-4-hydroxybenzaldehyde (0.1 g, 0.4 mmol) was added. After 45 minutes, the organic phase became yellow and the presence of the radical was established with ESR measurements.

3,5-Di-tert-butyl-4-hydroxyanisole (0.1 g, 0.4 mmol) was dissolved in diethylether (80 mL), and into the mixture was bubbled argon for 30 minutes. Potassiumferricyanide (0.29 g) was dissolved in water (100 mL), which had been made alkaline with potassiumhydroxide and bubbled with argon for 30 minutes. The solutions were mixed and after 10 minutes the organic phase was red and the presence of the radical was established with ESR measurements.

EXAMPLE 48

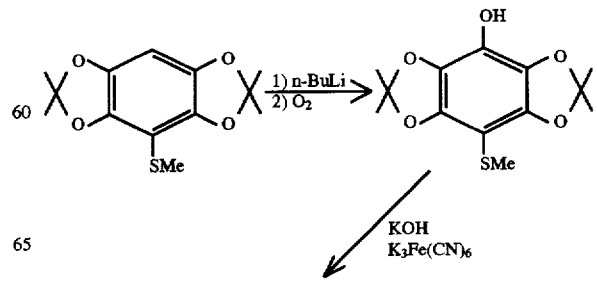

71
-continued

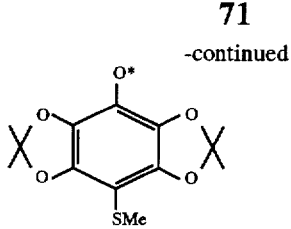

The S-methylated di-ketal (500 mg. 1.87 mmol) was dissolved in THF (50 mL. distilled over Na) under argon. The mixture was cooled to −70° C. n-Butyllithium (0.8 mL. 2.0 mmol) was added through a syringe. The mixture was stirred at −70° C. for 2 hours. The Dewar flask was removed, and $O_2$ was bubbled through the mixture for 3 h. Diethylether (50 mL) was added, and a solid precipitated. This was filtered off and dissolved in 1N NaOH and washed with $Et_2O$. The organic phase was extracted twice with 1N NaOH (10 mL). The alkaline water phase was acidified with concentrated HCl to pH 2 and then extracted with $CH_2Cl_2$ (2×50 mL). After drying, filtering and evaporation the product was isolated (130 mg. 0.46 mmol; 25%). Radical formation is performed with KOH and $K_3Fe(CN)_6$, as described above.

EXAMPLE 49

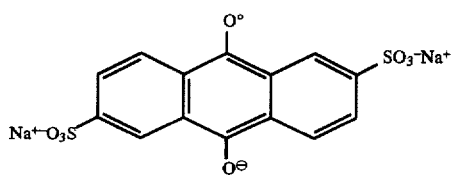

Anthraquinone-2,6-disulfonic acid disodium salt (Aldrich A9.060-8) was dissolved in a water solution, buffered to pH 11, in a concentration of 2.5 mM. 0.25 equivalents NaBH4 was added and the ESR spectrum of the solution showed 23 lines with a linewidth of 28 mG at 200 G field strength. The Overhauser enhancement was 140 (14000%) at 5 W irradiating power—irradiating at the centre line.

EXAMPLE 50

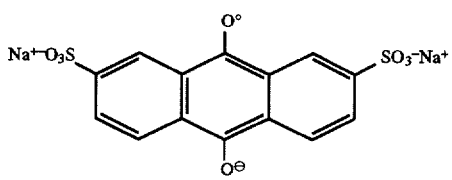

Anthraquinone-2,7-disulfonic acid disodium salt (Janssen) was dissolved in a water solution, buffered to pH 11, in a concentration of 2.5 mM. 0.25 equivalents NaBH4 was added and the ESR spectrum of the solution showed 23 lines with a linewidth of 50 mG at 200 G field strength. The Overhauser enhancement was 72 (7200%) at 5 W irradiating power—irradiating at the centre line.

72
EXAMPLE 51

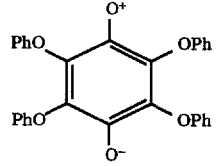

2,3,5,6-Tetraphenoxy benzoquinone was dissolved in a mixture of THF and a water solution buffered to pH 11 (3.5/0.5) in a concentration of 2.5 mM. 0.25 equivalents NaBH4 was added and the ESR spectrum of the solution showed 9 lines with a linewidth of 16 mG at 200 G field strength. The Overhauser enhancement was 114 (11400%) at 5 W irradiating power—irradiating at the centre line.

EXAMPLE 52

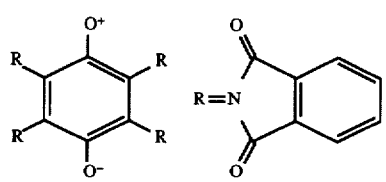

2,3,5,6-Tetraphtalimido benzoquinone was dissolved in DMF in a concentration of 5.0 mM. 0.25 equivalents of NaBH4 was added adn the ESR spectrum of the solution showed 9 lines with aH=400 mG, with a linewidth of 30 mG at 200 G field strength. The Overhauser enhancement was 5 (500%) at 5 W irradiating power—irradiating at the centre line.

EXAMPLE 53

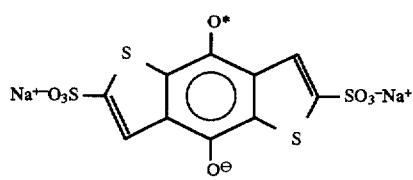

2,3,5,6-Dithienyl benzoquinone 2', 2"—disulfonic acid di sodium salt was dissolved in a water solution, buffered to pH 11, in a concentration of 5.0 mM. 0.25 equivalents of NaBH4 was added and the ESR spectrum of the solution showed 3 lines with aH=180 mG with a linewidth of 28 mG at 200 G field strength. The Overhauser enhancement was 72 (7200%) at 5 W irradiating power—irradiating at the centre line.

EXAMPLE 54

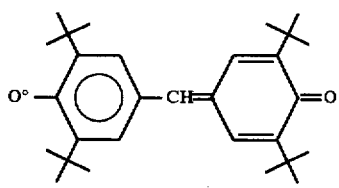

Galvinoxyl free radical (Aldrich G30-7) was dissolved in toluene at a concentration of 2.5 mM. The ESR spectrum showed one broad signal with an apparent linewidth of approximately 9.5 G at 200 G magnetic field strength. At 4.5 W irradiating power at the centre of the ESR spectrum an Overhauser enhancement of 99 (9900%) was observed.

EXAMPLE 55

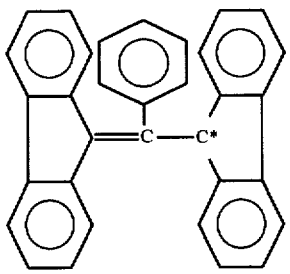

BDPA free radical complex with benzene (Aldrich 15,256-0) was dissolved in toluene in a concentration of 2.5 mM. The ESR spectrum showed one broad signal with an apparent linewidth of approximately 9.0 G at 200 G magnetic field strength. At 5.0 W irradiating power at the centre of the ESR spectrum an Overhauser enhancement of 165 (16500%) was observed. AT 21 mW irradiating power at the centre of the ESR spectrum an Overhauser enhancement of 6 (600%) was observed.

EXAMPLE 56

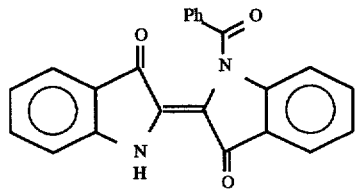

1-Benzoyl indigo was dissolved in THF (10 mM) and NaBH4 (2.5 mM) was added. At 5.0 W irradiating power at the centre of the ESR spectrum an Overhauser enhancement of 20 (2000%) was observed.

EXAMPLE 57

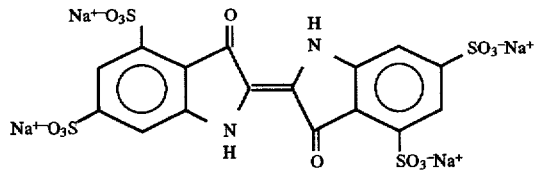

1,6-Dibenzoyl indigo was dissolved in THF (10 mM) and NaBH4 (2.5 mM) was added. At 5.0 W irradiating power at the centre of the ESR spectrum an Overhauser enhancement of 65 (6500%) was observed.

EXAMPLE 58

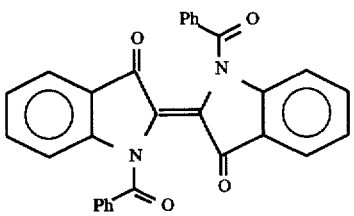

Potassium indigotetrasulfonate (Aldrich 23,408-7) was dissolved in water buffered to pH 11 at a concentration of 10 mM. Radicals were formed spontaneously in the solution. The ESR spectrum showed 15×3 lines with coupling constants of 600 and 126 mG. The apparent linewidth was 35 mG. At 5.0 W irradiating power at the centre of the ESR spectrum an Overhauser enhancement of 70 (7000%) was observed.

EXAMPLE 59

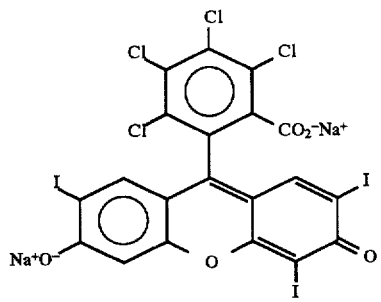

Rose bengal (Aldrich 19,825-0) was dissolved in degassed MeOH (10 mM) and heated. Radicals were formed spontaneously—presumably some oxygen in the solution worked as an oxidant. Formally the radical can be regarded as an aroxyl radical. The ESR spectrum of the cooled solution showed 13 lines with a linewidth of 181 mG. At 5.0 W irradiating power at the centre of the ESR spectrum an Overhauser enhancement of 120 (12000%) was observed.

EXAMPLE 60

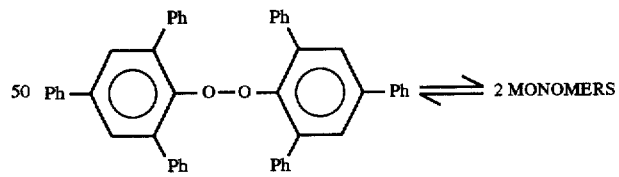

2,4,6-Triphenylphenoxyl dimer (Aldrich 27,245-0) was dissolved in toluene (dry, degassed with argon). The maximum concentration of dimer was 1.25 mM assuming no dissociation to radical monomers. The corresponding maximum concentration of radicals could theoretically be 2.5 mM assuming 100% dissociation.

This solution gave an ESR spectrum with an apparent linewidth of 5 Gauss. The intrinsic linewidth must however be much narrower, as seen from the Overhauser enhancement experiments which gave the following results:

Irradiation with 24 mW effect gave 4.6 enhancements (460%) and irradiation 810 mW gave 26 enhancements

EXAMPLE 61

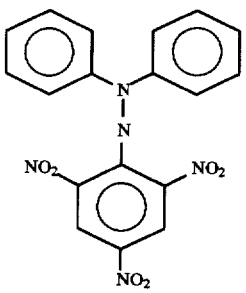

2,2-Diphenyl-1-picrylhydrazyl hydrate free radical (Aldrich D 21,140-0) was dissolved in a concentration of 2.5 mM in THF. The ESR spectrum showed one very broad signal at 200 G magnetic field strength. At 5.0 W irradiating power at the centre of the ESR spectrum an Overhauser enhancement of 39 (3900%) was observed. At 350 mW irradiating power an Overhauser enhancement of 5 (500%) was observed.

EXAMPLE 62

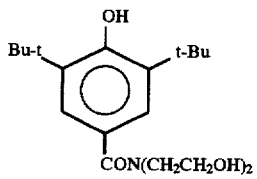

N,N-bis-(2-hydroxyethyl)-3,5-bis-(1,1-dimethylethyl)-4-bydroxybenzenecarboxamide 3,5-bis-(1,1-dimetyletyl)-4-hydroxybenzenecarboxylic acid (2.5 g, 0.010 mol) and diethanolamine (1.05 g, 0.010 mol) were dissolved in 30 ml of dry dimethylformamide and dicyclohexylcarbodiimide (2.13 g, 0.0105 mol) in 10 ml of dry dimethylformamide was added over 5 minutes. After stirring overnight, the resulting colorless suspension was filtered, and the filtrate was evaporated, 3×25 ml of benzene was added and reevaporated to yield a white solid which was recrystallised from toluene.

Yield: 2.06 g (61%)

$^1$H NMR (CDCl$_3$, 300 MHz) δ: 7.34 (s, 2H, ArH), 5.42 (s, 1H, ArOH), 4.2-2.6 (m, 10H, CH$_2$CH$_2$OH), 1.43 (s, 18H, C(CH$_3$)$_3$)

Mass spectrum (APcI, 25 V): m/e (%rel.int.) 338 (100) (M+1), 321 (5), 174 (4), 115 (6), 106 (31).

EXAMPLE 63

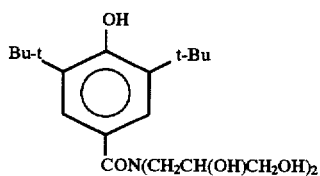

N,N-bis-(2,3-dihydroxypropl)-3,5-bis-(1,1-dimethylethyl)-4-hydroxybenzenecarboxamide 3,5-bis-(1,1-dimethylethyl)-4-hydroxybenzenecarboxylic acid (5.0 g, 0.020 mol) and bis-(2,3-dihydroxypropyl)-amine (3.3 g, 0.020 mol) were dissolved in 60 ml of dry dimethylformamide and dicyclohexylcarbodiimide (2.13 g, 0.0105 mol) in 20 ml of dry dimethylformamide was added. After stirring overnight the resulting colorless suspension was filtered, and the filtrate was evaporated, added 3×25 ml of benzene and reevaporated to yield a white solid; according to HPLC a mixture of starting material, title compound and at least two other products. The title compound was isolated by preparative HPLC.

Yield: 0.1 g (1%) (not optimized, crude HPLC yield: ca 30%).

$^1$H NMR ((CD$_3$)$_2$SO, 300 MHz) δ: 7.20 (s, 2H, ArH), 5.02 (s,

1H, ArOH, 3.8–3.2 (m, 14H, CH$_2$CH(OH)CH$_2$OH), 1.36 (s, 18H, C(CH$_3$)$_3$).

Mass spectrum: (APcI, 25V): m/e (rel.int.) 398 (100) M+1), 304 (5), 250 (7), 201 (9), 178 (2), 160 (16), 142 (48), 101 (45).

EXAMPLE 64

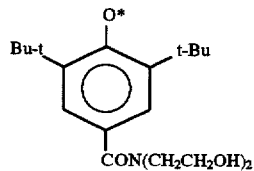

N,N-bis-2hydroxyethyl)-2,6-bis-(1,1-dimethylethyl) benzene-4-carboxamide-1-oxy radical To a saturated solution of N,N-bis-(2-hydroxyethyl)-3,5-bis-(1,1-dimethylethyl)-4-hydroxybenzenecarboxamide in redistilled, Argon-flushed water (50 mg in 50 ml) 1.0 g of lead dioxide was added in one portion while flushing with argon. The flask was sealed with an ordinary stopper and teflon tape and thoroughly shaken. The dark green solution thus obtained was used directly for ESR-measurements.

ESR-data (H$_2$O, 0.75 mM): triplet, linewidth=900 mG; a$_H$=1650 mG.

EXAMPLE 65

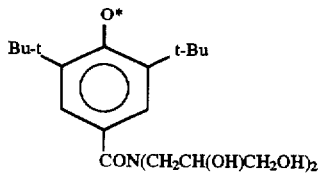

N,N-bis-2,3-dihydroxypropyl)-2,6-bis-(1,1-dimethylethyl)-benzene-4-carboxamide-1-oxy radical To a saturated solution of N,N-bis-(2,3-dihydroxypropyl)-3,5-bis-(1,1-dimethylethyl)-4-hydroxybenzenecarboxamide in redistilled, Argon-flushed water (50 mg in 50 ml) was added in one portion while flushing with argon, 0.5 g of lead dioxide. The flask was sealed with an ordinary stopper and teflon tape and thoroughly shaken. The dark green solution thus obtained was used directly for ESR-measurements.

ESR-data (H$_2$O, 3.79 mM): triplet, linewidth=900 mG; a$_H$=1850 mG.

EXAMPLE 66

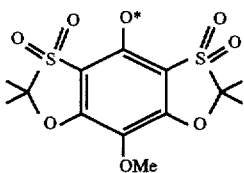

8-Methoxy -3,3,5,5-tetraoxo-2,2,6,6-tetramethylbenzo[1,2-d;4,5-d']-bis 1,3 oxathiole-4-oxyl The title compound was prepared according to the following scheme:

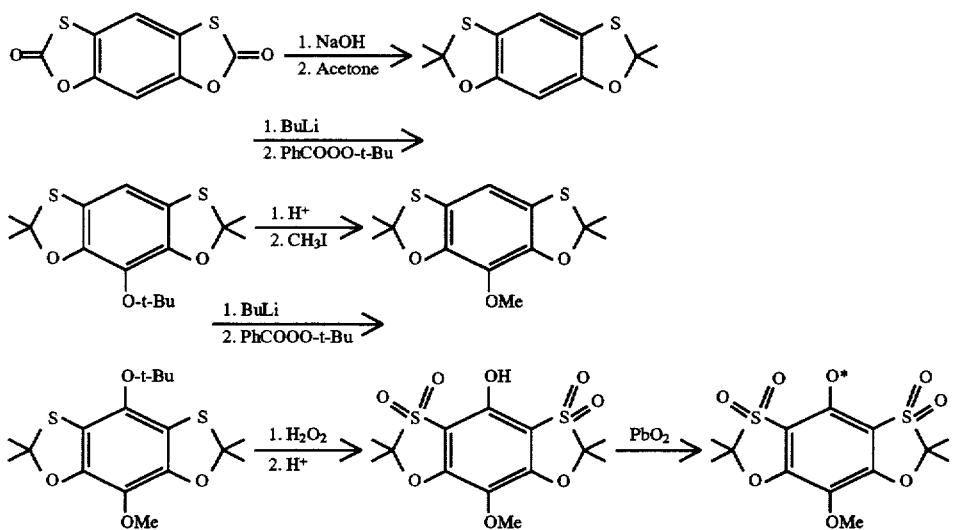

a) 2,2,6,6-tetramethylbenzo[1,2,-d;4,5-d']-bis(1,3)-oxathiole 2,6-Dioxo-benzo[1,2-d:5,4-d']bis(1,3)oxathiole (1.0 g, 4.4 mmol), prepared according to the literature (H. Fiedler, Berichte 95, 1771 (1962)) was suspended in dry methanol (30 mL) and a solution of sodium methoxide in methanol (prepared from 20 mL methanol and 2.2 mmol. sodium) was then added over a period of 15 minutes. After stirring for 15 minutes, the mixture was poured onto diethyl ether (50 mL) and 1M aqueous HCl (25 mL). The aqueous phase was extracted twice with ether and the combined organic phases were dried (MgSO$_4$) and evaporated. The residue (0.60 g) was dissolved in dry acetonitril (40 mL) containing acetone (6 mL) and BF$_3$.Et$_2$O (4 mL) was then added. After stirring for 20 minutes, water (100 mL) and dichloromethane (50 mL) were added. The aqueous phase was extracted twice with dichloromethane and the combined organic phases were dried (MgSO$_4$) and evaporated. The brownish residue was passed through a short silica column using ethyl acetate-:cyclohexane (1:5) as the eluent to give 0.30 g of a yellow solid which was further purified by preparative HPLC (RP-18, acetonitrile:water 80:20).

Yield 0.25 g (23%). $^1$H NMR (CDCl$_3$) δ: 1.80 (s, 12H, CH$_3$), 6.35 (s, 1H), 6.75 (s, 1H).

b) 8-t-Butoxy-2,2,6,6-tetramethylbenzo[1,2-d:5,4-d']bis(1,3)oxathiole 2,2,6,6-Tetramethylbenzo[1,2-d:5,4-d']bis(1,3)oxathiole (300 mg, 1.18 mmol) was dissolved in dry diethyl ether (30 mL) and the solution was cooled to −78° C. A solution of n-BuLi in hexane (2.5M, 0.52 mL) was added and the reaction was allowed to attain room temperature. After stirring for 1 hour, the mixture was cooled to −78° C. and transferred into a solution of MgBr$_2$ in dry ether (prepared from magnesium, 60 mg and 1,2-dibromoethane, 0.2 mL in 2 mL ether) kept at −78° C. The mixture was stirred for 30 minutes at 0° C. and then, a solution of t-butylperbenzoate (0.24 mL, 0.12 mmol) in dry ether (2 mL) was added. After stirring for 1 hour at 0° C., the mixture was poured onto a mixture of ice and 0.1M aqueous HCl. The aqueous phase was extracted three times with ether and the combined organic phases were washed with aqueous NaHSO$_3$, 2M NaOH, dried (MgSO$_4$) and evaporated. The product was purified by preparative HPLC (RP-18, CH$_3$CN: H$_2$O 80:20). Yield 124 mg (32%).

$^1$H NMR (CDCl$_3$) δ: 1.36 (s, 9H, t-Bu), 1.82 (s, 12H, CH$_3$) 6.54 (s, 1H).

c) 8-Methoxy-2,2,6,6-tetramethylbenzo[1,2-d;5,4-d']bis(1,3)oxathiole 7-t-Butoxy-2,2,6,6-tetramethylbenzo[1,2-d;5,4-d']bis-(1,3)oxathiole (152 mg, 0.47 mmol) was dissolved in 1,1,1-trifluoroethanol (4 mL) and cooled to −10° C. A solution of CF$_3$SO$_3$H in 1,1,1-trifluoroethanol (0.11M, 0.52 mL) was then added and the mixture was stirred for 40 minutes at −5° C. A solution of triethyl amine in ether (0.14M, 0.41 mL) was then added, the solution was evaporated and the product purified by preparative HPLC (RP-18, CH$_3$CN: H$_2$O 80:20). Yield 113 mg (90%).

$^1$H NMR (CDCl$_3$) δ: 1.86 (s, 12H, CH$_3$), 4.74 (s, 1H, OH), 6.40 (s, 1H).

This phenol was then methylated using phase-transfer conditions. Thus, a solution of the phenol (0.48 mmol, 130 mg) was dissolved in CH$_2$Cl$_2$ (20 mL) together with tetrabutylammonium hydrogensulfate (163 mg, 0.48 mmol), 1M aqueous NaOH (20 mL) and methyl iodide (2.4 mmol, 0.15 mL). The mixture was stirred vigorously for 15 hours, the organic phase was evaporated and triturated with ether. The organic phase was washed with brine, water, dried (Na$_2$SO$_4$) and evaporated. The product was purified by preparative HPLC (RP-18, CH$_3$CN: H$_2$O 80:20).

Yield 133 mg (97%). $^1$H NMR (CDCl$_3$) δ: 1.86 (s, 12H, CH$_3$), 3.92 (s, 3H, OCH$_3$), 6.52 (s, 1H).

d) 4-t-Butoxy-8-methoxy-2,2,6,6-tetramethylbenzo[1,2-d;5,4-d']bis(1,3)oxathiole

7-Methoxy 2,2,6,6-tetramethylbenzo[1,2-d;5,4-d'bis(1,3)-oxathiole (142 mg, 0.50 mmol) was dissolved in dry diethyl ether (20 mL) and cooled to -78° C. A solution of n-BuLi in hexane (2.5M, 0.52 mL) was added and the reaction mixture was stirred for 2 hours at room temperature. After cooling to -78° C., the solution was transferred to a solution of MgBr$_2$ in ether (prepared from magnesium, 24 mg, and 1,2-dibromoethane, 0.086 ml in 2 mL ether) kept at -78° C. After stirring for 45 minutes at 0° C., t-butylperbenzoate (0.6 mmol, 0.11 mL) in dry ether (2.0 mL) was added. After stirring for another hour, the mixture was poured onto a mixture of ice and 0.1M HCl. The aqueous phase was extracted three times with ether, the combined organic extracts were washed with aqueous NaHSO$_3$, 2M NaOH, dried (Na$_2$SO$_4$) and evaporated. The product was purified by preparative HPLC (RP-18, CH$_3$CN: H$_2$O 80:20). Yield 60 mg (34%).

$^1$H NMR (CDCl$_3$) δ: 1.39 (s, 9H, t-Bu), 1.84 (s, 12H, CH$_3$), 3.88 (s, 3H, OCH$_3$).

e) 4-Hydroxy-3,3,5,5-tetroxo-8-methoxy-2,2,6,6-tetramethyl-benzo[1,2-d;5,4-d']bis(1,3)oxathiole 4-t-Butoxy-8-methoxy-2,2,6,6-tetramethylbenzo[1,2-d;5,4-d']bis(1,3)oxathiole (60 mg, 0.17 mmol) was dissolved in glacial acetic acid and aqueous hydrogen peroxide (3 mL, 36%) was added. The solution was heated to 100° C. for 1 hour. After neutralization of the solvent with aqueous 2M NaOH, the mixture was extracted three times with ethyl acetate. The combined organic phases were dried (MgSO$_4$) and evaporated. The product was purified by preparative HPLC (RP-18, CH$_3$CN: H$_2$O 20 80:20). Yield 25 mg (35%).
$^1$H NMR (DMSO-d$_6$) δ: 1.69 (s, 12H, CH$_3$), 3.68 (s, 3H, OCH$_3$), 3.8 (br s, 1H, OH).

f) 8-Methoxy-3,3,5,5-tetraoxo-2,2,6,6-tetramethyl-benzo[1,2-d;5,4-d']bis(1,3)oxathiole-4-oxy The radical is prepared from 4-hydroxy-3,3,5,5-tetroxo-8-methoxy-2,2,6,6-tetramethylbenzo[1,2-d;5,4-d']bis(1,3) oxathiole using either PbO$_2$ or K$_3$Fe(CN)$_6$ as the oxidant.

EXAMPLE 67

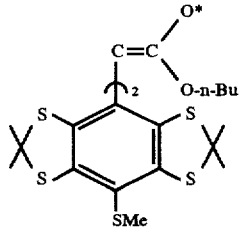

1-Butyloxycarbonyl-1-bis[-(4-methylthio-2,2,6,6-tetramethylbenzo[1,2,-d;4,5-d']-bis(1,3)dithiole)methyl The title compound is prepared according to the following scheme:

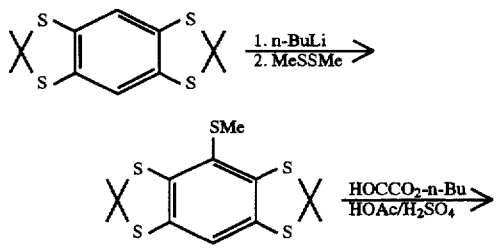

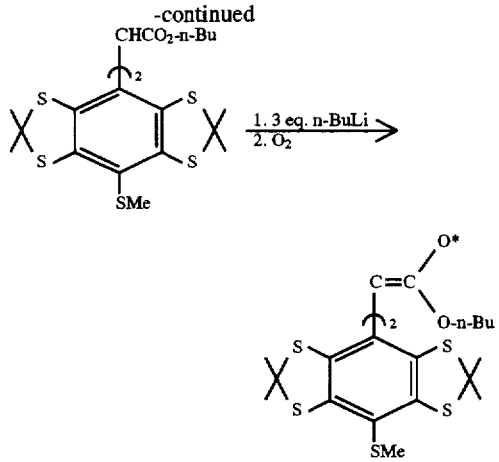

2,2,6,6-Tetramethylbenzo[1,2-d;5,4-d']bis-(1,3)dithiole is lithiated with n-BuLi in diethyl ether and then reacted with dimethyl disulfide to give 4-methylthio-2,2,6,6-Tetramethylbenzo[1,2-d;5,4-d']bis-(1,3)dithiole. This compound can then be reacted with n-butyl glyoxalate (0.5 eq.) in a solvent consisting of a mixture of concentrated sulfuric acid and glacial acetic acid (1:10) (analogously to: G. Werber, Ann. Chim. 49, 1898 (1959)). After work-up, including neutralization and extraction the product is purified by preparative HPLC. The n-butyl bis[8-(methylthio-2,2,6,6-tetramethylbenzo-[1,2-d;5,4-d']bis-(1,3)dithiole] acetate formed can be hydrolyzed with a 10% solution of sodium hydroxide and transferred into other esters, amides, thioesters and anhydrides etc. by standard procedures. If n-butyl bis[8-(methylthio-2,2,6,6-tetramethylbenzo-[1,2-d;5,4-d']bis-(1,3)dithiole] acetate is treated with n-BuLi (3 eq.) in tetrahydrofurane at ambient temperature and exposed to oxygen, the initially formed enolate anion is oxidized to the stable title radical (analogously to P. O'Neill and A. F. Hegarty, J. Org. Chem. 52, 2113 (1987)).

EXAMPLE 68

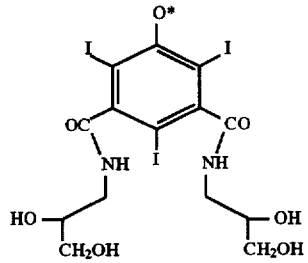

N,N'-bis 2,3-dihydroxypropyl)-2,4,6-triiodophenoxide-3,5-dicarboxylic acid diamide The title compound was prepared according to the following scheme:

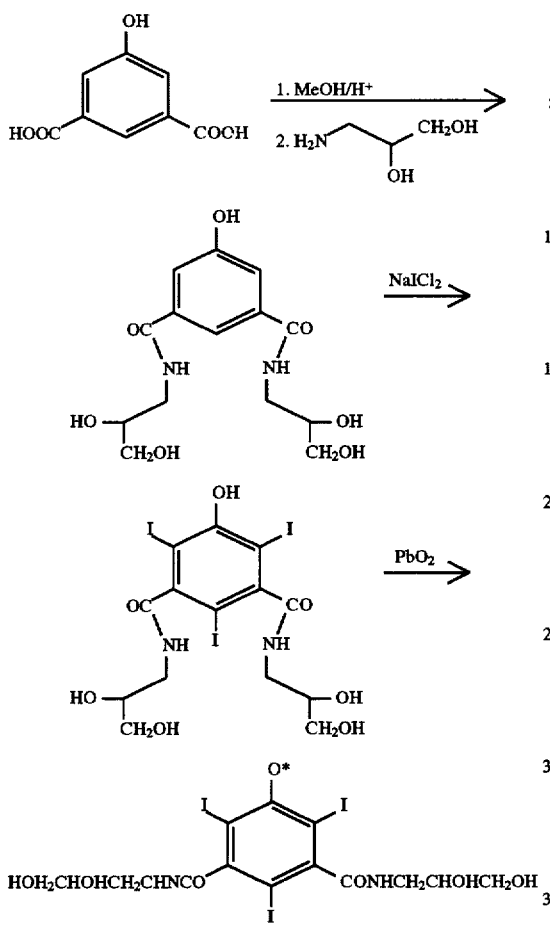

Dimethyl 1-hydroxybenzene-3,5-dicarboxylic acid

5-Hydroxyisophthalic acid (54.6 g, 0.30 mol, Aldrich 31, 127-8) was dissolved in absolute methanol (300 mL). Concentrated sulfuric acid (15 mL) was added and the reaction mixture was heated to reflux temperature for 19 hours and then cooled to −20° C. The precipitate was collected by filtration and the crude product was recrystallized in methanol.

$^1$H NMR (DMSO-d$_6$) δ: 3.90 (s, 6H, CH$_3$), 7.57 (d, 2H, J=1.5 Hz), 7.92 (t, 1H, J=1.5 Hz), 10.29 (s, 1H, OH).

$^{13}$C NMR (DMSO-d$_6$) δ: 52.36, 120.2, 120.4, 131.3, 157.9, 165.4

N,N'-bis(2,3-dihydroxypropyl)-1-hydroxybenzene-3,
5-dicarboxylic acid diamide

Dimethyl 5-hydroxyisophthalate (12.6 g, 60 mmol) was dissolved in methanol (36 mL) containing 3-amino-1,2-dihydroxypropane (16.4 g, 180 mmol). The mixture was heated to reflux temperature for 10 days, and, after cooling to room temperature, was evaporated. Acetone (100 mL) was added to the residue and the crystalline solid was collected by filtration. The product was purified by recrystallization from acetone. Yield 9.0 g (46%).

$^1$H NMR (DMSO-d$_6$) δ: 3.18–3.28 (m, 2H), 3.36–3.47 (m, 4H), 3.67 (p, 2H, J=8.4 Hz), 4.40 (br s, 4H), 7.39 (s, 2H), 7.78 (s, 1H), 8.36 (t, 2H, J=6.3 Hz).

$^{13}$C NMR (DMSO-d$_6$) δ: 63.04, 70.31, 116.6, 116.7, 135.9, 157.2, 166.2.

N,N-bis(2,3-dihydroxypropyl)-1-hydroxy-2,4,6-triiodobenzene-3,5-dicarboxylic acid diamide N,N-bis(2,3-dihydroxypropyl)-1-hydroxy-2,4,6-triiodobenzene-3,5-dicarboxylic acid diamide (13.1 g, 40 mmol) was dissolved in water (160 mL) and pH was adjusted to 3.9 using aqueous HCl. To this solution, NaICl$_2$ (42.6 g, 50.3%, 40 mmol) was added dropwise during a period of 30 minutes. After standing overnight, the reaction mixture was evaporated. The product was purified by preparative HPLC (RP-18, CH$_3$CN: H$_2$O 15:85, 1% TFA). Yield 22.3 g (79%).

$^1$H NMR (DMSO-d$_6$) δ: 3.08–3.21 (m, 2H), 3.22–3.55 (m, 4H), 3.62–3.75 (m, 2H), 5.4 (br s, 4H), 7.97–8.12 (m, 1H), 8.33–8.44 (m, 1H).

N,N-bis(2,3-dihydroxypropyl)-2,4,6-triiodophenoxide-3,5-dicarboxylic acid diamide N,N-bis(2,3-dihydroxypropyl)-1-hydroxy-2,4,6-triiodobenzene-3,5-dicarboxylic acid diamide (100 mg, 0.14 mmol) was dissolved in water (7 mL) under an atmosphere of argon. PbO$_2$ (1 g) was then added and, after stirring for 10 minutes, the solid was allowed to settle and a sample was withdrawn for ESR analysis.

Overhauser measurement: Enhancement of 38 (20 W microwave power).

ESR: singlet, linewidth 1.08 G.

What is claimed is:

1. An electron spin resonance enhanced nuclear magnetic resonance imaging contrast medium comprising a physiologically tolerable, persistent, water-soluble cyclic π-system free radical, said radical having an inherent linewidth in its esr spectrum of less than 500 mG, said radical having an electron delocalising π-system which comprises at least one homo- or hetero- tricyclic ring, and said radical comprising at least one pair of adjacent ring carbons of a (C═C)$_n$ moiety, where n is a positive integer, or an aryl substituent is substituted to form a fused ring of formula

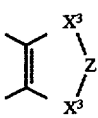

where X$_3$ is oxygen, sulphur, or SO$_2$, and Z is C(CH$_3$)$_2$ or CR$^7_2$ wherein R$^7$ is hydrogen or optionally hydroxylated methyl, with a center ring substituted by two oxygen atoms, together with at least one pharmacologically acceptable carrier or excipient.

2. A contrast medium according to claim 1 wherein the radical is substituted on its skeleton by groups which are sterically hindering groups, electron donor groups, electron withdrawing groups, or solubilizing groups.

3. A method of electron spin resonance investigation of a sample, said method comprising introducing into said sample a persistent cyclic π-system radical as defined in claim 1 as a spin label.

4. A method of magnetometric investigation of a sample, said method comprising introducing into said sample a persistent cyclic π-system radical as defined in claim 1.

5. A method of electron spin resonance enhanced nuclear magnetic resonance investigation of a sample, said method comprising introducing into said sample a persistent, water-soluble cyclic π-system radical, said radical having an inherent linewidth in its esr spectrum of less than 500 mG, said radical having an electron delocalising π-system which comprises at least one homo- or hetero- tricyclic ring, and said radical comprising at least one pair of adjacent ring carbons of a (C=C)$_n$ moiety, where n is a positive integer, or an aryl substituent is substituted to form a fused ring of formula

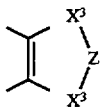

where X$_3$ is oxygen, sulphur, or SO$_2$, and Z is C(CH$_3$)$^7{}_2$ or CRT$^7{}_2$ wherein R$^7$ is hydrogen or optionally hydroxylated methyl, with a center ring substituted by two oxygen atoms, together with at least one pharmacologically acceptable carrier or excipient, exposing said sample to a first radiation of a frequency selected to excite electron spin transitions in said free radical, exposing said sample to a second radiation of a frequency selected to excite nuclear spin transitions in selected nuclei in said sample, detecting free induction decay signals from said sample, and, optionally, generating an image or dynamic flow data from said detected signals.

6. A non-radical precursor to a physiologically tolerable, persistent, water-soluble cyclic π-system free radical, said radical having an inherent linewidth in its esr spectrum of less than 500 mG, said radical having an electron delocalising π-system which comprises at least one homo- or hetero- tricyclic ring, and said radical comprising at least one pair of adjacent ring carbons of a (C=C)$_n$ moiety, where n is a positive integer, or an aryl substituent is substituted to form a fused ring of formula

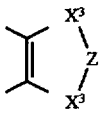

where X$_3$ is oxygen sulphur, or SO$_2$, and Z is C(CH$_3$)$_2$ or CR$^7{}_2$ wherein R$^7$ is hydrogen or optionally hydroxylated methyl, with a center ring substituted by two oxygen atoms.

7. A process for preparing a physiologically tolerable, persistent, water-soluble cyclic π-system free radical, said radical having an inherent linewidth in its esr spectrum of less than 500 mG, said radical having an electron delocalising π-system which comprises at least one homo- or hetero- tricyclic ring, and said radical comprising at least one pair of adjacent ring carbons of a (C=C)$_n$ moiety, where n is a positive integer, or an aryl substituent is substituted to form a fused ring of formula

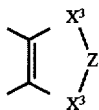

where X$_3$ is oxygen, sulphur, or SO$_2$, and Z is C(CH$_3$)$_2$ or CR$^7{}_2$ wherein R$^7$ is hydrogen or optionally hydroxylated methyl, with a center ring substituted by two oxygen atoms, comprising subjecting a non-radical precursor therefor to a radical generation procedure.

8. A persistent, water-soluble cyclic π-system free radical, said radical having an inherent linewidth in its esr spectrum of less than 500 mG, said radical having an electron delocalising π-system which comprises at least one homo- or hetero- tricyclic ring, and said radical comprising at least one pair of adjacent ring carbons of a (C=C)$_n$ moiety, where n is a positive integer, or an aryl substituent is substituted to form a fused ring of formula

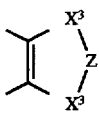

where X$_3$ is oxygen, sulphur, or SO$_2$, and Z is C(CH$_3$)$_2$ or CR$^7{}_2$ wherein R$^7$ is hydrogen or optionally hydroxylated methyl, with a center ring substituted by two oxygen atoms.

* * * * *